United States Patent
Park et al.

(10) Patent No.: US 12,146,155 B2
(45) Date of Patent: Nov. 19, 2024

(54) METHOD FOR CONSTRUCTING HUMAN PLURIPOTENT STEM CELL-DERIVED LIVER ORGANOID HAVING ENHANCED DRUG METABOLIC POTENTIAL AND LIVER ORGANOID CONSTRUCTED BY SAME METHOD

(71) Applicant: KOREA RESEARCH INSTITUTE OF CHEMICAL TECHNOLOGY, Daejeon (KR)

(72) Inventors: Han-Jin Park, Daejeon (KR); Hyemin Kim, Daejeon (KR); Ilkyun Im, Daejeon (KR); Ji-Woo Kim, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 18/547,750

(22) PCT Filed: Apr. 21, 2021

(86) PCT No.: PCT/KR2021/005001
§ 371 (c)(1),
(2) Date: Oct. 31, 2023

(87) PCT Pub. No.: WO2022/181880
PCT Pub. Date: Sep. 1, 2022

(65) Prior Publication Data
US 2024/0141289 A1    May 2, 2024

(30) Foreign Application Priority Data
Feb. 24, 2021  (KR) .................. 10-2021-0024905
Feb. 24, 2021  (KR) .................. 10-2021-0024919

(51) Int. Cl.
*C12N 5/00*     (2006.01)
*C12N 5/0735*   (2010.01)

(52) U.S. Cl.
CPC ......... *C12N 5/0606* (2013.01); *C12N 5/0018* (2013.01); *C12N 2500/24* (2013.01)

(58) Field of Classification Search
CPC . C12N 5/0606; C12N 5/0018; C12N 2500/24
See application file for complete search history.

(56) References Cited

U.S. PATENT DOCUMENTS

| 8,642,339 B2 | 2/2014 | Sato et al. |
| 2021/0395695 A1 | 12/2021 | Kim et al. |

FOREIGN PATENT DOCUMENTS

| KR | 10-2020-0034496 A | 3/2020 |
| KR | 10-2020-0077460 A | 6/2020 |

(Continued)

OTHER PUBLICATIONS

Lonza (SDS Cover Sheet HCM Bullet Kit) (Year: 2024).*
(Continued)

*Primary Examiner* — Arthur S Leonard
*Assistant Examiner* — Keenan A Bates
(74) *Attorney, Agent, or Firm* — Fredrikson & Byron, P.A.

(57) ABSTRACT

The present invention relates to a method for constructing a human pluripotent stem cell-derived liver organoid having enhanced drug metabolic potentials and a liver organoid constructed by the method. Because differentiation is made from human induced pluripotent stem cells dedifferentiated from somatic cells of patients, the cells are easily supplied so that patient-specific liver organoids can be prepared. The organoids can similarly simulate the real human liver structure because they consist of hepatocytes, cholangiocytes, gallbladder cells, and microduct structures, have excellent (Continued)

expression and functions of drug metabolism enzymes, and exhibit drug toxicity, drug metabolic capability, and drug-induced cardiotoxicity. Thus, the organoids can be advantageously used as liver models for searching for pathogenesis of liver diseases and for evaluating drug stability.

14 Claims, 37 Drawing Sheets

(56) References Cited

FOREIGN PATENT DOCUMENTS

| KR | 10-2020-0081331 A | 7/2020 |
|---|---|---|
| WO | 2017/048193 A1 | 3/2017 |

OTHER PUBLICATIONS

Liu et al. Epileptogenesis in organotypic hippocampal cultures has limited dependence on culture medium composition. PLoS One 12: 1-25. (Year: 2017).*
Kulkeaw et al. Generation of human liver organoids from pluripotent stem cell-derived hepatic endoderms. PeerJ 8: 1-20. (Year: 2020).*
ThermoFisher (RPMI 1640; https://www.thermofisher.com/order/catalog/product/11875093) (Year: 2024).*
Wang et al. Human ESC-derived expandable hepatic organoids enable therapeutic liver repopulation and pathophysiological modeling of alcoholic liver injury. Cell Research 29: 1009-1026. (Year: 2019).*
Ramli et al. Human Pluripotent Stem Cell-Derived Organoids as Models of Liver Disease. Gastroenterology 159: 1471-1486. (Year: 2020).*
International Search Report and Written Opinion received for PCT Patent Application No. PCT/KR2021/005001, mailed on Nov. 22, 2021, 11 pages (5 pages of English Translation and 6 pages of Original Document).
Ramli. M. N. et al., "Human Pluripotent Stem Cell-Derived Organoids as Models of Liver Disease," Gastroenterology, vol. 159, 2020, pp. 1471-1486.
Akbari et al. (2019). Robust, Long-Term Culture of Endoderm-Derived Hepatic Organoids for Disease Modeling. Stem Cell Reports 13, 627-641.
Cells, vol. 9(872), doi: 10.3390/cells9040872(Apr. 2, 2020.).
FenFang Wu et al., 'Generation of hepatobiliary organoids from human induced pluripotent stem cells', Journal of Hepatology, vol. 70, pp. 1145-1158(2019).
Mun et al. (2019). Generation of expandable human pluripotent stem cell-derived hepatocyte-like liver organoids. J Hepatol 71, 970-985.
Wang et al. (2019). Human ESC-derived expandable hepatic organoids enable therapeutic liver repopulation and pathophysiological modeling of alcoholic liver injury. Cell Res 29, 1009-1026.

* cited by examiner

200nm

METHOD FOR CONSTRUCTING HUMAN PLURIPOTENT STEM CELL-DERIVED LIVER ORGANOID HAVING ENHANCED DRUG METABOLIC POTENTIAL AND LIVER ORGANOID CONSTRUCTED BY SAME METHOD

CROSS-REFERENCES TO RELATED APPLICATION

This patent application claims the benefit of priority under 35 U.S.C. § 119 from Korean Patent Application 10-2021-0024905 filed on Feb. 24, 2021 and Korean Patent Application 10-2021-0024919 filed on Feb. 24, 2021 the contents of which are incorporated herein by reference.

BACKGROUND OF THE INVENTION

1. Field of the Invention

The present invention relates to a method for constructing a human pluripotent stem cell-derived liver organoid having enhanced drug metabolic potentials and a liver organoid constructed by the method.

2. Description of the Related Art

The liver is a central organ of metabolic and physiological homeostasis with diverse functions such as metabolism, protein synthesis, bile production, and red blood cell removal. Hepatocytes, the hepatic parenchymal cells, are primarily responsible for maintaining liver homeostasis and are therefore the target of many diseases. Despite recent technological advances in disease modeling of liver failure, there is a need for models of congenital and progressive metabolic diseases that can lead to the end-stage of liver failure. Furthermore, since the liver has a specific function for the detoxification of pharmaceuticals, a model that mimics human hepatocytes is required as a tool for evaluating drug metabolism and toxicity in drug development. Although current in vitro and in vivo liver models have contributed greatly to elucidating the pathogenesis of liver diseases and evaluating drug stability, they still have limitations that do not fully reflect the physiology of the human liver. Animal models have limitations in predicting drug toxicity due to interspecies differences. In addition, primary human hepatocytes (PHH) are the standard in vitro liver model, but they have limited accessibility to the human liver tissue and unstable function. Also, liver cancer cell lines are not normal cells, so their drug metabolism enzymes are not fully expressed or their function is reduced. Therefore, they are not suitable for evaluating drug toxicity. Thus, it is necessary to construct a liver model that can mimic human liver metabolism and has drug metabolism capability.

An organoid is an organ-specific cell aggregate made by three-dimensional cultivation, aggregation, or recombination of stem cells that is capable of self-renewal and is sometimes referred to as a "mini-organ" or "pseudo-organ. Organoids are very useful for basic research as they allow research that is difficult to implement in animal models, such as molecular signal regulation, to be performed in vitro in a form similar to the actual organ, and can be used in various fields such as human development process, disease model establishment, drug efficacy evaluation screening, development of drug toxicity evaluation platform, and development of cell therapy.

A human liver organoid was first developed from adult human liver tissue using a culture medium containing R-Spondin 1. Primary human hepatocytes (PHH) were also applied to 3D organoid culture, and the generation of liver buds and liver organoids from human pluripotent stem cells (hPSC) was reported. Human pluripotent stem cell-derived liver organoids (hHO) have been proposed as in vitro models for disease modeling such as genetic and metabolic disorders, cell therapy and drug toxicity testing.

Currently, research for the establishment of various organoids has been conducted, and liver organoids have also been developed. Prior art related to a method for constructing a liver organoid includes the following references: Literatures confirmed that liver organoids were generated through an expansion step derived from definitive endoderm and hepatic endoderm, the generated liver organoids were capable of proliferation, and they enabled modeling of citrullinemia type 1 and alcoholic liver injury (Akbari et al. (2019). Robust, Long-Term Culture of Endoderm-Derived Hepatic Organoids for Disease Modeling. Stem Cell Reports 13, 627-641., Wang et al. (2019). Human ESC-derived expandable hepatic organoids enable therapeutic liver repopulation and pathophysiological modeling of alcoholic liver injury. Cell Res 29, 1009-1026.), A literature producing liver organoids through an expansion step derived from 3D spherical hPSC-derived mature hepatocyte-like cells (HLC), and proposing the liver organoids as a model to evaluate drug-induced hepatic steatosis (Mun et al. (2019). Generation of expandable human pluripotent stem cell-derived hepatocyte-like liver organoids. J Hepatol 71, 970-985.), and U.S. Pat. No. 8,642,339B2, which discloses a method for generating organoids by collecting human hepatocytes and isolating stem cells therefrom.

However, liver organoids known so far have limitations in reproducing drug metabolism and transport functions. As an in vitro model for drug toxicity and efficacy testing, liver organoids should be reproducibly produced and should exhibit drug metabolism and transport functions similar to those of adult liver and primary human hepatocytes (PHH). To this end, it is necessary to construct a liver organoid expressing the liver cytochrome P450 (CYP450) protein, which is a superfamily enzyme mainly responsible for the biotransformation of most pharmaceuticals and xenobiotics. It is necessary to develop a liver organoid that can function as a toxicity screening platform through detailed functional analysis such as drug metabolism and transport.

Accordingly, the present inventors found that when the liver organoids were constructed by culturing in a medium without R spondin-1, Noggin, and EGF, or selectively culturing in a medium containing iron ions, the expression and function of drug metabolism enzymes were excellent, and they exhibited drug-induced toxicity, and completed the present invention.

SUMMARY OF THE INVENTION

It is an object of the present invention to provide a method for constructing a liver organoid having enhanced drug metabolic potentials and a liver organoid constructed by the method.

To achieve the above object, the present invention provides a method for constructing a liver organoid comprising the following steps:
1) a step of differentiating human pluripotent stem cells (hPSCs) into definitive endoderm (DE) cells;
2) a step of differentiating the definitive endoderm cells of step 1) into hepatic endoderm (HE) cells;

3) a step of differentiating the hepatic endoderm cells of step 2) into a hepatic endoderm organoid (hHEO); and
4) a step of differentiating the hepatic endoderm organoid of step 3) into a liver organoid (hepatic organoid, hHO).

In addition, the present invention provides a liver organoid having enhanced drug metabolic capability constructed by the method.

ADVANTAGEOUS EFFECT

The present invention relates to a method for constructing a human pluripotent stem cell-derived liver organoid having enhanced drug metabolic potentials and a liver organoid constructed by the method. Because differentiation is made from human induced pluripotent stem cells dedifferentiated from somatic cells of patients, the cells are easily supplied so that patient-specific liver organoids can be prepared. The organoids can similarly simulate the real human liver structure because they consist of hepatocytes, cholangiocytes, gallbladder cells, and microduct structures, have excellent expression and functions of drug metabolism enzymes, and exhibit drug toxicity, drug metabolic capability, and drug-induced cardiotoxicity. Thus, the organoids can be advantageously used as liver models for searching for pathogenesis of liver diseases and for evaluating drug stability.

DESCRIPTION OF THE PREFERRED EMBODIMENTS

Figure 1:
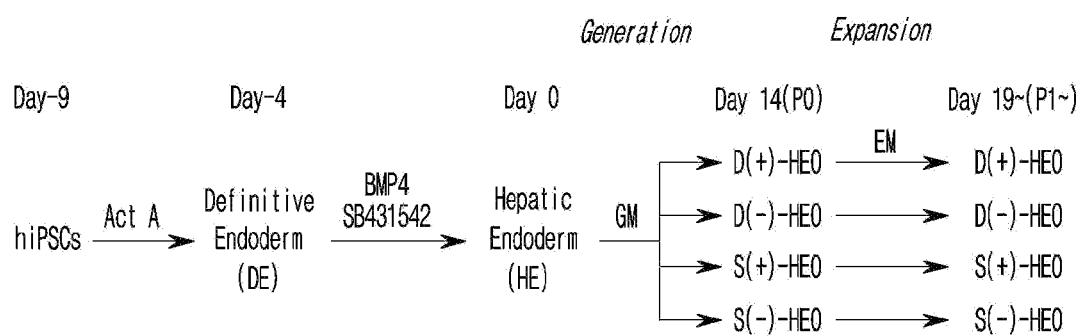
FIG. 1 is a schematic diagram showing the method for constructing a liver organoid from human induced pluripotent stem cells.

Hereinafter, the present invention is described in detail.

The present invention provides a method for constructing a liver organoid comprising the following steps:
1) a step of differentiating human pluripotent stem cells (hPSCs) into definitive endoderm (DE) cells;
2) a step of differentiating the definitive endoderm cells of step 1) into hepatic endoderm (HE) cells;
3) a step of differentiating the hepatic endoderm cells of step 2) into a hepatic endoderm organoid (hHEO); and
4) a step of differentiating the hepatic endoderm organoid of step 3) into a liver organoid (hepatic organoid, hHO).

The human pluripotent stem cells may be human embryonic stem cells (hESCs) or human induced pluripotent stem cells (hiPSCs), and may be of human origin, but not always limited thereto.

If it is confirmed by flow cytometry that the hepatic endoderm cells in step 2) are more than 95% of the total cells, proceed to step 3).

The differentiation may be to differentiate stem cells in a culture vessel coated with Matrigel to simulate the microenvironment of cells, but not always limited thereto, and a culture vessel coated with fibronectin or laminin can be used.

The hepatic endoderm organoid can be constructed in the form of droplet or in suspension.

The hepatic endoderm organoid of step 3) can be cryopreserved and thawed.

The droplet-shaped hepatic endoderm organoid can be constructed by mixing hepatic endoderm cells with Matrigel GFR (growth factor reduced) stock solution, dispensing the mixture into a dome structure in a well plate, and solidifying thereof.

The suspension-type hepatic endoderm organoid can be constructed by adding hepatic endoderm cells to a well plate containing a medium comprising Matrigel GFR (growth factor reduced).

The differentiation of step 3) consists of a generation stage and an expansion stage.

The generation stage is conducted in a hepatic endoderm organoid production medium (GE medium, GM).

The hepatic endoderm organoid production medium contains fibroblast growth factor 10 (FGF10), hepatocyte growth factor (HGF), nicotinamide, [Leu$^{15}$]-Gastrin I human, N-acetyl-L-cysteine, A83-01, Forskolin and CHIR99021, and can optionally include Matrigel GFR (growth factor reduced) when preparing organoids in suspension.

The FGF10 can be included in the medium at 30 to 70 ng/mℓ, preferably at 40 to 60 ng/mℓ, or more preferably at 45 to 55 ng/mℓ.

The HGF can be included in the medium at 5 to 45 ng/mℓ, preferably at 15 to 35 ng/mℓ, or more preferably at 20 to 30 ng/mℓ.

The nicotinamide can be included in the medium at 1 to 20 mM, preferably at 5 to 15 mM, or more preferably at 7 to 13 mM.

The [Leu$^{15}$]-Gastrin I human can be included in the medium at 1 to 20 nM, preferably at 5 to 15 nM, or more preferably at 7 to 13 nM.

The N-acetyl-L-cysteine can be included in the medium at 0.25 to 2.25 mM, preferably at 0.5 to 2 mM, or more preferably at 1 to 1.5 mM.

The A83-01 can be included in the medium at 1 to 9 µM, preferably at 3 to 7 µM, or more preferably at 4 to 6 µM.

The Forskolin can be included in the medium at 5 to 15 µM, preferably at 7 to 13 µM, or more preferably at 8 to 12 µM.

The CHIR 99021 can be included in the medium at 1 to 5 µM, preferably at 2 to 4 µM, or more preferably at 2.5 to 3.5 µM.

The Matrigel GFR can be included in the medium at 0.2 to 0.8 mg/mℓ, preferably at 0.3 to 0.7 mg/mℓ, or more preferably at 0.4 to 0.6 mg/mℓ.

The generation stage can be performed for 10 to 18 days, preferably 12 to 16 days, and more preferably 13 to 15 days.

The expansion stage is conducted in a medium with the same composition as the hepatic endoderm organoid production medium used in the generation stage.

The expansion stage can be performed for 3 to 7 days, and preferably can be performed for 4 to 6 days.

Compared to the composition of the medium used in the conventional liver organoid culture method (Hugh et al., Long-Term Culture of Genome-Stable Bipotent Stem Cells from Adult Human Liver, Cell (2015)), the medium used in the generation stage during the differentiation of hepatic endoderm cells into hepatic endoderm organoids does not contain R spondin-1, Noggin, and EGF, and the medium used in the expansion stage does not include R spondin-1 and EGF.

The step of differentiating hepatic endoderm cells into hepatic endoderm organoids can be performed for 13 to 25 days, preferably for 15 to 23 days, and more preferably for 17 to 21 days.

The step of differentiating the hepatic endoderm organoid into the liver organoid in step 4) can be performed in a medium containing iron ions.

The medium containing iron ions may be a medium comprising any one selected from the group consisting of ferric citrate (FC), iron chloride (FeCl$_3$), iron sulfate (Fe$_2$SO$_4$), ferric sulfate (Fe$_2$(SO$_4$)$_3$), iron nitrate (Fe(NO$_3$)$_3$), and pentacarbonyl iron (Fe(CO)$_5$), but not always limited thereto.

The ferric citrate can be included at a concentration of 10 to 30 µM, and preferably at a concentration of 15 to 25 µM.

The liver organoid of step 4) can be constructed in the form of droplet or in suspension.

The liver organoid includes biliary-like cells, gallbladder-like cells, and hepatocyte-like cells.

The differentiation of step 4) comprises a step of subculturing a hepatic endoderm organoid and a step of differentiating the hepatic endoderm organoid into a liver organoid.

The droplet-shaped liver organoid is constructed by performing a step of subculturing a droplet-shaped hepatic endoderm organoid and a step of differentiating the droplet-shaped hepatic endoderm organoid into a liver organoid.

The suspension-type liver organoid is constructed by performing a step of subculturing a suspension-type hepatic endoderm organoid and a step of differentiating the suspension-type hepatic endoderm organoid into a liver organoid.

The step of subculturing a hepatic endoderm organoid is performed in a hepatic endoderm organoid expansion medium (EM).

The hepatic endoderm organoid expansion medium contains bone morphogenetic protein 7 (BMP7), fibroblast growth factor 10 (FGF10), hepatocyte growth factor (HGF), nicotinamide, [Leu$^{15}$]-Gastrin I human, N-acetyl-L-cysteine, A83-01, Forskolin and CHIR99021, and can optionally include Matrigel GFR (growth factor reduced) when preparing liver organoids in suspension.

The BMP7 can be included in the medium at 5 to 45 ng/mℓ, preferably at 15 to 35 ng/mℓ, or more preferably at 20 to 30 ng/mℓ.

The FGF10 can be included in the medium at 30 to 70 ng/mℓ, preferably at 40 to 60 ng/mℓ, or more preferably at 45 to 55 ng/mℓ.

The HGF can be included in the medium at 5 to 45 ng/mℓ, preferably at 15 to 35 ng/mℓ, or more preferably at 20 to 30 ng/mℓ.

The nicotinamide can be included in the medium at 1 to 20 mM, preferably at 5 to 15 mM, or more preferably at 7 to 13 mM.

The [Leu$^{15}$]-Gastrin I human can be included in the medium at 1 to 20 nM, preferably at 5 to 15 nM, or more preferably at 7 to 13 nM.

The N-acetyl-L-cysteine can be included in the medium at 0.25 to 2.25 mM, preferably at 0.5 to 2 mM, or more preferably at 1 to 1.5 mM.

The A83-01 can be included in the medium at 1 to 9 µM, preferably at 3 to 7 µM, or more preferably at 4 to 6 µM.

The Forskolin can be included in the medium at 5 to 15 µM, preferably at 7 to 13 µM, or more preferably at 8 to 12 µM.

The CHIR99021 can be included in the medium at 1 to 5 µM, preferably at 2 to 4 µM, or more preferably at 2.5 to 3.5 µM.

The Matrigel GFR can be included in the medium at 0.2 to 0.8 mg/ml, preferably at 0.3 to 0.7 mg/ml, or more preferably at 0.4 to 0.6 mg/ml.

The step of subculturing a hepatic endoderm organoid can be performed for 2 to 8 days, preferably for 3 to 7 days, and more preferably for 4 to 6 days.

The step of differentiating the hepatic endoderm organoid into a liver organoid is performed in a liver organoid differentiation medium (DM).

The liver organoid differentiation medium contains bone morphogenetic protein 7 (BMP7), fibroblast growth factor 19 (FGF19), hepatocyte growth factor (HGF), [Leu$^{15}$]-Gastrin I human, N-acetyl-L-cysteine, A83-01, DAPT and dexamethasone, and can optionally include Matrigel GFR (growth factor reduced) when preparing liver organoids in suspension. In addition, to further enhance the drug metabolic capability, ferric citrate (FC) can be further included in the medium.

The BMP7 can be included in the medium at 5 to 45 ng/ml, preferably at 15 to 35 ng/ml, or more preferably at 20 to 30 ng/ml.

The FGF19 can be included in the medium at 50 to 150 ng/ml, preferably at 70 to 130 ng/ml, or more preferably at 90 to 110 ng/ml.

The HGF can be included in the medium at 5 to 45 ng/ml, preferably at 15 to 35 ng/ml, or more preferably at 20 to 30 ng/ml.

The [Leu$^{15}$]-Gastrin I human can be included in the medium at 1 to 20 nM, preferably at 5 to 15 nM, or more preferably at 7 to 13 nM.

The N-acetyl-L-cysteine can be included in the medium at 0.25 to 2.25 mM, preferably at 0.5 to 2 mM, or more preferably at 1 to 1.5 mM.

The A83-01 can be included in the medium at 0.1 to 0.9 μM, preferably at 0.2 to 0.8 μM, or more preferably at 0.4 to 0.6 μM.

The DAPT can be included in the medium at 0.2 to 1.8 μl, preferably at 0.5 to 1.5 μl, or more preferably at 0.8 to 1.2 μl.

The dexamethasone can be included in the medium at 1 to 5 μM, preferably at 2 to 4 μM, or more preferably at 2.5 to 3.5 μM.

The Matrigel GFR can be included in the medium at 0.2 to 0.8 mg/ml, preferably at 0.3 to 0.7 mg/ml, or more preferably at 0.4 to 0.6 mg/ml.

The ferric citrate can be included in the medium at a concentration of 10 to 30 μM, and preferably at a concentration of 15 to 25 μM.

The step of differentiating the hepatic endoderm organoid into a liver organoid can be performed for 10 to 20 days, preferably for 12 to 18 days, and more preferably for 13 to 17 days.

In addition, R spondin-1 and EGF are not included in the step of subculturing a hepatic endoderm organoid, and EGF is not included in the step of differentiating the hepatic endoderm organoid into a liver organoid during the step of differentiating the hepatic endoderm organoid into the liver organoid compared to the conventional culture method.

In conclusion, in the step of differentiating into a hepatic endoderm organoid, culturing in a culture medium that does not contain R-spondin 1, Noggin and EGF has an effect on the stage of organoid maturation, and in the step of differentiating into a liver organoid, removal of R-spondin 1 and EGF from the culture medium promotes the liver organoid maturation by increasing the expression levels of genes involved in liver and drug metabolism.

The differentiation in step 4) can be performed for 10 to 30 days, preferably for 13 to 27 days, and more preferably for 15 to 25 days.

In addition, the present invention provides a liver organoid having enhanced drug metabolic capability constructed by the method for constructing a liver organoid above.

The liver organoid expresses cytochrome P450 (CYP450) at a high level.

Cytochrome P450 (CYP450) is a superfamily of enzymes having heme as a prosthetic group and is known as a representative catalytic enzyme that performs oxidative metabolism on various exogenous substances such as most drugs and environmental materials or endogenous substances such as steroids and lipids. CYP450 enzymes get their name from the fact that the iron ions contained in heme exhibit a specific absorbance spectrum at 450 nm when bound to carbon monoxide in a reduced state.

The primary function of CYP450 enzymes is monooxygenation (mixed-function oxidase reaction) on a variety of substrates, which requires oxygen molecules and NADPH reducing substances. One atom of the oxygen molecule binds to the substrate being oxidized and the other atom is reduced to water. In the microsomal CYP450 system, which is abundant in hepatocytes, CYP450 enzymes are located in the membrane of the endoplasmic reticulum and receive electrons from the NADPH-P450 reductase coexisting in the membrane to perform oxidation reaction.

The cytochrome P450 is at least one selected from the group consisting of CYP1A2, CYP2C9, CYP2C19, CYP2D6, and CYP3A4.

CYP1A2, CYP2C9, CYP2C19, CYP2D6, and CYP3A4 are types of cytochrome P450, and have a function of primarily metabolizing 95% of drugs in use.

In addition, the liver organoid can be used to evaluate the drug-induced toxicity.

Furthermore, the liver organoid can be used to evaluate the drug-induced cardiotoxicity.

Figure 5:
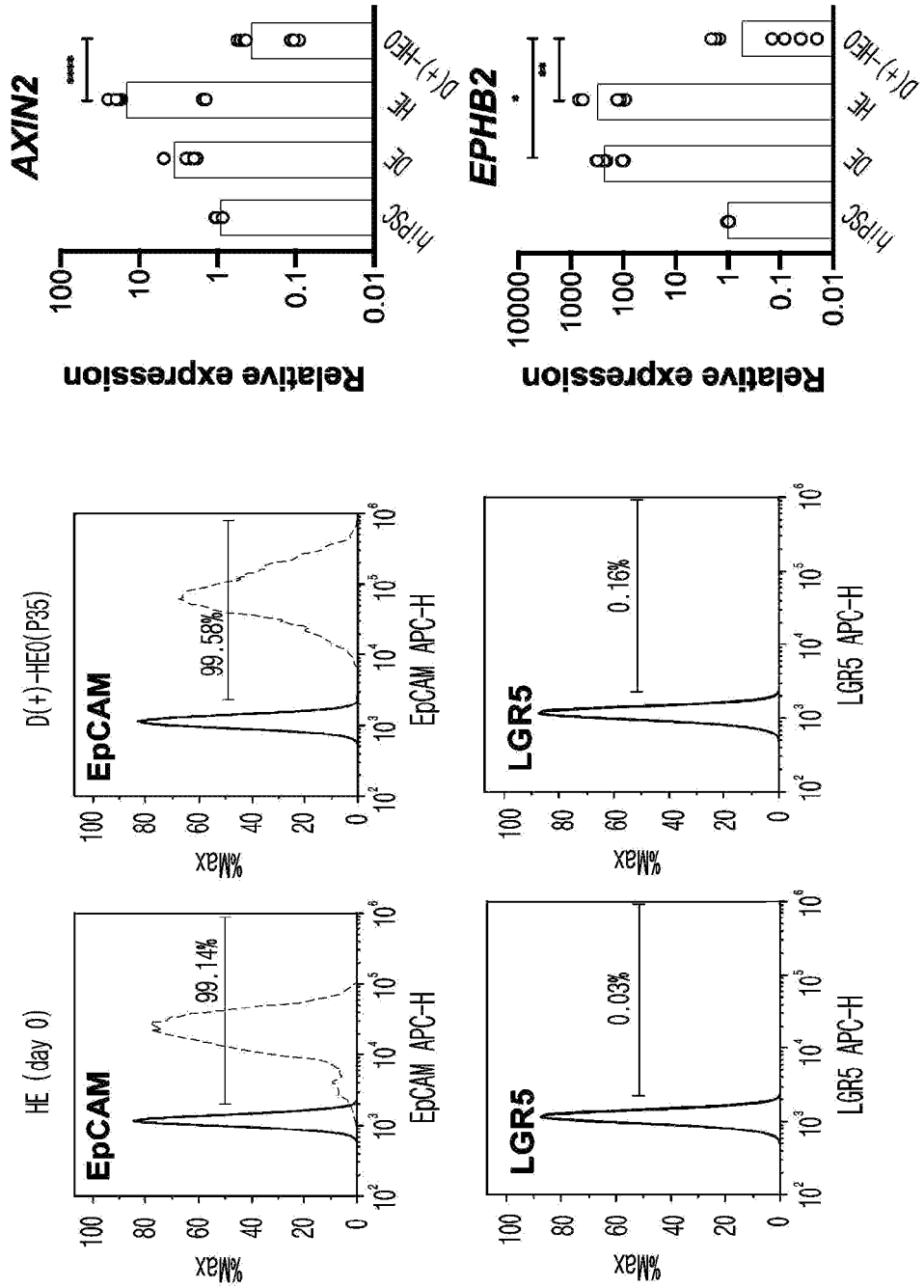
FIG. 5 is a set of graphs showing the number of cells expressing LGR5, a target protein of Wnt that binds to EpCAM and R-spondin 1, the markers of hepatic progenitor cells/stem cells, in hepatic endoderm (HE) cells and droplet-shaped hepatic endoderm organoid (D-HEO) measured by flow cytometry, and the expression of the target genes AXIN2 and EPHB2 measured by RT-qPCR, indicating that Wnt signaling is not required in the hepatic endoderm organoids compared to hepatic endoderm cells.
Figure 10:
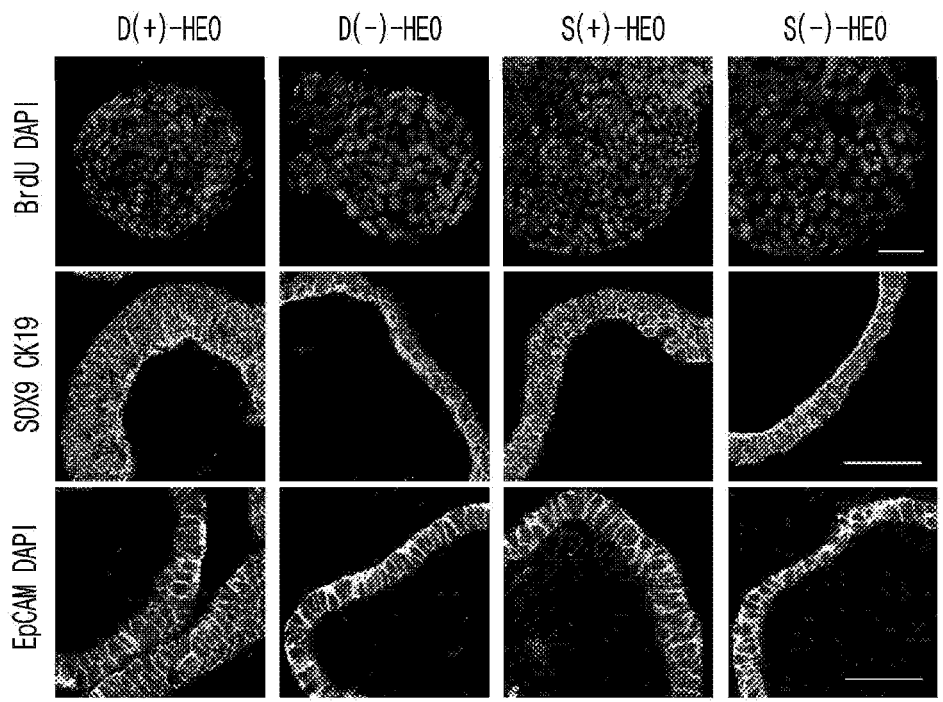
FIG. 10 is a set of photographs showing the expression of the hepatic progenitor cell markers SOX9, CK19, and EpCAM in hepatic endoderm organoids cultured under four conditions, D(+)-HEO, D(−)-HEO, S(+)-HEO, and S(−)-HEO.
Figure 15:
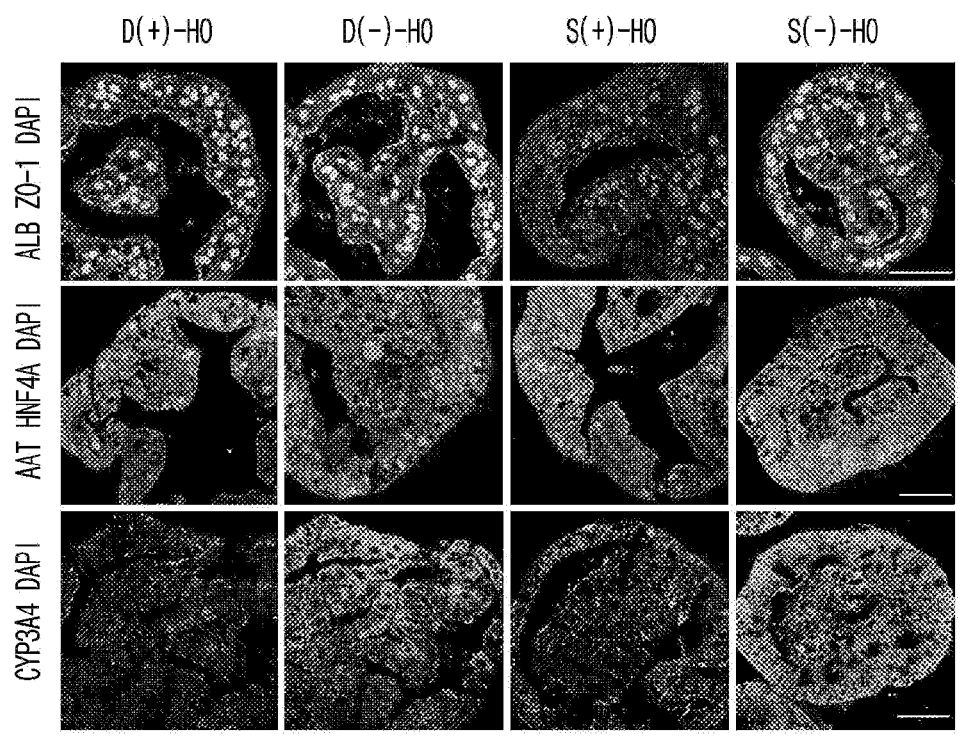
FIG. 15 is a set of photographs showing the expression of the liver markers ALB, AAT, and CYP3A4 in liver organoids cultured under four conditions, D(+)-HO, D(−)-HO, S(+)-HO, and S(−)-HO.
Figure 18:
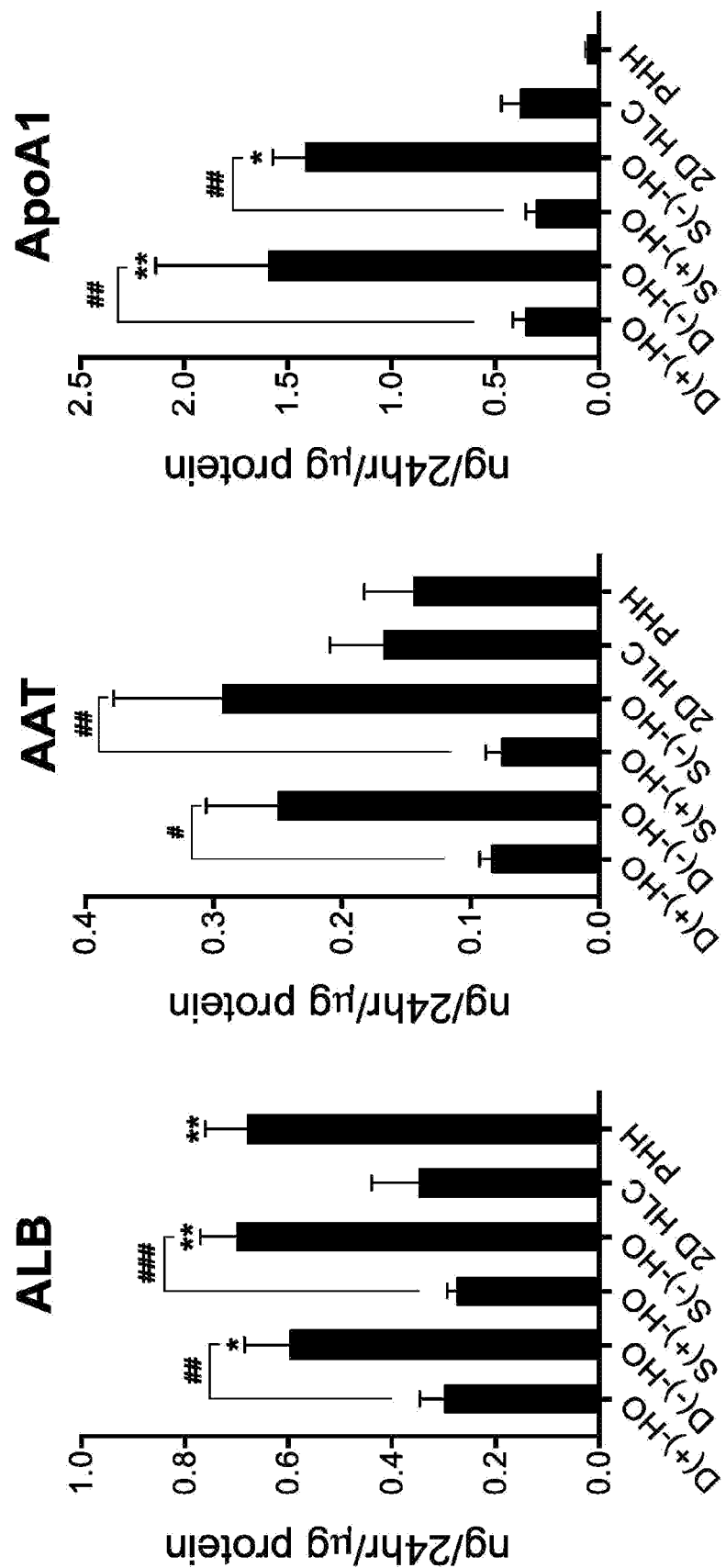
FIG. 18 is a set of graphs showing that the expression of ALB (albumin), AAT (alpha 1-antitrypsin), and ApoA1 (apolipoprotein A1) was increased in D(−)-HO and S(−)-HO than in D(+)-HO and S (+) -HO.
Figure 27:
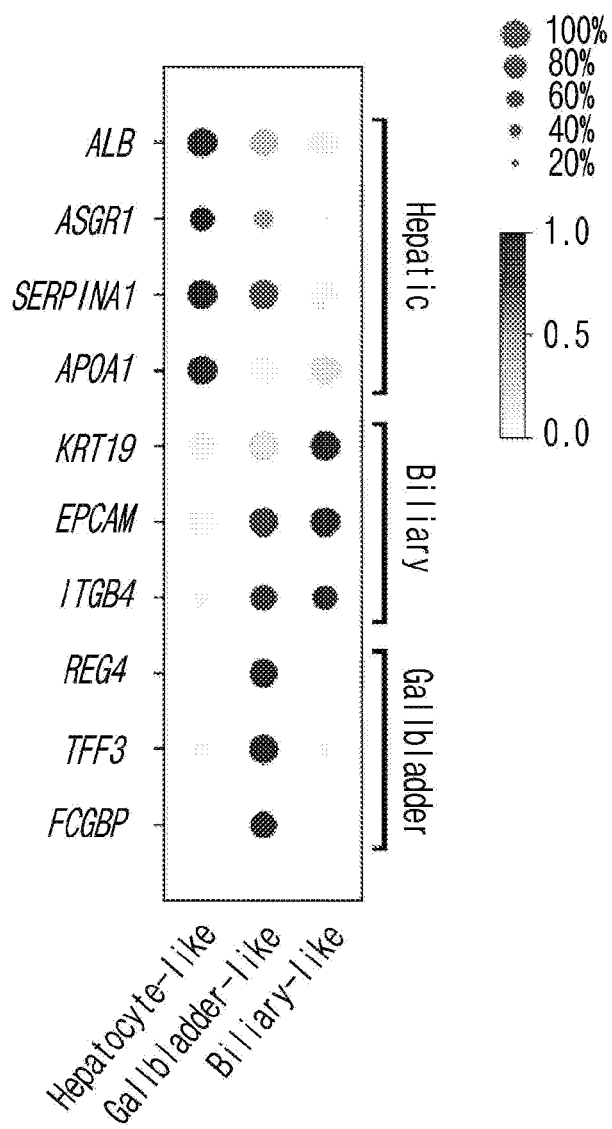
FIG. 27 is a diagram confirming that specific markers of each group are exclusively expressed in each cluster.
Figure 28:
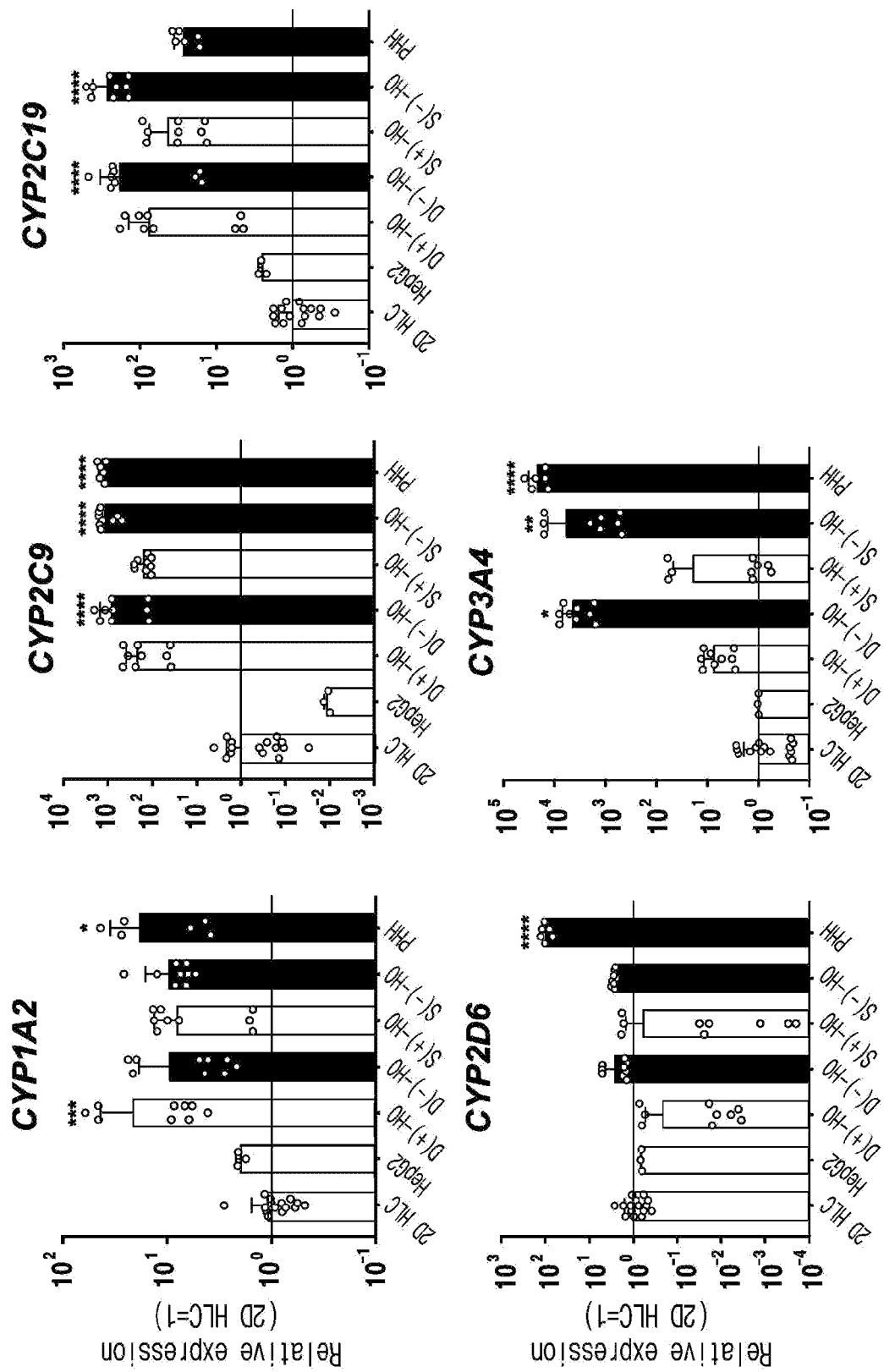
FIG. 28 is a set of graphs confirming that the expression levels of four CYP450 genes are higher in D(−)-HO and S(−)-HO than in D(+)-HO and S(+)-HO, indicating that liver organoids cultured under D(−)-HO and S(−)-HO conditions have an enhanced drug metabolic capability.
Figure 29:
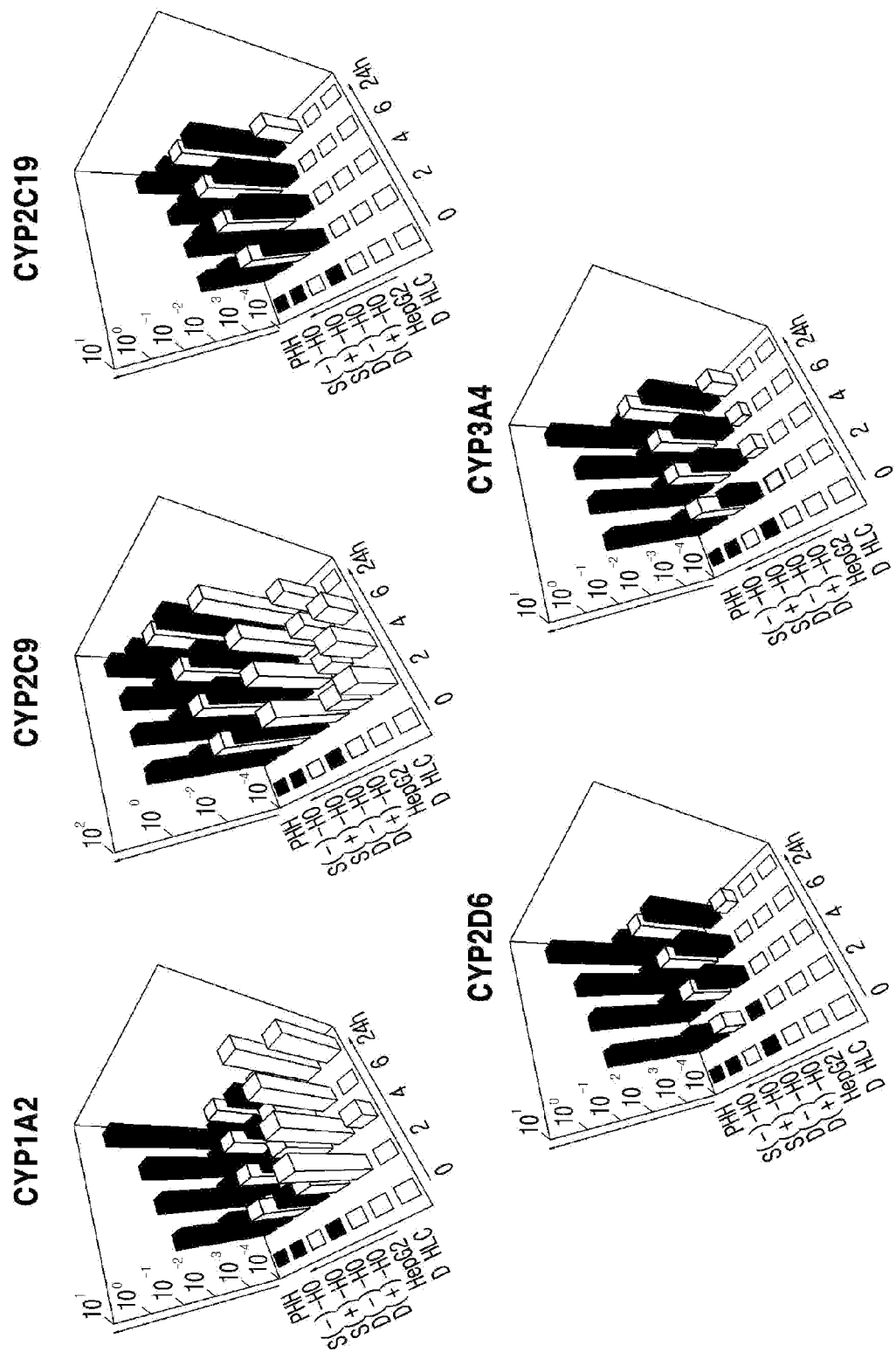
FIG. 29 is a set of graphs showing the activities of major CYP450 genes in D(−)-HO, S(−)-HO, primary human hepatocytes (PHH), liver cancer cell line (HepG2), and 2D hPSC-derived hepatocyte-like cells (2D HLC).

In specific embodiments of the present invention, it was confirmed that Wnt signaling was not required in the step of differentiating a hepatic endoderm organoid from hepatic endoderm cells (FIG. 5). It was also confirmed that the number of organoids constructed in a medium without R-Spondin 1, Noggin, and EGF (RNE) was similar to or higher than the number of organoids constructed in a medium containing RNE (FIGS. 6 and 7), the rate of organoid formation was increased (FIG. 8), and the hepatic progenitor cell markers SOX9, CK19, and EpCAM were well expressed (FIG. 10). In addition, when liver organoids were differentiated from hepatic endoderm organoids in a culture medium without EGF, it was confirmed that the expression of major liver genes was increased (FIGS. 13a and 13b), the liver markers ALB, AAT, and CYP3A4 were expressed (FIG. 15), the expression levels of the liver markers were high in D(−)-HO and S(−)-HO (FIGS. 16a, 16b, and 16c), and the expression of the liver markers ALB (albumin), AAT (alpha 1-antitrypsin) and ApoA1 (apolipoprotein A1) was increased in D(−)-HO and S(−)-HO compared to D(+)-HO and S(+)-HO (FIG. 18). It was also confirmed that the expression of apical transporters was high in the liver organoid (FIG. 20), which included biliary-like cells, gallbladder-like cells, and hepatocyte-like cells (FIGS. 25 to 27), and the expression levels of the drug metabolism enzyme CYP450 genes were higher in D(−)-HO and S(−)-HO than in D(+)-HO and S(+)-HO (FIGS. 28 and 29). Furthermore, when liver organoids were differentiated by adding ferric citrate to a liver organoid differentiation medium having the composition of Table 8 or Table 9 (FIG.

Figure 33:
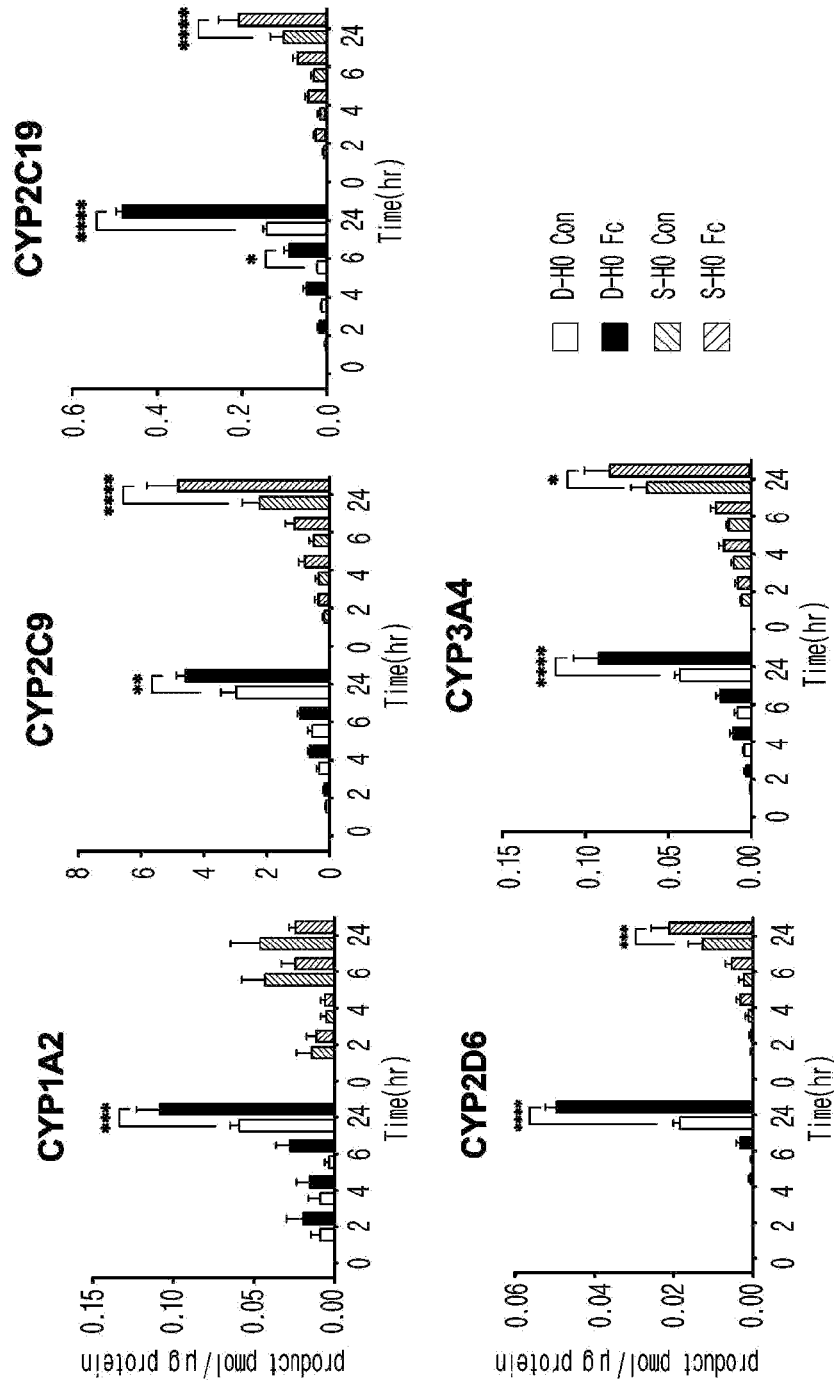
FIG. 33 is a set of graphs showing the activity of CYP450 enzymes measured for 24 hours, indicating that the activity of CYP450, drug metabolism enzymes, is increased when differentiated into suspension-type liver organoids using a liver organoid differentiation medium containing ferric citrate.
Figure 34:
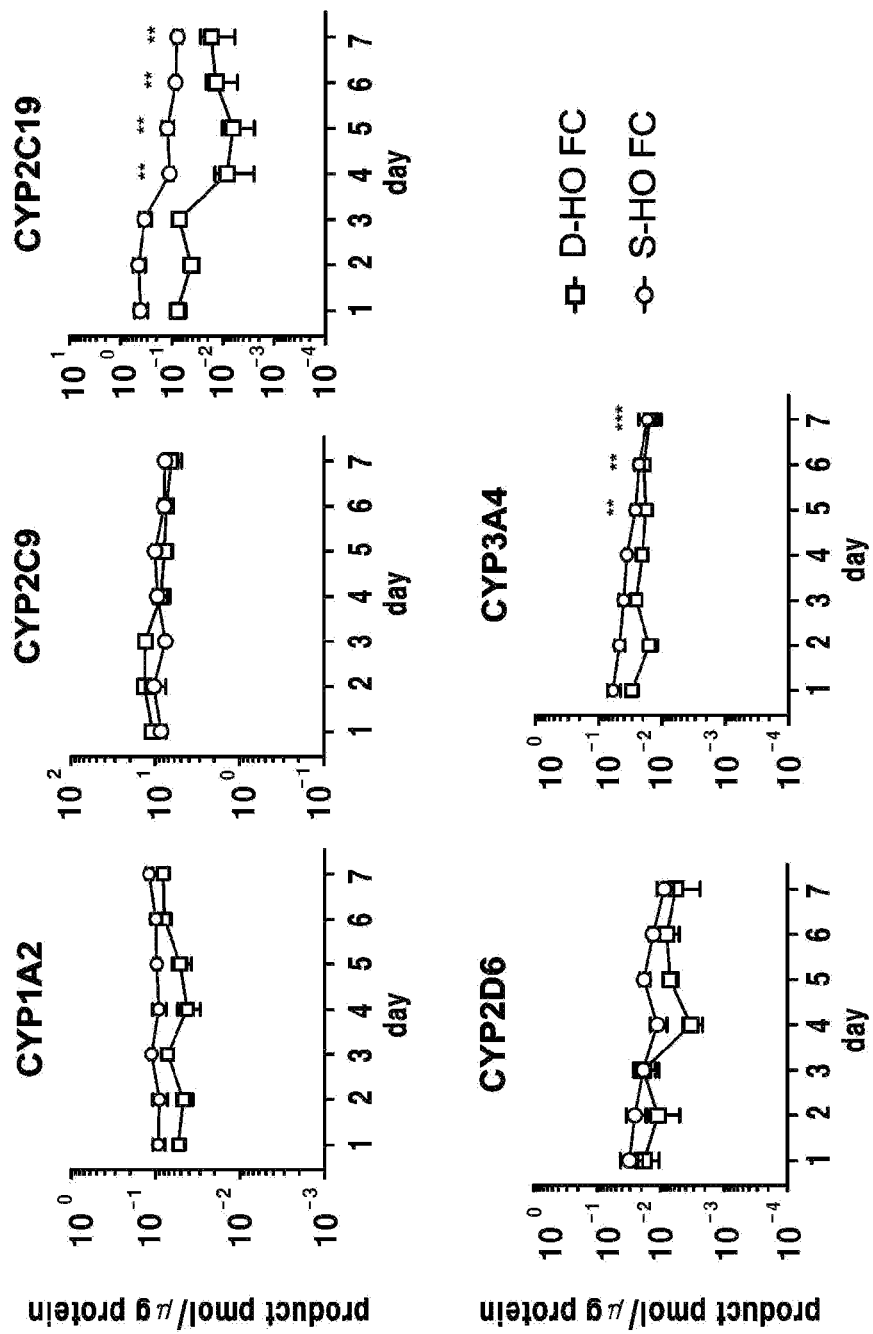
FIG. 34 is a set of graphs showing the activity of CYP450 enzymes measured for 7 days, indicating that the activity of CYP450, drug metabolism enzymes, is maintained when differentiated into suspension-type liver organoids using a liver organoid differentiation medium containing ferric citrate.

30), the CYP450 activity was significantly increased (FIG. 33), and the enzyme activity was maintained for a long period of time (FIG. 34). In addition, it was confirmed that the liver organoid differentiated by adding iron citrate showed cytotoxicity to 8 kinds of drugs (FIG. 35), demonstrated CYP450-mediated drug metabolic capability (FIG. 36), had the ability to metabolize acetaminophen and fimasartan (FIGS. 37 to 42), and exhibited cardiotoxicity by cyclophosphamide and terfenadine (FIGS. 43 to 48).

Therefore, the organoids constructed by the present invention can be advantageously used as liver models for searching for pathogenesis of liver diseases and for evaluating drug stability.

Hereinafter, the present invention will be described in detail by the following examples and experimental examples.

However, the following examples and experimental examples are only for illustrating the present invention, and the contents of the present invention are not limited thereto.

EXAMPLE 1: PREPARATION OF HUMAN HEPATIC ENDODERM ORGANOIDS (HHEOS) DERIVED FROM HUMAN INDUCED PLURIPOTENT STEM CELLS (IPSCS)

<1-1> Plate Coating and Culture of Human Pluripotent Stem Cells (Day −10)

First, vitronectin XF (Cat*.07180, Stem cell technologies) was added to a cell culture plate to coat the wells of the plate. Human induced pluripotent stem cells (hiPSCs) (provided by Dr. Yongman Han, KAIST) derived from human dermal fibroblasts through ectopic expression of OCT4, SOX2, KLF4 and c-MYC were cultured with mTeSR™-E8™ medium (Cat*. 05940, Stem cell technologies) on the coated plate under 37° C., 5% $CO_2$ conditions. hiPSCs were subcultured every 3 or 4 days with dissociation using $Ca^{2+}$/$Mg^{2+}$ free Dulbecco's phosphate-buffered saline (DPBS) supplemented with 0.5 mM EDTA. At this time, the medium was replaced every day during the subculture period.

Diluted Matrigel (hESC qualified Matrigel, Corning, Cat No. 354277) was added to a 12-well plate (0.5 mℓ per well), and the plate was coated with Matrigel at 37° C. for 30 minutes. Then, the cultured human induced pluripotent stem cells were taken out, the medium was removed, and 1 mℓ of $Ca^{2+}$/$Mg^{2+}$ free DPBS supplemented with 0.5 mM EDTA was added to each well of the plate, followed by culture at 37° C. for 4 to 5 minutes. EDTA was removed by tilting the plate, and the cells were recovered using 1 mℓ of 12 mℓ of mTeSR™-E8™ medium containing 2 μM of Y27632. The recovered cells were placed in a conical tube containing 11 mℓ of mTeSR™-E8™ medium containing 2 μM Y27632 and mixed by gentle pipetting. The recovered cells were dispensed in a plate coated with Matrigel (1 mℓ per well) and cultured for one day at 37° C., 5% $CO_2$ conditions, and human induced pluripotent stem cells were seeded in a plate coated with Matrigel.

<1-2> Differentiation of Human Pluripotent Stem Cells into Definitive Endoderm (DE) Cells (Day −9 to Day −4)

To differentiate the human induced pluripotent stem cells cultured in Examples <1-1> into definitive endoderm cells, the following procedure was performed.

Specifically, 12 mℓ of the endodermal differentiation medium 1 (DE medium 1) with the composition of Table 1 below was made to 37° C., and then the medium was added to the plate containing the human induced pluripotent stem cells cultured in Example <1-1> (1 mℓ per well), followed by culture in a 37° C., 5% $CO_2$ incubator for 24 hours. Then, the medium was replaced with the endoderm differentiation medium 2 (DE medium 2) with the composition of Table 2, and cultured in a 37° C., 5% $CO_2$ incubator for 4 days. During the culture period, the medium was replaced every 24 hours.

TABLE 1

| Composition of endoderm differentiation medium 1 (DE medium 1) (12 mℓ) |
| --- |
| RPMI-1640 containing 0.1% BSA and 1% B27 supplement |
| 50 ng/mℓ Activin A (ActA) |
| 0.5 mM sodium butyrate |
| 3 μM CHIR99021 |

TABLE 2

| Composition of endoderm differentiation medium 2 (DE medium 2) |
| --- |
| RPMI-1640 containing 0.1% BSA and 1% B27 supplement |
| 50 ng/mℓ Activin A (ActA) |
| 0.1 mM sodium butyrate |

<1-3> Differentiation of Definitive Endoderm (DE) Cells into Hepatic Endoderm (HE) Cells (Day −4 to Day 0)

To differentiate the definitive endoderm cells differentiated in Examples <1-2> into hepatic endoderm cells, the following procedure was performed.

Specifically, 12 mℓ of the hepatic endoderm differentiation medium (HE medium) with the composition of Table 3 below was made to 37° C., and then the medium was added to the plate containing the definitive endoderm cells differentiated in Example <1-2> (1 mℓ per well), followed by culture in a 37° C., 5% $CO_2$ incubator for 4 days. During the culture period, the medium was replaced every 24 hours. After completion of the differentiation, EpCAM-positive cells in some cells were analyzed under the same conditions and methods as the flow cytometry described in Experimental Example 1 below, and if the EpCAM-positive cells were more than 95%, the next step, the hepatic endoderm organoid production step, was performed.

TABLE 3

| Composition of hepatic endoderm differentiation medium (HE medium) (12 mℓ) |
| --- |
| RPMI-1640 containing 0.1% BSA and 1% B27 supplement |
| 50 ng/mℓ BMP 4 |
| 10 μM SB431542 |

<1-4> Production of Hepatic Endoderm Organoids from Hepatic Endoderm Cells (Day 0 to Day 14)

After the differentiation was completed, the medium was removed from the hepatic endoderm cells prepared in Example <1-3>. The cells were washed once with $Ca^{2+}$/$Mg^{2+}$-free DPBS, and 500 μℓ of accutase was added to each well, followed by culture at 37° C. for 10 minutes. The cells separated into single cells were transferred to a 15 mℓ conical tube containing 10 mℓ of an organoid basal medium (advanced DMEM/F12 containing 10 mM HEPES, 1% GlutaMAX, 100 U/mℓ penicillin-streptomycin, and 0.1% BSA), centrifuged at 1200 rpm for 3 minutes, and the obtained supernatant was removed. The cell pellet was resuspended in 1 mℓ of a cold hepatic endoderm production medium for D-HEO or S-HEO (Table 4 or 5), transferred to a 1.5 mℓ tube for cell counting, and hepatic endoderm organoids were produced in the form of droplet or in suspension as follows.

<1-4-1> Production of Droplet-Shaped Hepatic Endoderm Organoid (D-HEO) (Generation Stage)

15,000 hepatic endoderm cells in 100 μℓ of a cold hepatic endoderm organoid production medium with the composition of Table 4 were prepared in a 1.5 mℓ tube and placed on ice. 200 μℓ of Matrigel GFR (growth factor reduced) stock solution was added to the prepared cells and mixed by pipetting to avoid the formation of bubbles. A mixture of 100 μℓ of Matrigel and hepatic endoderm cells in a 24-well or 4-well plate was made at a cell density of 5000 cells/droplet and dispensed in the center of the plate to form a dome structure and solidified at 37° C. for 10 minutes. Then, 700 to 1000 μℓ of a 37° C. hepatic endoderm organoid production medium at was added to each well of the plate and cultured for 14 days in a 37° C., 5% $CO_2$ incubator.

TABLE 4

Composition of hepatic endoderm organoid production medium (GE medium) for D-HEO Advanced DMEM/F12 containing 10 mM HEPES, 1% GlutaMAX, 100 U/mℓ penicillin-streptomycin, 0.1% BSA, 1% B27 supplement minus vitamin A, and 1% N2 supplement
50 ng/mℓ FGF 10 (fibroblast growth factor 10)
25 ng/mℓ HGF (hepatocyte growth factor)
10 mM Nicotinamide
10 nM [Leu15]-Gastrin I human
1.25 mM N-acetyl-L-cysteine
5 μm A83-01
10 μM Forskolin
3 μM CHIR99021

<1-4-2> Production of Suspension-Type Hepatic Endoderm Organoid (S-HEO) (Generation Stage)

A hepatic endoderm organoid production medium with the composition of Table 5 was pre-dispensed in a 24-well ultra low attachment plate (0.5 mℓ per well). The medium was always kept on ice to prevent the Matrigel from solidifying. After adding 10,000 hepatic endoderm cells to each well of the plate, the cells were cultured for 14 days in a 37° C., 5% $CO_2$ incubator. At this time, the pieces were spread evenly and cultured to prevent the organoids from clumping and growing. The medium was replaced every 3 days of culture. To replace the medium, all medium containing organoids cultured in suspension was collected in a 1.5 mℓ tube using a 1000 P pipette and centrifuged at 1200 rpm for 3 minutes to remove the supernatant. The cell pellet was resuspended in 0.5 mℓ of a new hepatic endoderm expansion medium with the composition of Table 5, and the cells were seeded in a plate, followed by culture in a 37° C., 5% $CO_2$ incubator for 3 days.

TABLE 5

Composition of hepatic endoderm organoid production medium (GE medium) for S-HEO Advanced DMEM/F12 containing 10 mM HEPES, 1% GlutaMAX, 100 U/mℓ penicillin-streptomycin, 0.1% BSA, 1% B27 supplement minus vitamin A, and 1% N2 supplement
50 ng/mℓ FGF 10 (fibroblast growth factor 10)
25 ng/mℓ HGF (hepatocyte growth factor)
10 mM Nicotinamide
10 nM [Leu15]-Gastrin I human
1.25 mM N-acetyl-L-cysteine
5 μM A83-01
10 μM Forskolin
3 μM CHIR99021
*0.5 mg/mℓ Matrigel GFR (growth factor reduced)

*Added when producing hepatic endoderm organoids (S-HEO) by suspension culture

<1-5> Expansion Stage of Hepatic Endoderm Organoid (Days 14 to 19)

Figure 2:
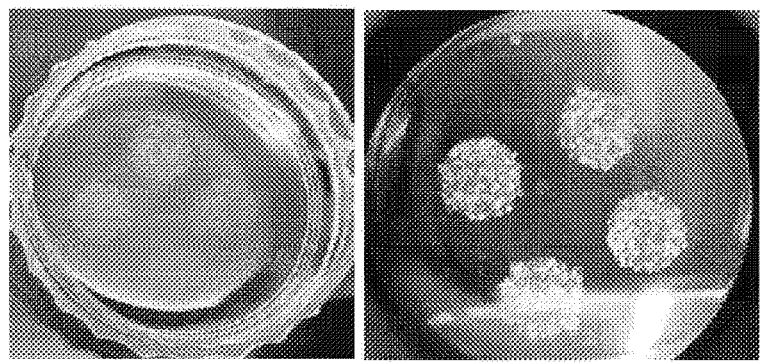
FIG. 2 is a set of photographs showing the droplet-shaped hepatic endoderm organoid (D-HEO).
Figure 3:
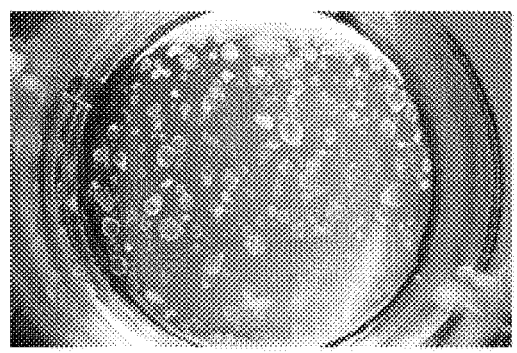
FIG. 3 is a photograph showing the suspension-type hepatic endoderm organoid (S-HEO).

The hepatic endoderm organoids prepared in Examples <1-4-1> and <1-4-2> were further cultured for 5 days in a medium having the composition of Table 4 or Table 5, respectively, to finally construct droplet-shaped hepatic endoderm organoids (D-HEO) (FIG. 2) and suspension-type hepatic endoderm organoids (S-HEO) (FIG. 3).

<1-6> Freezing and Thawing of Hepatic Endoderm Organoids

<1-6-1> Freezing of Hepatic Endoderm Organoids

The droplet-shaped hepatic endoderm organoids (D-HEO) were taken out of the incubator and pipetted with a 1000 P pipette to break the dome-shaped Matrigel containing the organoids, and then collected in a 1.5 mℓ tube.

The suspension-type hepatic endoderm organoids (S-HEO) were taken out of the incubator and pipetted with a 1000 P pipette to collect all of the organoids including the medium in the wells in a 1.5 mℓ tube.

In order to separate the hepatic endoderm organoids and Matrigel, the tube was placed on ice for 30 minutes and centrifuged at a maximum speed of 5000 rpm to remove the supernatant. 200 μℓ of a cold hepatic endoderm organoid expansion medium for D-HEO or S-HEO was added thereto, and the organoids were fragmented by pipetting with a 200 P pipette. Then, centrifugation was performed at a maximum speed of 5000 rpm to remove the supernatant, and after adding 1 mℓ of cold DPBS without $Ca^{2+}$ and $Mg^{2+}$, centrifugation was performed at a maximum speed of 5000 rpm to remove the supernatant again. After resuspension with 1 to 1.5 mℓ of CryoStor CS10 (Stem cell Technologies), the cryoprotectant, and the suspension was dispensed into cryotubes (0.5 mℓ/tube). The cryotubes were placed in a freezing container, stored in a deep freezer for one day, and transferred to a $LN_2$ tank (nitrogen tank) the next day.

<1-6-2> Thawing of Hepatic Endoderm Organoids

One cryotube was taken out of the $LN_2$ tank and thawed in a 37° C. water bath, and when it was half melted, it was taken out of the water bath and transferred to a 15 mℓ conical tube containing 10 mℓ of an organoid basal medium (advanced DMEM/F12 containing 10 mM HEPES, 1% GlutaMAX, 100 U/mℓ penicillin-streptomycin, and 0.1% BSA) prepared in advance and centrifuged at 1000 rpm for 3 minutes to remove the supernatant.

In the case of the droplet-shaped hepatic endoderm organoids (D-HEO), the organoid pellet was resuspended in 100 µℓ of a cold hepatic endoderm organoid expansion medium (Table 6), and then 200 µℓ of Matrigel GFR stock solution was added, followed by mixing. Thereafter, 100 µℓ of a mixture of the hepatic endoderm organoids and Matrigel was dispensed in the center of each well of a new 24-well plate to form a dome shape and solidified at 37° C. for 10 minutes. 700 to 1000 µℓ of a hepatic endoderm organoid expansion medium containing 20 µM Y27632 (Table 6) at 37° C. was added to each well and cultured in a 37° C., 5% $CO_2$ incubator for 3 to 4 days.

In the case of the suspension-type hepatic endoderm organoids (S-HEO), the organoid pellet was resuspended in 1 to 1.5 mℓ of a cold hepatic endoderm organoid expansion medium (Table 7), and then 0.5 mℓ of the suspension was added to each well of a new 24-well ultra-low attachment plate, followed by culture in a 37° C., 5% $CO_2$ incubator for 3 to 4 days. At this time, the pieces were spread evenly and cultured to prevent the organoids from clumping and growing. The medium was replaced every 3 days of culture.

Comparative Example 1: Preparation of In Vitro Hepatocyte Model

Primary human hepatocytes (PHH), HepG2 (liver cancer cell line), and 2D hPSC-derived hepatocyte-like cells (HLC) were cultured as follows.

As the primary human hepatocytes (PHH), BD Gentest™ Cryo Human Hepatocytes (BD Biosciences, Donor No. HFC 476) were cultured in a BD™ hepatocyte culture medium according to the manufacturer's instructions, and experiments were performed 24 hours later.

The liver cancer cell line HepG2 was maintained in MEM (HyClone) supplemented with 10% fetal bovine serum (Lonza) and 100 U/mℓ penicillin-streptomycin (Gibco).

In the case of the 2D hPSC-derived hepatocyte-like cells (HLC), hPSC-derived hepatic endoderm (HE) cells were further cultured in RPMI-1640 supplemented with 0.5 mg/mℓ BSA, 1×B27, 10 ng/mℓ FGF4, 10 ng/mℓ HGF, 10 ng/mℓ OSM, and 0.1 µM dexamethasone for 7 days.

EXAMPLE 2: PREPARATION OF LIVER ORGANOIDS (HUMAN HEPATIC ORGANOIDS, HHO)

The hepatic endoderm organoids constructed in Example <1-5> were subcultured and differentiated in a differentiation medium to prepare liver organoids (human hepatic organoids, hHOs) in the following manner.

<2-1> Subculture of Hepatic Endoderm Organoids (Days 19 to 24)

<2-1-1> Subculture of Droplet-Shaped Hepatic Endoderm Organoids (D-HEO)

The droplet-shaped hepatic endoderm organoids (D-HEO) constructed in Example <1-5> were pipetted with a 1000 P pipette to break the dome-shaped Matrigel containing the organoids, and then collected in a 1.5 mℓ tube. To separate the Matrigel and hepatic endoderm organoids, the tube was placed on ice for 30 minutes. The tube was centrifuged at a maximum speed of 5000 rpm to remove the supernatant, and 200 µℓ of a cold hepatic endodermal organoid expansion medium (EM) with the composition of Table 6 was added thereto, and pipetting was performed several times with a 200 P pipette to fragment organoids. Thereafter, the tube was centrifuged at a maximum speed of 5000 rpm to remove the supernatant, and 140 µℓ of a cold hepatic endodermal organoid expansion medium and 280 µℓ of Matrigel GFR stock solution were, followed by mixing. Then, 100 µℓ of a mixture of the hepatic endoderm organoids and Matrigel was dispensed in the center of each well of a new 24-well plate to form a dome shape and solidified at 37° C. for 10 minutes. 700 to 1000 µℓ of a hepatic endoderm organoid expansion medium at 37° C. was added to each well and cultured in a 37° C., 5% $CO_2$ incubator for 5 days.

TABLE 6

Composition of hepatic endoderm organoid expansion medium (EM medium) for D-HEO

Advanced DMEM/F12 containing 10 mM HEPES, 1% GlutaMAX, 100 U/mℓ penicillin-streptomycin, 0.1% BSA, 1% B27 supplement minus vitamin A, and 1% N2 supplement
25 ng/mℓ BMP7
50 ng/mℓ FGF 10 (fibroblast growth factor 10)
25 ng/mℓ HGF (hepatocyte growth factor)
10 mM Nicotinamide
10 nM [Leu$^{15}$]-Gastrin I human
1.25 mM N-acetyl-L-cysteine
5 µM A83-01
10 µM Forskolin
3 µM CHIR99021

<2-1-2> Subculture of Suspension-Type Hepatic Endoderm Organoids (S-HEO)

The suspension-type hepatic endoderm organoids (S-HEO) constructed in Example <1-5> were cultured in a hepatic endoderm organoid production medium with the composition of Table 7 supplemented with 25 ng/mℓ of BMP7 for 5 days. At this time, the medium was replaced once after 3 days of culture.

The suspension-type hepatic endoderm organoids (S-HEO) constructed in Example <1-5> were collected in a 1.5 mℓ tube using a 1000 P pipette, and the tube was placed on ice for 30 min to separate the hepatic endoderm organoids and Matrigel. The tube was centrifuged at a maximum speed of 5000 rpm to remove the supernatant. 200 µℓ of a cold hepatic endoderm organoid expansion medium (EM) with the composition of Table 7 was added thereto, and the organoids were fragmented by pipetting with a 200 P pipette. 0.5 mℓ of a hepatic endoderm organoid expansion medium with the composition of Table 7 was pre-dispensed into each well of a new 24-well ultra-low attattchment plate, and 66 µℓ of the fragmented hepatic endoderm organoid (S-HEO) suspension was dispensed into each well of the plate, followed by culture in a 37° C., 5% $CO_2$ incubator for 5 days. At this time, the pieces were spread evenly and cultured to prevent the organoids from clumping and growing. The medium was replaced every 3 days of culture. To replace the medium, all medium containing organoids cultured in suspension was collected in a 1.5 mℓ tube using a 1000 P pipette and centrifuged at 5000 rpm to remove the supernatant. The pellet was resuspended in 0.5 mℓ of a new hepatic endoderm expansion medium, and the cells were seeded in a plate.

TABLE 7

Composition of hepatic endoderm organoid expansion medium (EM) for S-HEO

Advanced DMEM/F12 containing 10 mM HEPES, 1% GlutaMAX, 100 U/mℓ penicillin-streptomycin, 0.1% BSA, 1% B27 supplement minus vitamin A, and 1% N2 supplement
25 ng/mℓ BMP7
50 ng/mℓ FGF 10 (fibroblast growth factor 10)
25 ng/mℓ HGF (hepatocyte growth factor)
10 mM Nicotinamide
10 nM [Leu$^{15}$]-Gastrin I human
1.25 mM N-acetyl-L-cysteine
5 µM A83-01
10 µM Forskolin
3 µM CHIR99021
*0.5 mg/mℓ Matrigel GFR (growth factor reduced)

*Added when producing hepatic endoderm organoids (S-HEO) by suspension culture

<2-2> Differentiation of Hepatic Endoderm Organoids into Liver Organoids (Days 24 to 39)

<2-2-1> Production of Droplet-Shaped Liver Organoids (D-HEO)

The droplet-shaped hepatic endoderm organoids subcultured in Example <2-1-1> were cultured for 15 days using a liver organoid differentiation medium with the composition of Table 8. At this time, the medium was replaced every 3 days of culture.

TABLE 8

Composition of liver organoid differentiation medium (DM)

Advanced DMEM/F12 containing 10 mM HEPES, 1% GlutaMAX, 100 U/mℓ penicillin-streptomycin, 0.1% BSA, and 1% B27 supplement minus vitamin t
25 ng/mℓ BMP7
100 ng/mℓ FGF19
25 ng/mℓ HGF
10 nM [Leu$^{15}$]-Gastrin I human
1.25 mM N-acetyl-L-cysteine
0.5 µM A83-01
1 µℓ DAPT
3 µM Dexamethasone <2-2-2> Production of Suspension-Type Liver Organoids (S-HO)

The suspension-type hepatic endoderm organoids subcultured in Example <2-1-2> were cultured for 15 days using a liver organoid differentiation medium with the composition of Table 9. At this time, the medium was replaced every 3 days of culture.

To replace the medium, all medium containing liver organoids cultured in suspension was collected in a 1.5 mℓ tube using a 1000 P pipette and centrifuged at 5000 rpm to remove the supernatant. The pellet was resuspended in 0.5 mℓ of a new hepatic organoid differentiation medium, and the cells were seeded in a plate.

TABLE 9

Composition of liver organoid differentiation medium (DM)

Advanced DMEM/F12 containing 10 mM HEPES, 1% GlutaMAX, 100 U/mℓ penicillin-streptomycin, 0.1% BSA, and 1% B27 supplement minus vitamin t
25 ng/mℓ BMP7

TABLE 9-continued

Composition of liver organoid differentiation medium (DM)

100 ng/mℓ FGF19
25 ng/mℓ HGF
10 nM [Leu$^{15}$]-Gastrin I human
1.25 mM N-acetyl-L-cysteine
0.5 µM A83-01
1 µℓ DAPT
3 µM Dexamethasone
*0.5 mg/mℓ Matrigel GFR (growth factor reduced)

*Added when producing hepatic endoderm organoids (S-HEO) by suspension culture

EXPERIMENTAL EXAMPLE 1: DETERMINATION OF MEDIUM COMPOSITION

To determine the composition of a hepatic endoderm organoid production medium, the following experiment was performed.

Specifically, except that cultured in a medium further containing R-Spondin 1, EGF, and Noggin in the medium composition of Table 4, hepatic endoderm organoids were differentiated by the same methods and conditions as in Examples <1-4-1>, and hepatic endoderm organoids were developed using a hepatic endoderm organoid expansion medium (EM) with the composition of Table 6. The number of cells expressing EpCAM in hepatic endoderm cells and hepatic endoderm organoids was analyzed by flow cytometry, and the expression levels of LGR5, a target protein of Wnt, and the target genes AXIN2 and EPHB2 were measured by RT-qPCR.

Flow cytometry was performed by dissociating cells or organoids with TypLE™ Express Enzyme (Thermo), fixing with 4% formaldehyde, and permeabilizing with 0.1% Triton X-100 in DPBS (HyClone™). The sample was incubated with a fluorescently labeled primary antibody on ice for 10 minutes and then washed twice with 0.5% BSA (Sigma) in DPBS. Flow cytometry was performed using CytoFLEX (Beckman Coulter), and data were processed using Kaluza analysis software (Beckman Coulter).

Quantitative reverse transcriptase polymerase chain reaction (RT-qPCR) using NucleoZOL Reagent (Macherey-Nagel, Duren, Germany) was performed to isolate total RNA from each sample and reverse transcribed using GoScript™ Reverse Transcription Mix (Promega). The qPCR was performed using GoTaq® qPCR Master Mix (Promega) in StepOnePlus Real-Time PCR system (Applied Biosystems, Foster City, CA, USA), and triplicate PCR amplifications were performed for each sample. PCR results were expressed as fold change relative to control cells after normalization with glyceraldehyde-3-phosphate dehydrogenase (GAPDH). The ΔCt (SΔCt) value was calculated as the difference between the Ct value obtained for GAPDH and the target gene. The ΔCt value of the control cell was used as the control ΔCt (SΔCt) value. The relative gene expression levels were determined using formula 2—(SΔCt−CΔCt).

Figure 4:
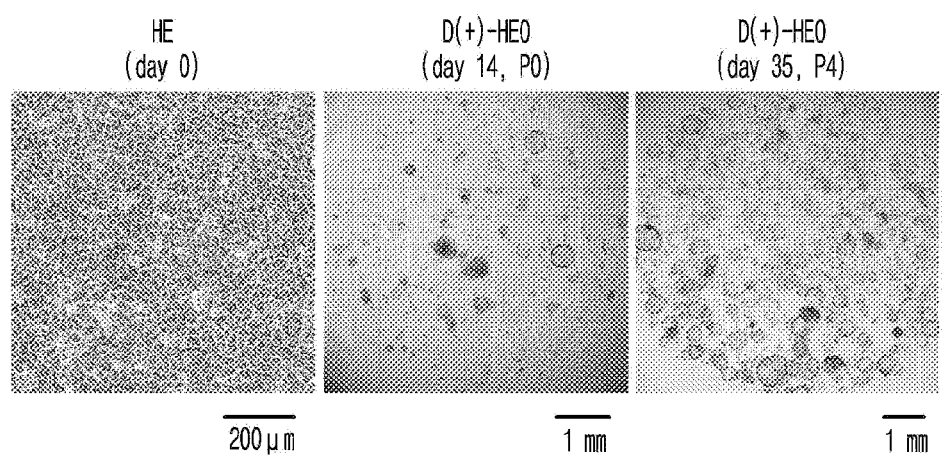
FIG. 4 is a set of photographs showing the hepatic endoderm (HE) cells and the hepatic endoderm organoid (D-HEO) differentiated from the hepatic endoderm cells.

As a result, as shown in FIG. 4, it was confirmed that hepatic endoderm organoids were formed after 14 days and maintained for more than 35 days. In addition, as shown in FIG. 5, EpCAM, a hepatic progenitor cell/stem cell marker, was expressed at high levels in hepatic endoderm cells and droplet-shaped hepatic endoderm organoids. On the other hand, LGR5, a target protein of Wnt that binds to R-spondin 1, was not detected on the cell surface, and the Wnt target genes AXIN2 and EPHB2 were significantly reduced in droplet-shaped hepatic endoderm organoids compared to hepatic endodermal cells.

These results suggest that Wnt signaling is not required for hepatic endoderm organoid development. Furthermore, since R-Spondin 1, EGF, and Noggin are known to be key factors in intestinal organoid production and expansion, and Noggin, a BMP antagonist, is known to inhibit liver specification, hepatic endoderm organoids were differentiated with a medium composition excluding R-Spondin 1, EGF, and Noggin.

EXPERIMENTAL EXAMPLE 2:
CHARACTERISTICS OF HEPATIC ENDODERM ORGANOIDS DIFFERENTIATED WITH MEDIUM COMPOSITION EXCLUDING R-SPONDIN 1, EGF, AND NOGGIN

<2-1> Measurement of Organoid Number and Organoid Formation Rate when Hepatic Endoderm Cells Were Differentiated into Hepatic Endoderm Organoids with Medium Composition Excluding R-Spondin 1, EGF, and Noggin In the case of differentiation into hepatic endoderm organoids by culturing in a medium further containing R-Spondin 1, EGF, and Noggin in the medium composition of Table 4, and differentiation into hepatic endoderm organoids under the same methods and conditions as in Example <1-4-1>, the number of organoids and the rate of organoid formation were measured.

Figure 6:
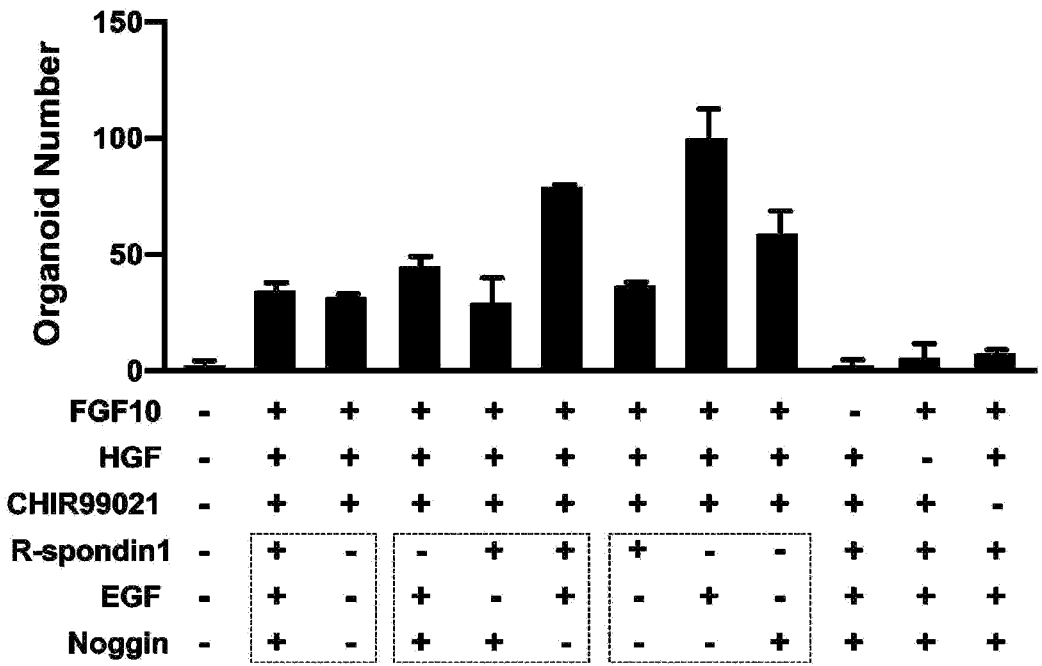
FIG. 6 is a graph showing that the number of organoids constructed in a hepatic endoderm organoid production medium without R-Spondin 1, Noggin, and EGF (RNE) was similar to the number of organoids constructed in a hepatic endoderm organoid production medium containing RNE when hepatic endoderm organoids were differentiated in a droplet shape.
Figure 7:
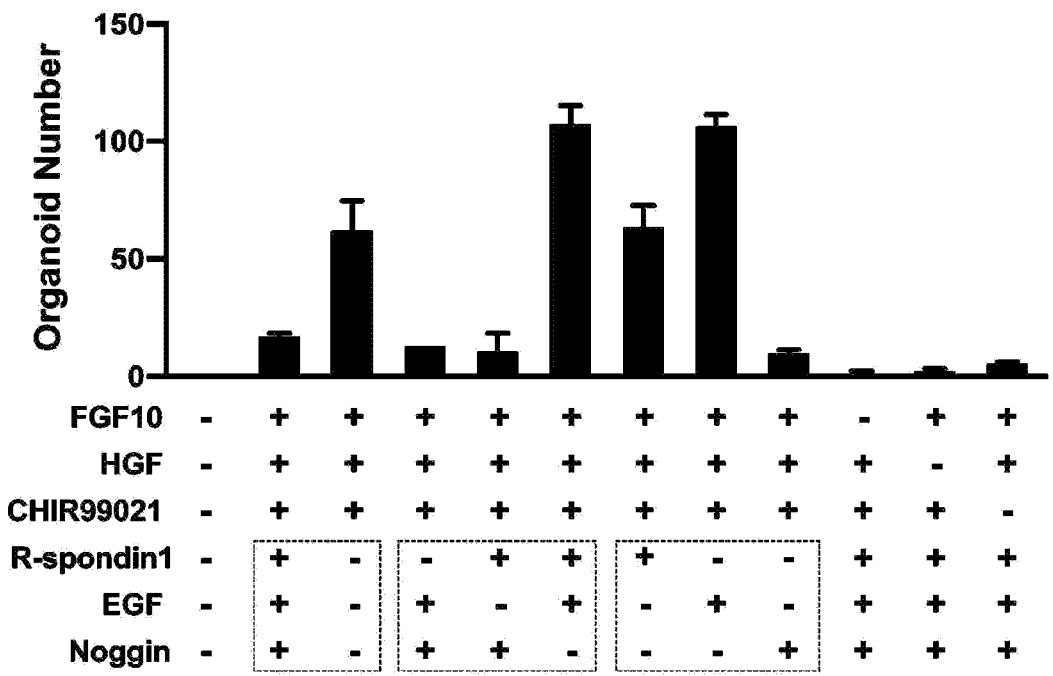
FIG. 7 is a graph showing that the number of organoids constructed in a hepatic endoderm organoid production medium without R-Spondin 1, Noggin, and EGF (RNE) was significantly increased compared to the number of organoids constructed in a hepatic endoderm organoid production medium containing RNE when hepatic endoderm organoids were differentiated in a droplet shape.
Figure 8:
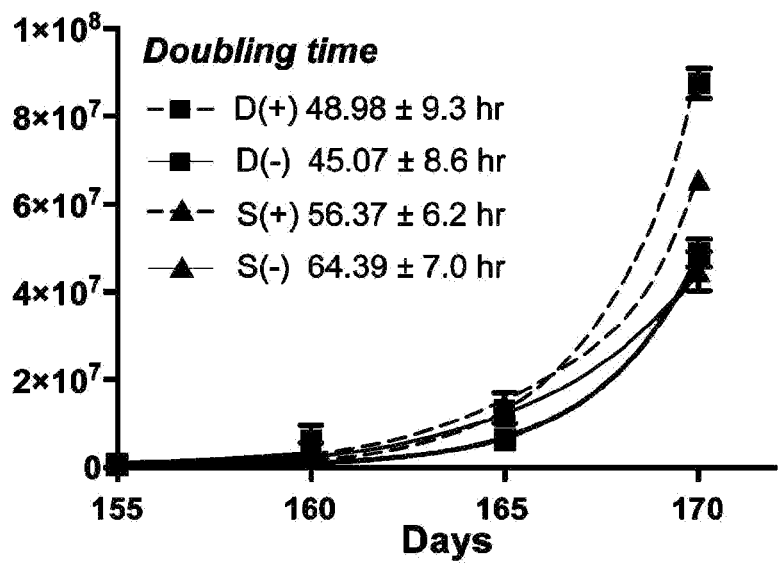
FIG. 8 is a set of graphs showing that the formation rate of a suspension-type hepatic endoderm organoid (S-HEO) is 3.5 times higher when cultured in a medium without RNE than when cultured in a medium containing RNE.
Figure 8:
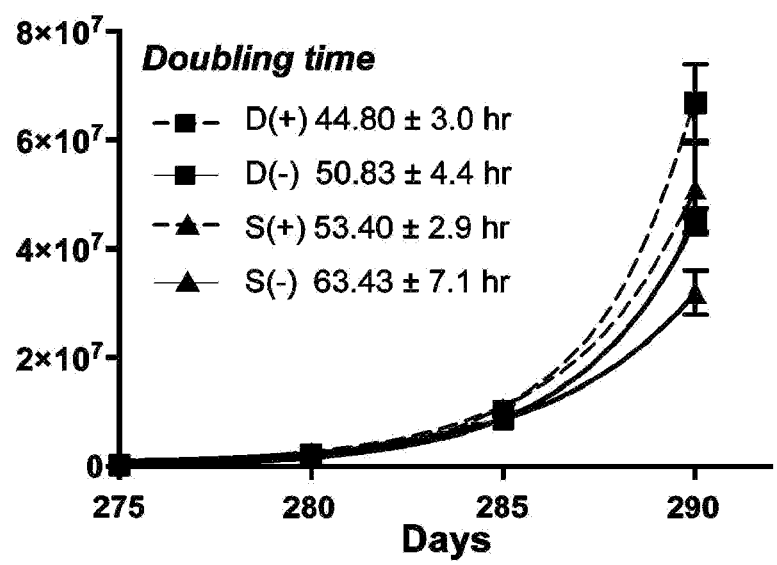

As a result, as shown in FIG. 6, in the case of differentiation into droplet-shaped hepatic endoderm organoids, the number of organoids produced in the hepatic endoderm organoid production medium without R-Spondin 1, Noggin and EGF (RNE) was similar to the number of organoids produced in the hepatic endoderm organoid production medium containing RNE. As shown in FIG. 7, in the case of differentiation into suspension-type hepatic endoderm organoids, the number of organoids produced in the hepatic endoderm organoid production medium without R-Spondin 1, Noggin and EGF (RNE) was significantly increased compared to the number of organoids produced in the hepatic endoderm organoid production medium containing RNE. In addition, as shown in FIG. 8, when cultured in a medium containing RNE, the formation rate of suspension-type hepatic endoderm organoids (S-HEO) was more than 3.5 times higher than when cultured in a medium without RNE.

<2-2> Cultivation of Differentiated Hepatic Endoderm Organoids at Expansion Stage with Medium Composition without R-Spondin 1 and EGF In the case of cultivation of droplet-shaped hepatic endoderm organoids in the hepatic endoderm organoid expansion medium containing R-Spondin 1 and EGF (RE) (D(+)-HEO), in the case of cultivation of droplet-shaped hepatic endoderm organoids in the hepatic endoderm organoid expansion medium without R-Spondin 1 and EGF (RE) (D(−)-HEO), in the case of cultivation of suspension-type hepatic endoderm organoids in the hepatic endoderm organoid expansion medium containing R-Spondin 1 and EGF (RE) (S(+)-HEO), and in the case of cultivation of suspension-type hepatic endoderm organoids in the hepatic endoderm organoid expansion medium without R-Spondin 1 and EGF (RNE) (S(−)-HEO), the proliferative capacity of the hepatic endoderm organoids and the expression of the hepatic progenitor cell markers were measured and transcriptome analysis was performed.

<2-3> Confirmation of Proliferative Capacity of Hepatic Endoderm Organoids Differentiated under Various Conditions and Expression of Hepatic Progenitor Cell Markers In the hepatic endoderm organoids cultured under the four conditions of D(+)-HEO, D(−)-HEO, S(+)-HEO and S(−)-HEO, the organoid structure, the presence of proliferating cells, and the expression of SOX9 and EpCAM, the hepatic endoderm cell markers, were investigated as follows.

Specifically, the hepatic endoderm organoids differentiated under the four conditions were imaged by bright-field microscopy, and the paraffin-embedded sections of the hepatic endoderm organoids differentiated under each condition were stained with Hematoxylin & Eosin (H & E).

For BrdU staining, hepatic endoderm organoids (hHEO) were treated with 10 pM bromo-deoxyuridine (BrdU) labeling solution (Molecular Probes, Eugene, OR, USA) and cultured in a 37° C., 5% $CO_2$ incubator for 48 hours. Hepatic endoderm organoids (hHEO) were isolated, fixed, permeabilized, denatured with 1.2 M HCl, and stained with BrdU monoclonal antibody and Alexa Flour 488 (Invitrogen), followed by DAPI staining. Images were observed using an Olympus FV3000 confocal microscope.

For immunofluorescence of the paraffin-embedded sections, organoids were separated using cell recovery solution (Corning) to remove Matrigel, fixed in 4% formaldehyde overnight at 4° C., and then embedded in paraffin blocks. The sections were cut and hydrated, and boiled in sodium citrate buffer (pH 6.0) for antigen recovery. The samples were permeabilized, blocked with 5% normal serum (Jackson ImmunoResearch), incubated overnight at 4° C. with each primary antibody, and labeled with a fluorescein-conjugated secondary antibody for 1 hour. Nuclei were stained with 4'-6-diamidino-2-phenylindole (DAPI; Sigma-Aldrich) and mounted with ProLong™ Glass Antifade Mountant (Thermo). Images were taken with a Zeiss LSM 800 and an Olympus FV3000 confocal microscope.

Figure 9:
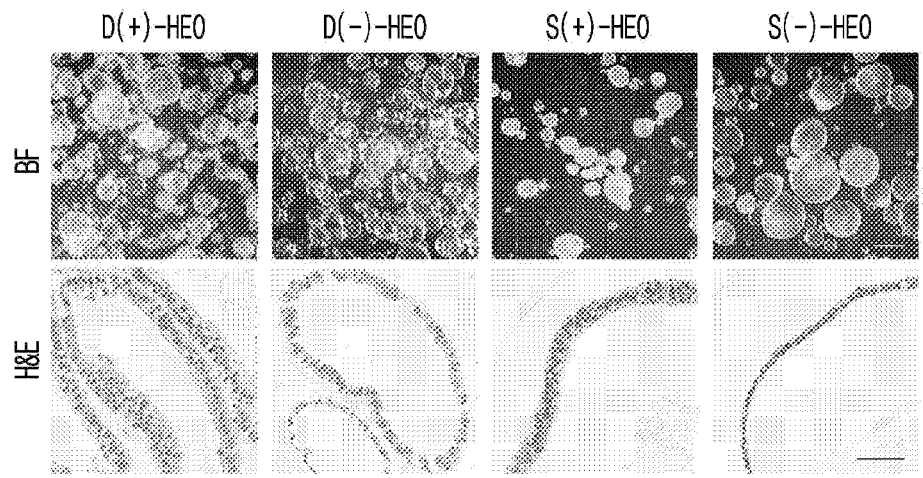
FIG. 9 is a set of photographs showing the structure of hepatic endoderm organoids cultured under four conditions, D(+)-HEO, D(−)-HEO, S(+)-HEO, and S(−)-HEO, confirmed by bright-field microscopy images and hematoxlin & eosin (H&E) staining.

As a result, as shown in FIG. 9, a multi-layer cystic structure was observed in D(+)-HEO and S(+)-HEO, and a single-layer cystic structure was observed in D(−)-HEO and S(−)-HEO. In addition, as shown in FIG. 10, in BrdU-stained images, proliferating cell populations were observed in the hepatic endoderm organoids under all conditions, and the hepatic progenitor cell markers SOX9, CK19, and EpCAM were also expressed.

<2-4> Transcriptome Analysis of Hepatic Endoderm Organoids Differentiated under Various Conditions Transcriptome analysis of the hepatic endoderm organoids cultured under the four conditions of D(+)-HEO, D(−)-HEO, S(+)-HEO, and S(−)-HEO was performed as follows.

Specifically, an mRNA library was constructed using a TruSeq Stranded mRNA LT Sample Prep Kit and then sequenced using an Illumina NovaSeq 6000 platform. The reads were aligned using HISAT2 (v2.1.0) (Kim et al., 2019) and assembled using StringTie (v1.3.4). The read counts were normalized to the trimmed average of M-values (TMM) using the edgeR (v3.26.8) R package. Highly variable genes and major components were calculated using the var and prcomp functions in the stats (v3.6.1) R package, respectively. Gene ontology and KEGG pathway analyses were performed using DAVID (Huang da et al., 2009a, b). Gene set enrichment analysis (GSEA) was performed using GSEA software (v4.0.3) with feature gene sets of MSigDB (v7.0) (Mootha et al., 2003).

Figure 11:
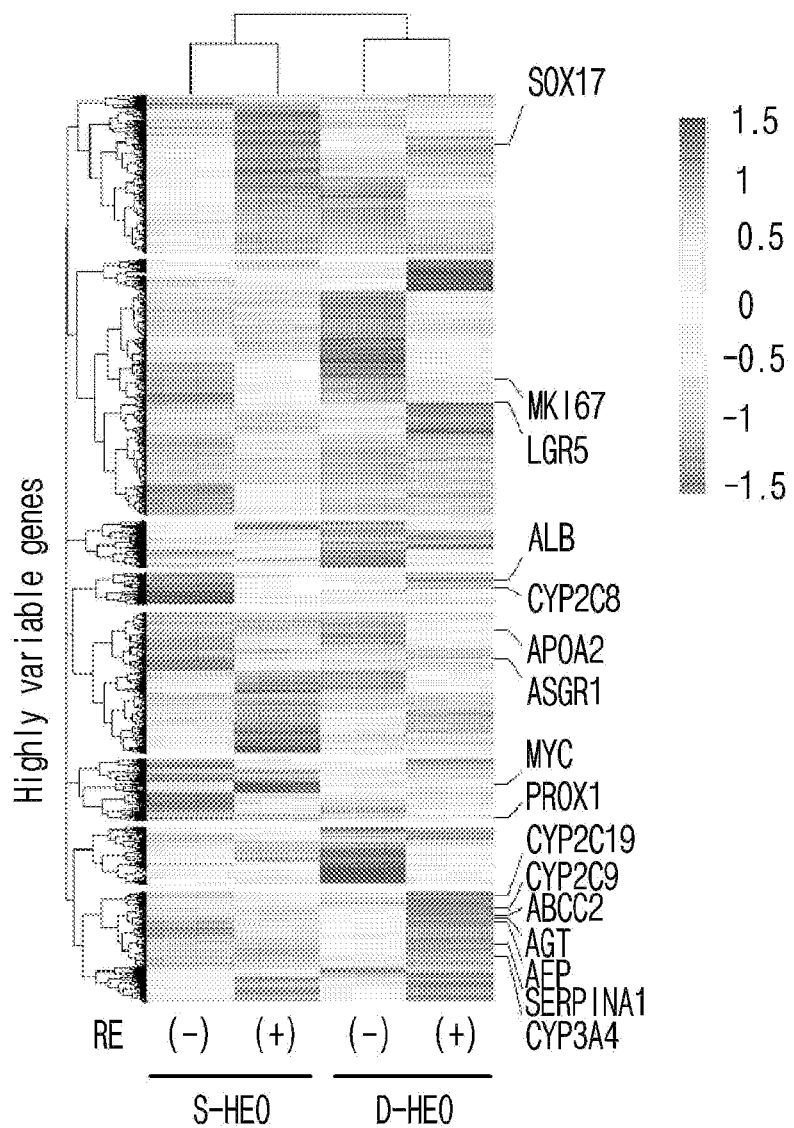
FIG. 11 is a diagram showing the genes differentially expressed in hepatic endoderm organoids cultured under four conditions, D(+)-HEO, D(−)-HEO, S(+)-HEO, and S(−)-HEO.

As a result, as shown in FIG. 11, the difference in culture conditions (droplet or suspension) was a condition that showed a greater difference in the differentially expressed genes than the treatment of R-spondin 1 and EGF. In the case of culturing droplet-shaped hepatic endoderm organoids, the expression of genes involved in organoid proliferation was high, and in the case of culturing suspension-type hepatic endoderm organoids, the expression of genes involved in organoid differentiation was high.

The above results suggest that the hepatic endoderm cells differentiated from human induced pluripotent stem cells can produce hepatic endoderm organoids by culture in a medium without RNE, and that the hepatic endoderm organoids can be maintained as hepatic endoderm cells at the expansion stage without R-Spondin 1 and EGF.

EXPERIMENTAL EXAMPLE 3: EXPRESSION OF LIVER MARKER GENES AFTER DIFFERENTIATION OF LIVER ORGANOIDS UNDER VARIOUS CONDITIONS

Figure 12:
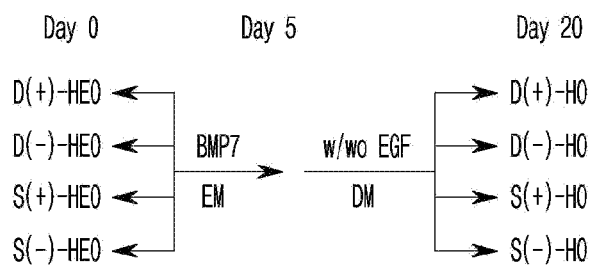
FIG. 12 is a schematic diagram showing the process of differentiating liver organoids from hepatic endoderm organoids.

<3-1> Expression Changes of Major Liver Genes when Hepatic Endoderm Organoids were Differentiated into Liver Organoids in Culture Medium with or without EGF Hepatic endoderm organoids cultured under the four conditions of D(+)-HEO, D(−)-HEO, S(+)-HEO, and S(−)-HEO were differentiated into liver organoids using the same methods and conditions as in Example <2-2> in a culture medium with or without EGF having the composition of Table 8 or 9 (FIG. 12), and the expression of major liver genes was measured.

Specifically, changes in the expression of major liver genes, including ALB, AAT, HNF4A, TDO2, G6P, CYP2C9, CYP2C19, CYP3A4, and nuclear receptors such as FXR, and CYP450 genes, were confirmed by the same methods and conditions as the RT-qPCR described in Experimental Example 1.

Figure 13A:
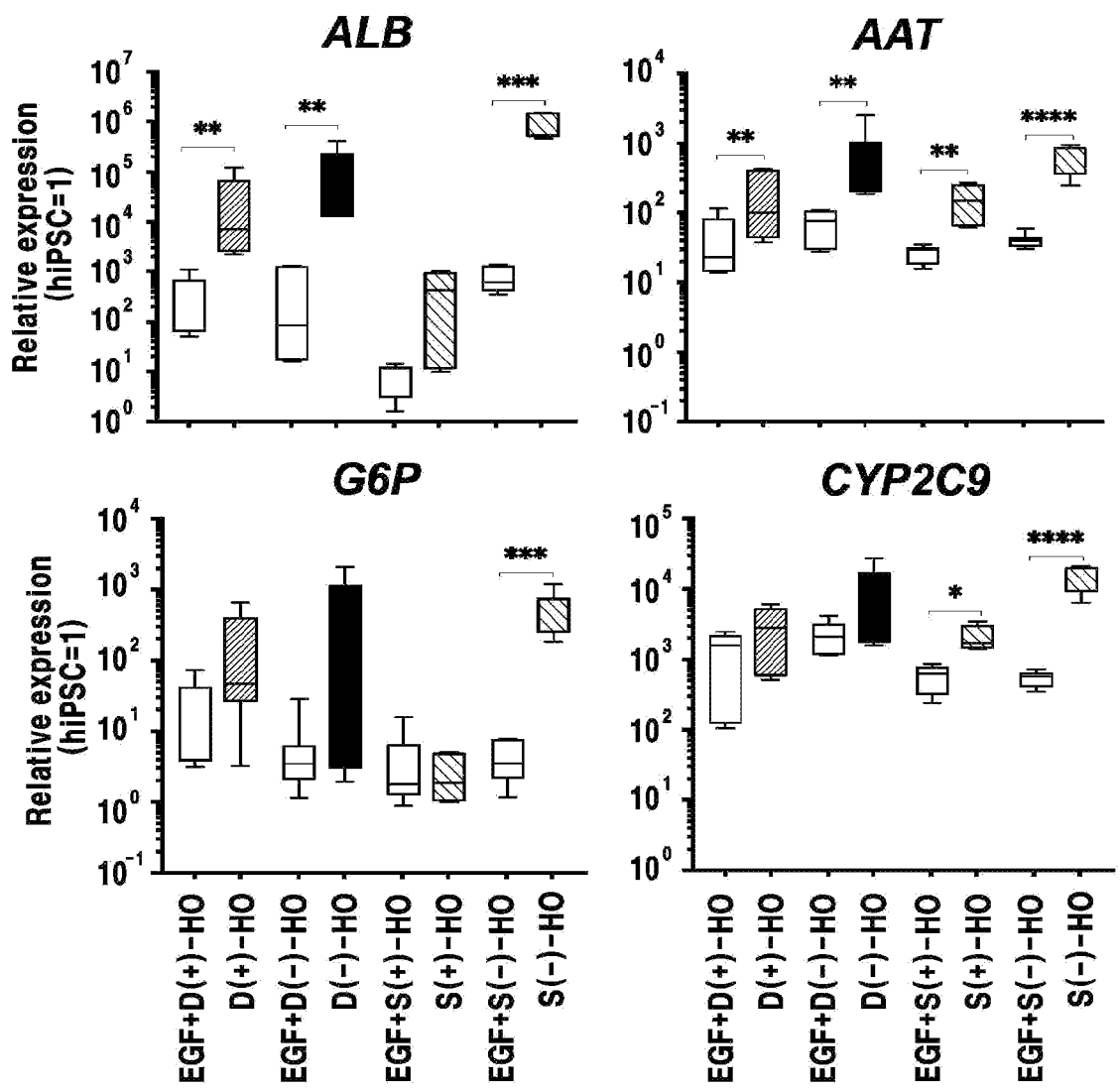
FIGS. 13a and 13b are graphs showing that the expression of major liver genes increased when liver organoids were differentiated in a culture medium without EGF.
Figure 13B:
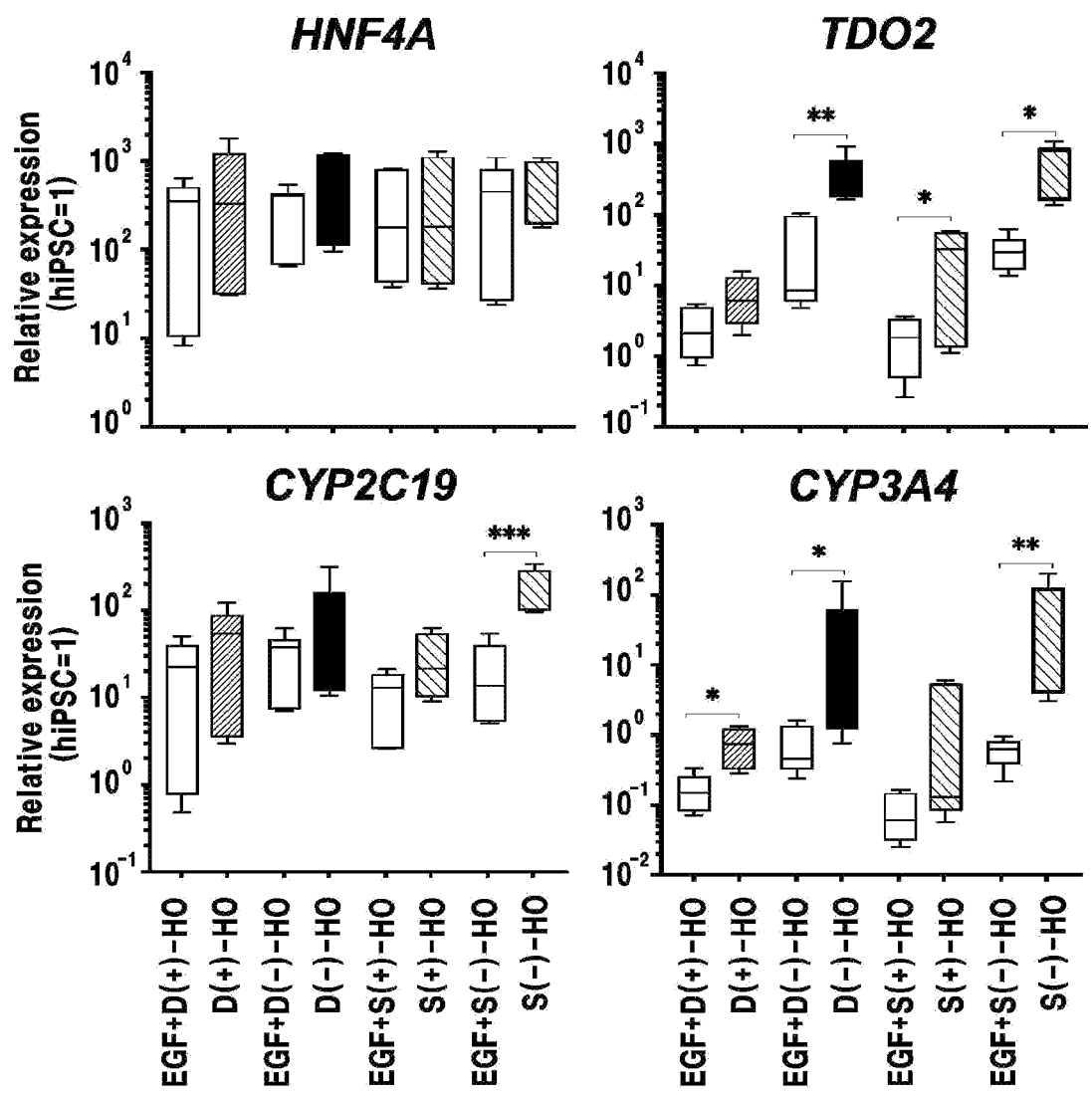

As a result, as shown in FIGS. 13a and 13b, during differentiation into liver organoids, the expression of major liver genes was increased when liver organoids were differentiated in a culture medium without EGF. Therefore, hepatic endoderm organoids were differentiated into liver organoids in each culture condition using a liver organoid differentiation medium without EGF.

<3-2> Confirmation of Structure of Liver Organoids Differentiated under Various Conditions and Confirmation of Liver Marker Gene Expression The liver organoids differentiated under the four conditions were subjected to bright-field imaging, H&E staining, and immunostaining using the same methods and conditions as those described in Example <2-3> to confirm the structure of the liver organoids. RT-qPCR was performed to confirm the expression of liver marker genes at the transcriptional level using the same methods and conditions as described in Experimental Example 1, and flow cytometry was performed to confirm the number of cells expressing ALB (albumin).

Figure 14:
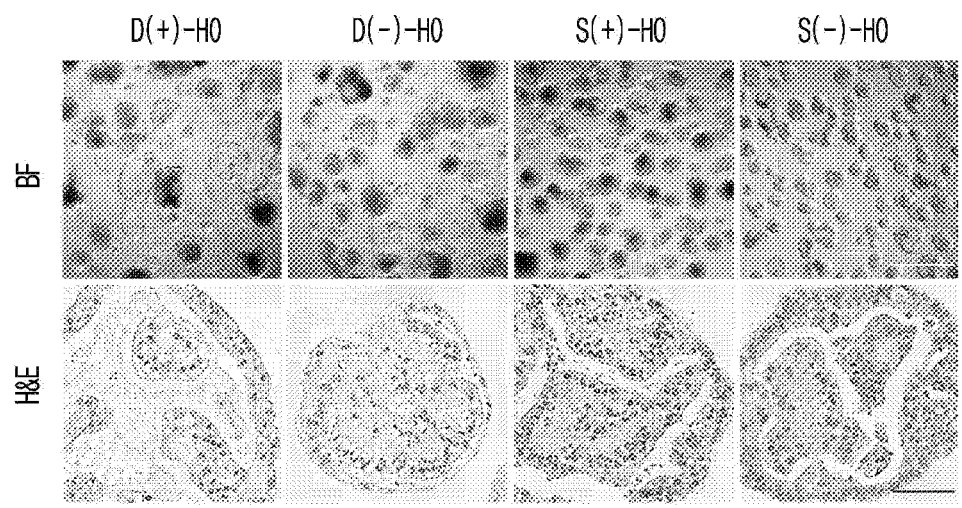
FIG. 14 is a set of photographs showing the structure of liver organoids cultured under four conditions, D(+)-HO, D(−)-HO, S(+)-HO, and S(−)-HO, confirmed by bright-field microscopy images and hematoxylin & eosin (H&E) staining.
Figure 16A:
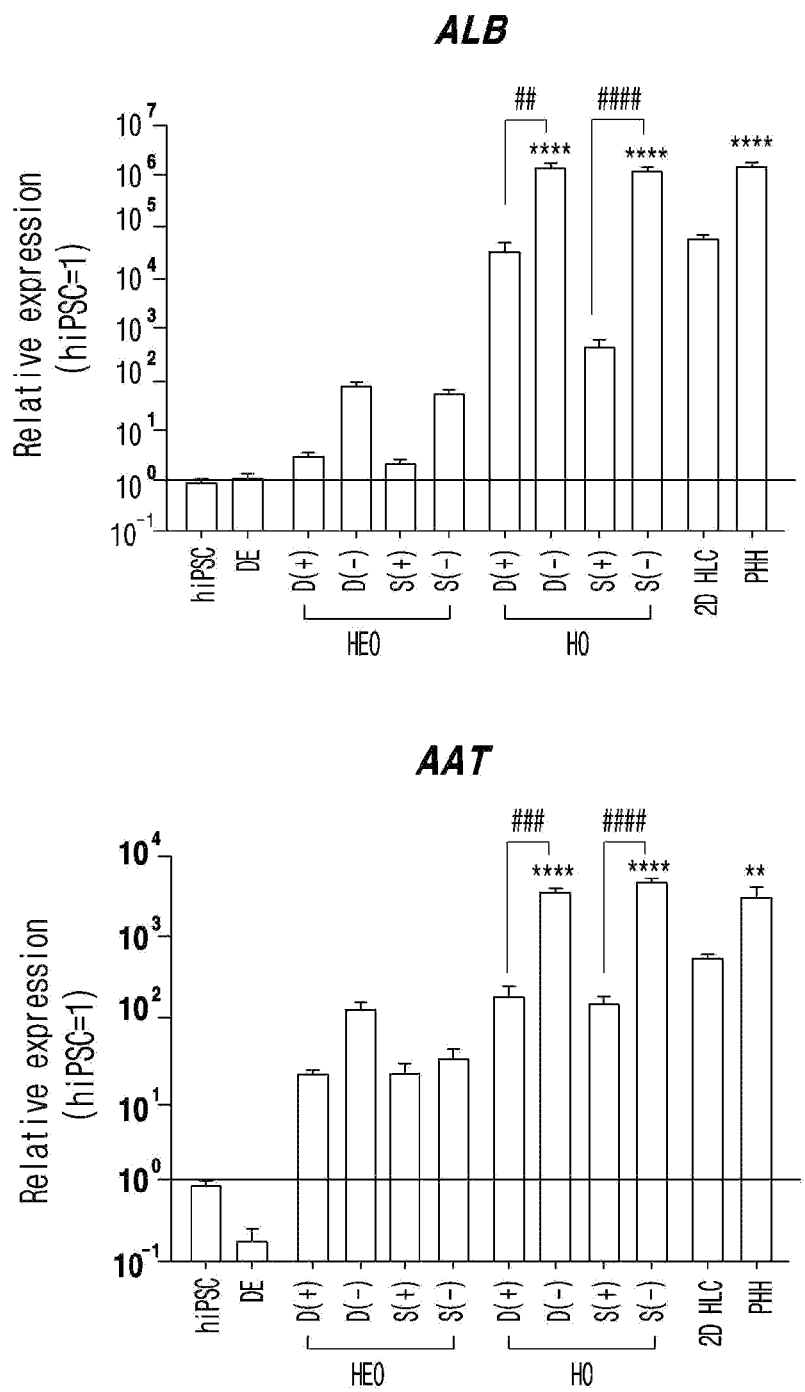
FIG. 16 are graphs showing the expression levels of the liver markers ALB, AAT, TDO2, HNF4A, G6P, and CYP3A4 in liver organoids cultured under four conditions, D(+)-HO, D(−)-HO, S(+)-HO, and S(−)-HO, confirming that the expression of the liver markers is higher in D(−)-HO and S(−)-HO.
Figure 16B:
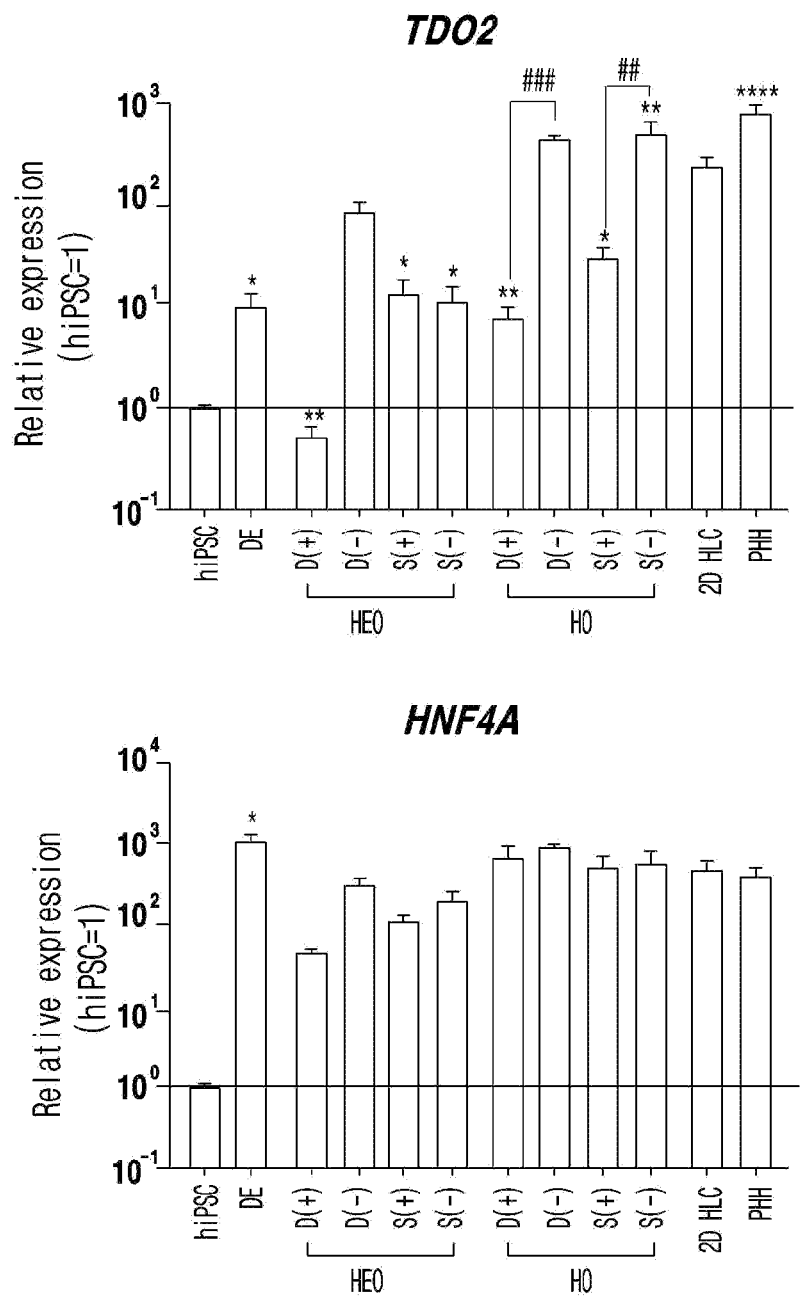
Figure 16C:
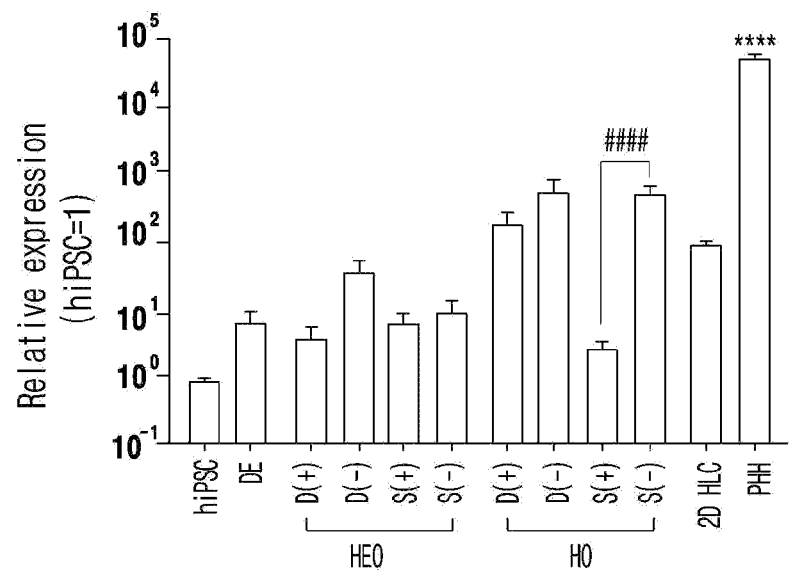
Figure 16C:
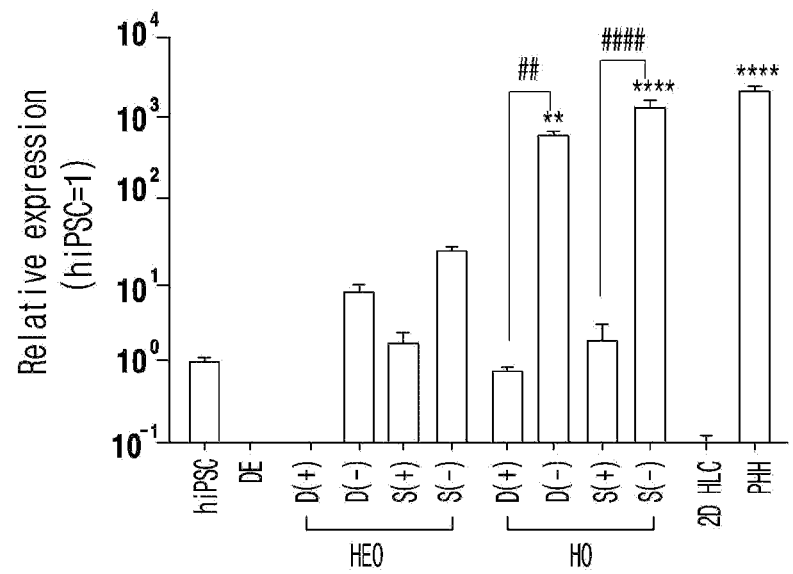

As a result, as shown in FIG. 14, the hepatic endoderm organoids self-organized into a contracted spherical shape after differentiation and showed a lumen inside the organoids under all four conditions. Under the conditions of S(+)-HO and S(−)-HO, liver organoids were formed more uniformly than under the conditions of D(+)-HO and D(−)-HO. It was confirmed that the expression of liver markers under the conditions of D(−)-HO and S(−)-HO was superior to that under the conditions of D(+)- and S(+)-HO at the protein level (FIG. 15) and transcriptional level (FIGS. 16a, 16b and 16c).

Figure 17:
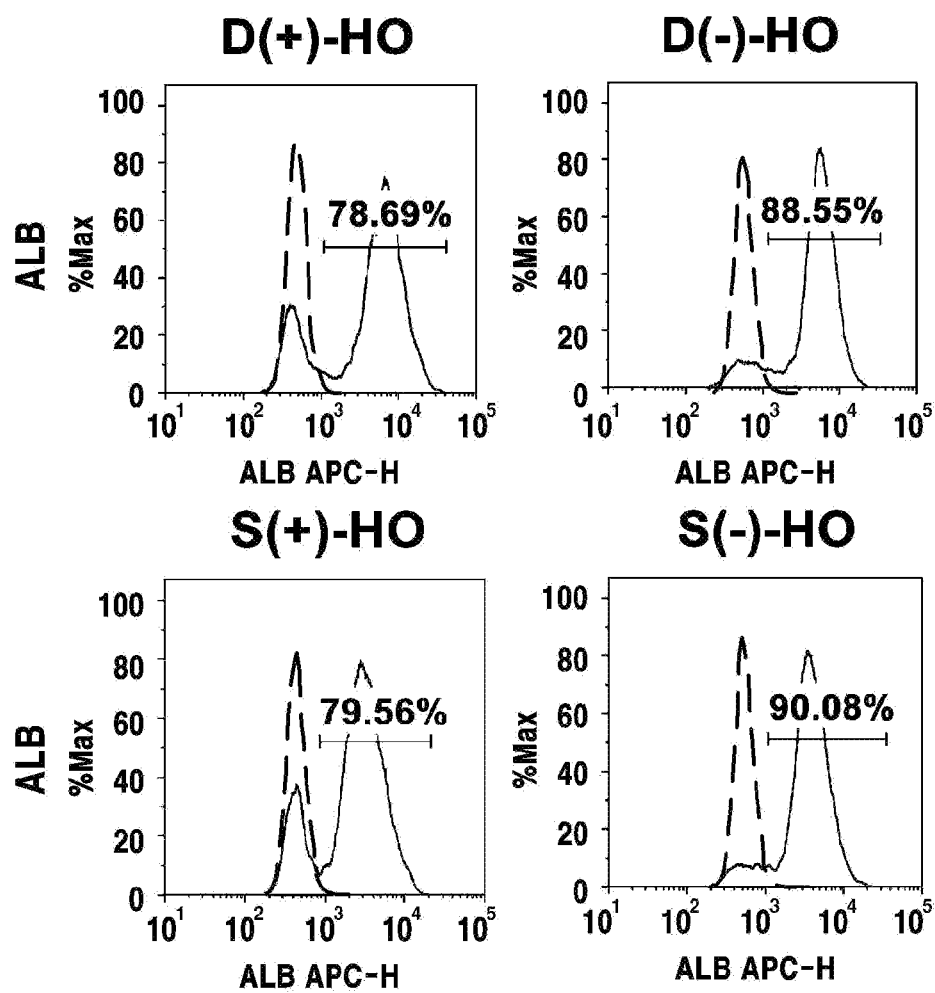
FIG. 17 is a set of graphs showing the results of counting the number of cells expressing ALB (albumin) in liver organoids cultured under four conditions, D(+)-HO, D(−)-HO, S(+)-HO, and S(−)-HO.

In addition, as shown in FIG. 17, as a result of counting the number of cells expressing ALB (albumin) by performing flow cytometry, it was confirmed that R-Spondin 1 and EGF had a negative effect on ALB expression. As shown in FIG. 18, it was confirmed that the expression of ALB (albumin), AAT (alpha 1-antitrypsin), and ApoA1 (apolipoprotein A1) was increased under the conditions of D(−)-HO and S(−)-HO compared to the conditions of D(+)-HO and S(+) -HO.

Therefore, these results suggest that the absence of R-Spondin 1 and EGF at the expansion stage affected liver maturation in the process of differentiation into hepatic endoderm organoids, and that the removal of EGF from the culture medium during differentiation into liver organoids increased the maturation process of liver organoids by increasing the expression levels of liver and drug metabolism-related genes.

EXPERIMENTAL EXAMPLE 4: EXPRESSION OF DRUG METABOLISM ENZYMES AND DRUG TRANSPORTERS IN LIVER ORGANOIDS

<4-1> Confirmation of Structure of Liver Organoids and Expression of Drug Transporter-Related Genes In the liver, an ATP-binding cassette transporter (ABC transporter) plays an important role in the efflux of endogenous and exogenous substances by phase II conjugation with CYP450 enzyme. Accordingly, the structure of the liver organoids differentiated from the hepatic endoderm organoids was observed with a transmission electron microscope, and the expression of genes related to apical and basolateral drug transporters in the droplet-shaped liver organoids (D-HO) and suspension-type liver organoids (S-HO) prepared in Example 2, primary human hepatocytes (PHH), HepG2 (liver cancer cell line), and 2D hPSC-derived hepatocyte-like cells (2D HLC) prepared in Comparative Example 1 was confirmed using the same methods and conditions as described in Example 1.

Specifically, the transmission electron microscopy observation procedure is as follows. The liver organoids were fixed in 2% glutaraldehyde-paraformaldehyde in 0.1 M phosphate buffer (PB), pH 7.4 for 12 hours and washed in 0.1 M phosphate buffer. After fixation for 2 hours with 1% $OsO_4$ dissolved in 0.1 M PB, the liver organoids were dehydrated with concentration gradient ethanol (50-100%) and infiltrated with propylene oxide. The specimens were embedded in the Poly/Bed 812 kit (Polysciences). It was embedded in pure fresh resin and polymerized for 24 hours in a 65° C. electron microscope oven (TD-700, DOSAKA, Japan). Sections about 200-250 nm thick were initially cut and stained with toluidine blue (Sigma-Aldrich) for light microscopy. 70 nm thin sections were double stained with 6% uranyl acetate (EMS, 22400, 20 minutes) and lead citrate (Fisher, 10 minutes) for counterstaining. The sections cut by LEICA EM UC-7 (Leica Microsystems, Austria) using a diamond knife (Diatome) were transferred onto copper and nickel grids, and all thin parts were observed under a transmission electron microscope (JEM-1011, JEOL, Japan) at an accelerating voltage of 80 kV.

Figure 19:
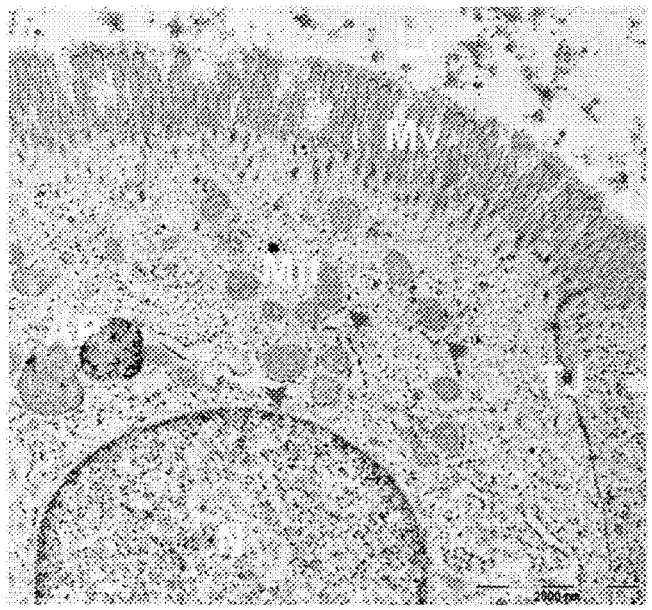
FIG. 19 is a set of photographs confirming that liver organoids cultured under D(−)-HO and S(−)-HO conditions exhibit microvilli structures (MV) and tight junction structures (TJ).
Figure 19:
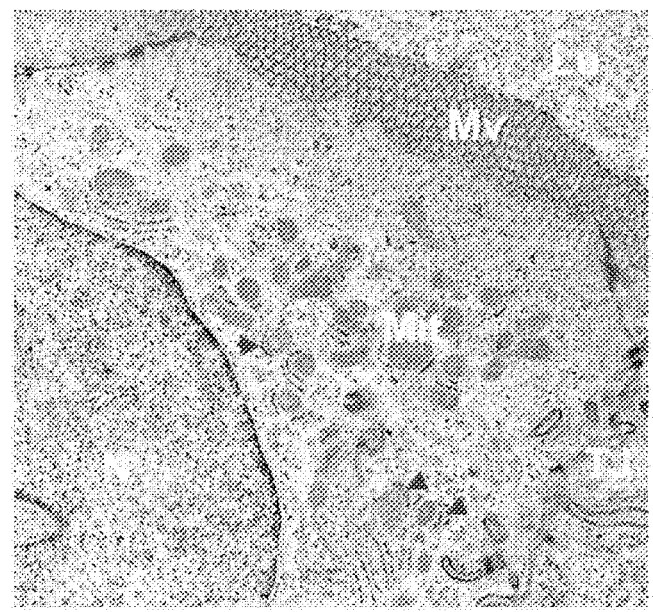
Figure 20:
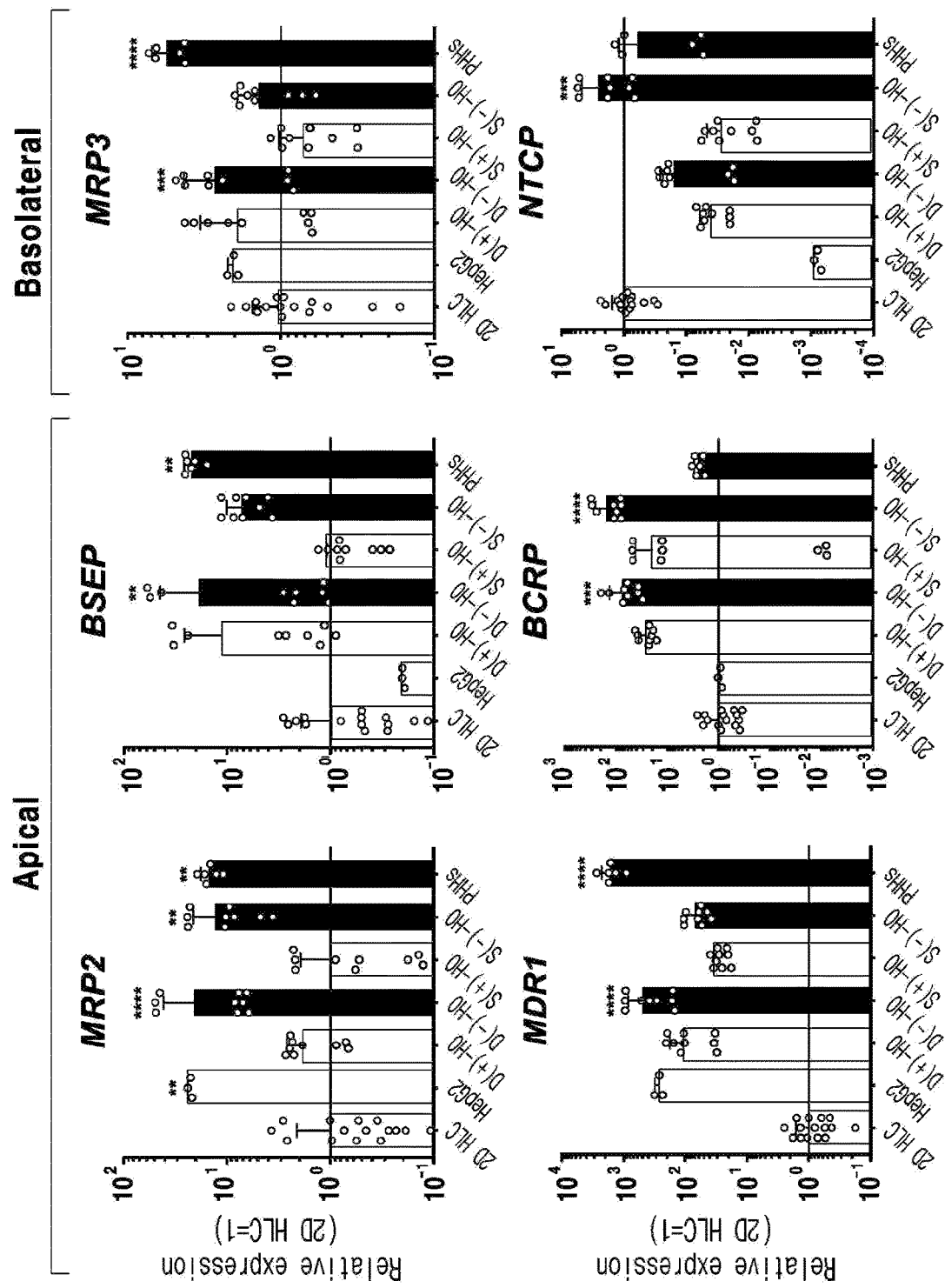
FIG. 20 is a set of graphs confirming that the expression of apical transporter genes such as MRP2, BSEP, MDR1, and BCRP in both D(−)-HO and S(−)-HO was higher than in primary human hepatocytes (PHH), liver cancer cell line (HepG2), and 2D hPSC-derived hepatocyte-like cells (2D HLC).

As a result, as shown in FIG. 19, the microvillous structures on the luminal side and tight junction structures were observed in the liver organoids. In addition, as shown in FIG. 20, transcriptional expression analysis of drug transporter-related genes between D(−)-HO, S(−)-HO, PHH, HepG2, and 2D HLC showed that both D(−)-HO and S(−)-HO had higher expression of apical drug transporters genes such as MRP2, BSEP, MDR1, and BCRP compared to 2D HLC. On the other hand, D(−)-HO and S(−)-HO showed significantly higher expression of MRP3 and NTCP, the respective basolateral drug transporter genes.

These results suggest that the apical side membrane with microvilli develops intensively in the liver organoids located in the luminal side membrane.

<4-2> Confirmation of Whether Apical Drug Transporter Genes are Expressed in Liver Organoids The expression of the apical drug transporters MRP2, BSEP, and MDR1 in the liver organoids and the expression changes upon administration of inhibitors of each gene were confirmed by fluorescence staining.

Specifically, the liver organoids were recovered on Matrigel and washed three times with DPBS. For CDFDA (5(6)-carboxy-2',7'-dichlorofluorescein diacetate) staining, the liver organoids treated with or without 2 mM probenecid for 3 hours were stained with 10 µM CDFDA (Sigma-Aldrich) for 15 minutes at 37° C., 5% $CO_2$. For CLF (Choyl-Lysyl-Fluorescein) and rhodamine 123 staining, the liver organoids treated with 4 µM CLF (Corning) or 10 µM rhodamine 123 (Invitrogen) for 15 minutes each for 24 hours with or without 10 µM ketoconazole were cultured for 1 hour. All samples were washed three times with DPBS, stained with Hoechst 33342, and observed under an Olympus FV3000 confocal microscope.

Figure 21:
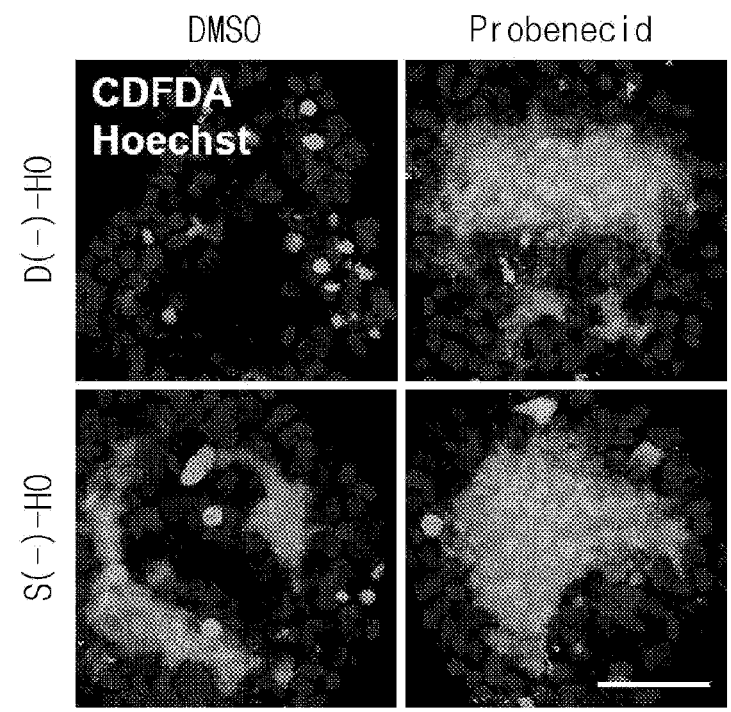
FIG. 21 is a set of photographs confirming the expression of MRP2 (stained with CDFDA), an apical drug transporter, in the apical membranes of D(−)-HO and S(−)-HO, and that each drug transporter-specific fluorescence was accumulated in the lumen of a liver organoid as a result of treatment with probenecid, an MRP2 inhibitor.
Figure 22:
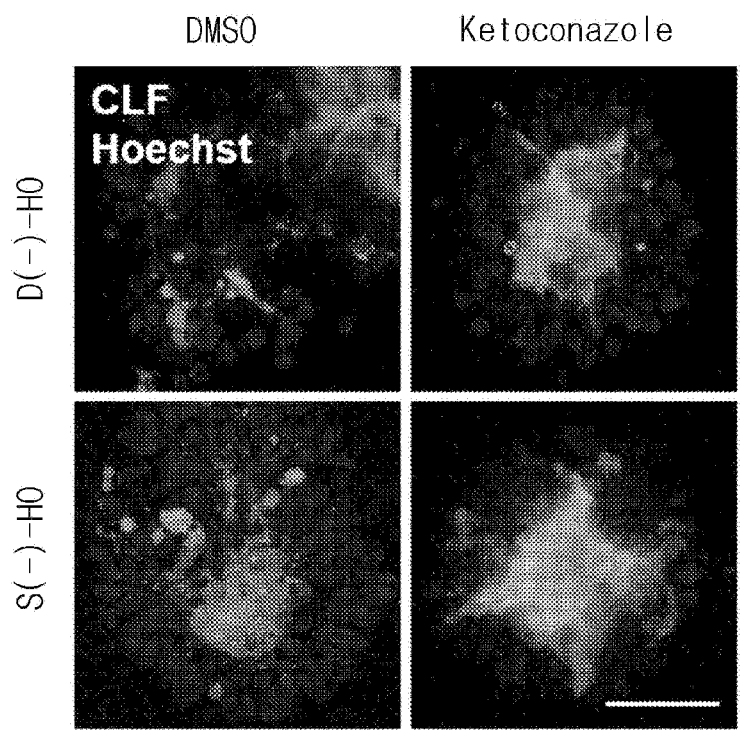
FIG. 22 is a set of photographs confirming the expression of MDR1 (stained with rhodamine 123), an apical drug transporter, in the apical membranes of D(−)-HO and S(−)-HO, and that each drug transporter-specific fluorescence was accumulated in the lumen of a liver organoid as a result of treatment with ketoconazole, an MDR1 inhibitor.
Figure 23:
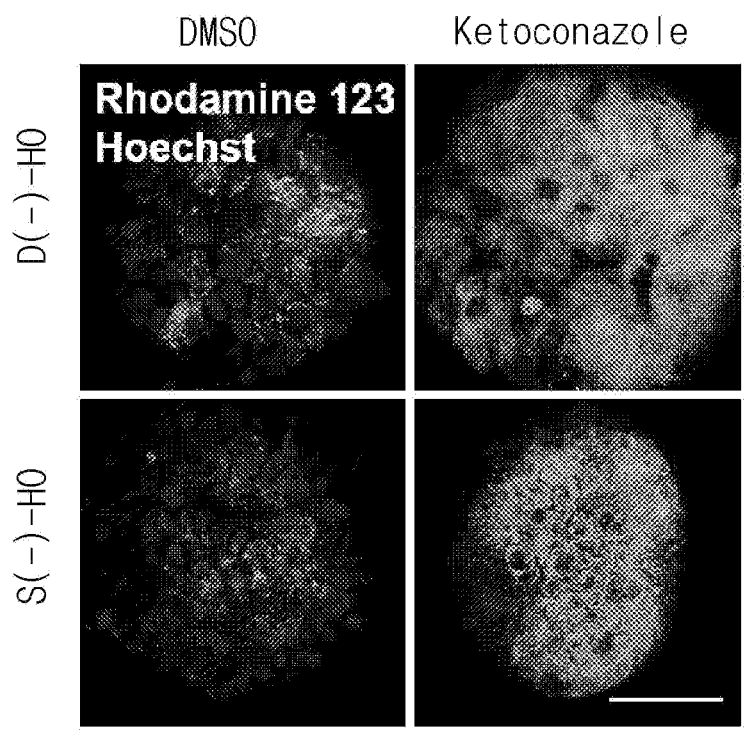
FIG. 23 is a set of photographs confirming the expression of BSEP (stained with CLF), an apical drug transporter, in the apical membranes of D(−)-HO and S(−)-HO, and that each drug transporter-specific fluorescence was accumulated in the lumen of a liver organoid as a result of treatment with ketoconazole, a BSEP inhibitor.

As a result, as shown in FIG. 21, the expression of MRP2 (stained with CDFDA) was confirmed in the apical membranes of D(−)-HO and S(−)-HO, and as shown in FIG. 22, the expression of MDR1 (stained with rhodamine 123) was confirmed. As shown in FIG. 23, it was confirmed that BSEP (stained with CLF) was specifically detected in the apical membrane of the liver organoids (green fluorescence). The emission of each absorbed fluorescence was observed at steady state, and when blocked by inhibitors of each transporter (MRP2 inhibitor: probenecid, MDR1 and BSEP inhibitor: ketoconazole), confirming the activity of the transporter in D(−)-HO and S(−)-HO, each drug transporter specific fluorescence accumulated in the lumen of the liver organoids. As shown in FIG. 23, rhodamine 123 was not released extracellularly due to cytoplasmic accumulation by MDR1 suppression.

These results suggest that the prepared liver organoids have a drug release function due to the high expression of the apical efflux drug transporter by the development of the apical membrane present in the lumen rather than the basolateral side of the liver organoids.

EXPERIMENTAL EXAMPLE 5: CELLULAR COMPOSITION OF LIVER ORGANOIDS AND EXPRESSION OF HEPATOCYTE-SPECIFIC MARKERS

To investigate the cellular composition of liver organoids, single-cell transcriptome analysis of S(−)-HO was performed by single-cell RNA sequencing.

Specifically, for a scRNA-seq library, Chromium Single Cell 3'Reagent Kit v3, Chromium Chip B Single Cell Kit and Chromium i7 Multiplex Kit (10X Genomics) were used. Liver organoids were isolated using an embryoid body dissociation kit (Miltenyi Biotec), filtered through a 35 µm strainer, and loaded onto a Chromium microfluidic platform to capture 7,000 individual cells. The library was sequenced with paired-end on the Illumina HiSeq X Ten platform. Sequencing the Single Cell 3' library generated a FASTQ file containing paired-end Read 1 (with 16 bp 10x™ barcode and 12 bp UMI) and Read 2, a sample index of i7 index reads. The file was processed with Cell Ranger™ (v3.1.0) using default arguments. Reads were aligned to the human reference genome (GRCh38). Cells with less than 2,000 genes detected using Seurat (v3.0.4) R package and with UMI more than 10% were further filtered using Seurat (v3.0.4) R package and finally a 20,125×1,859 gene-specific matrix was obtained. The expression matrix was imported and analyzed using scanpy (v1.4.5.1) Python package. The cells were visualized in a two-dimensional ForceAtlas2 plot using the tl.draw_graph function and then recalculated with PAGA-initialization. Clustering was performed using the tl.leiden function with "n_neighbors=4", "n_pcs=20" and "resolution=1". Using the Wilcoxon rank-sum test option and the tl.rank_genes_groups function, the marker genes of clusters and cell groups were found. Gene set expression scores including hepatocyte-like, biliary-like, gallbladder-like and cell cycle were calculated using the tl.score_genes function. Gene ontology and KEGG pathway analyses were performed using DAVID.

Figure 24:
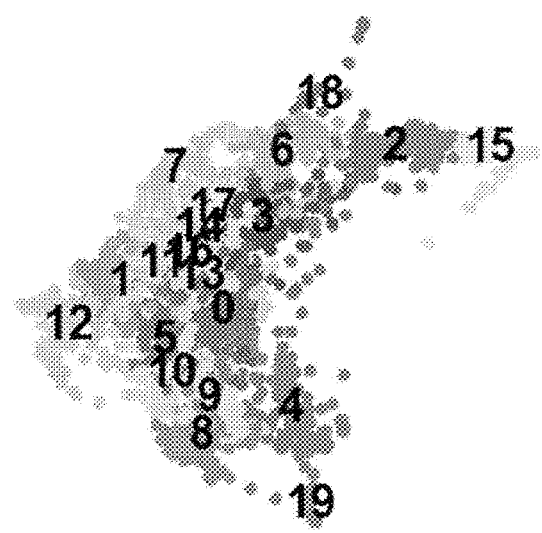
FIG. 24 is a diagram confirming the existence of 19 different cell clusters in a liver organoid.

As a result, as shown in FIG. 24, it was confirmed that 19 different cell clusters existed in the liver organoid.

Figure 25:
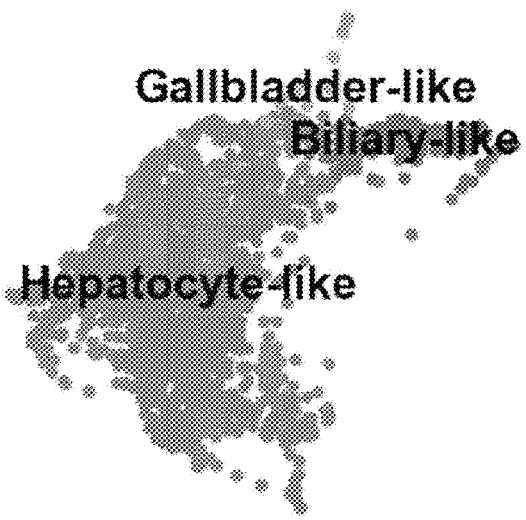
FIG. 25 is a diagram confirming that the liver organoid is composed of three cell groups, the first group contains biliary-like cells, the second group contains gallbladder-like cells, and the third group contains hepatocyte-like cells.

In addition, as shown in FIG. 25, the cells were classified into three groups based on the gene expression patterns and GO-term analysis, and it was confirmed that the first group consisted of clusters 2 and 15 and contained biliary-like cells, the second group consisted of cluster 18 and contained gallbladder-like cells, and the third group consisted of the remaining clusters and contained hepatocyte-like cells.

Figure 26:
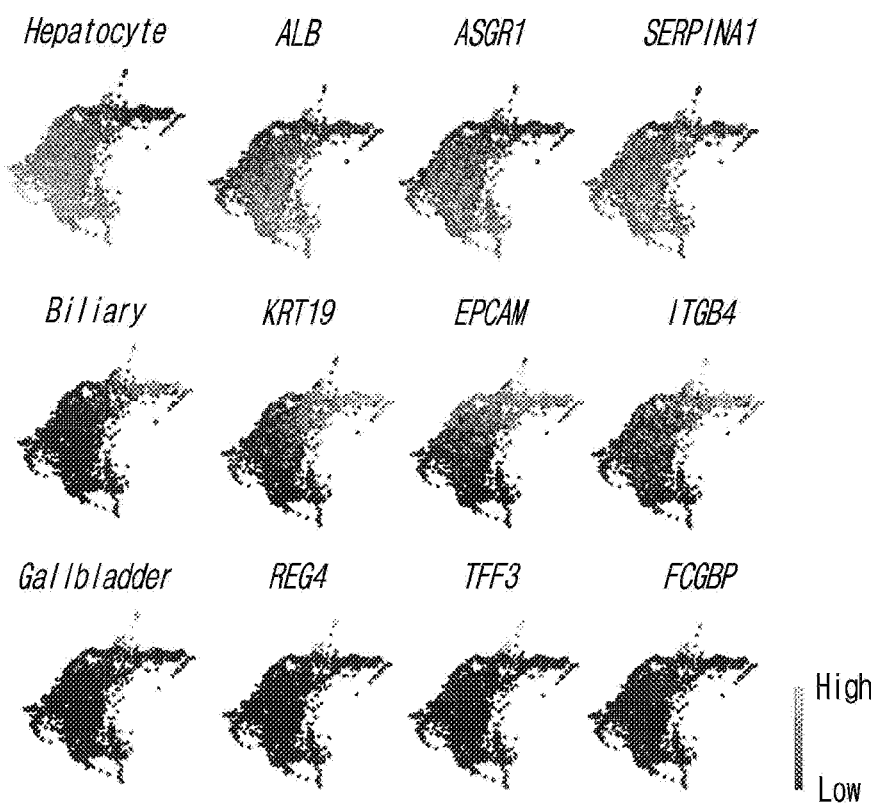
FIG. 26 is a diagram confirming the expression of representative markers of each group (ALB, ASGR1, and SERPINA1 for hepatocytes; KRT19, EPCAM, and ITGB4 for biliary; and REG4, TFF3, and FCGBP for gallbladder).

In addition, as shown in FIG. 26, it was confirmed that the representative markers of each group (ALB, ASGR1, and SERPINA1 for the hepatocytes lineage; KRT19, EPCAM, and ITGB4 for the biliary lineage; and REG4, TFF3, and FCGBP for the gallbladder lineage) were expressed. As shown in FIG. 27, specific markers in each group were exclusively expressed in each cluster. It was also confirmed that the liver organoid contained 88.44% of hepatocytes-like cells, a similar ratio to ALB-expressing cells, 10.38% of biliary-like cells, and 1.18% of gallbladder-like cells.

These results suggest that the liver organoid is composed of hepatocyte-like cells, biliary-like cells, and gallbladder-like cells including progenitor-like cells expressing cell-specific markers, and can mimic the liver.

EXPERIMENTAL EXAMPLE 6: MEASUREMENT OF DRUG METABOLIC CAPABILITY OF LIVER ORGANOIDS

Since metabolic elimination of drugs is one of the main functions of liver tissue, reproducible high functional drug metabolic capability is required in drug efficacy and toxicity tests in liver organoid models. Therefore, in order to confirm whether the liver organoids exhibit appropriate drug metabolic capability, the expression levels of major CYP450s including CYP1A2, CYP2C9, CYP2C19, CYP2D6, and CYP3A4 were measured by performing RT-qPCR using the same methods and conditions as described in Experimental Example 1 and compared with other in vitro models (liver cancer cell line (HepG2), primary human hepatocytes (PHH), and 2D hPSC-derived hepatocyte-like cells (2D HLC)). The activity of major CYP450 was measured by LC-MS/MS analysis.

Specifically, to measure the basal CYP450 activity, substrate reactions were performed in droplet-shaped liver organoids (D(-)HO), suspension-type liver organoids (S(-)HO), primary human hepatocytes (PHH), liver cancer cell line (HepG2), and 2D hPSC-derived hepatocyte-like cells (2D HLC) at 37° C., 5% $CO_2$ for 24 hours. CYP450 isoform specific substrate cocktail sets are as follows: set A, 50 µM phenacetin for CYP1A2, 5 µM coumarin for CYP2A6, 5 µM amodiaquine for CYP2C8, 100 µM S-mephenytoin for CYP2C19, 20 µM dextromethorphan for CYP2D6, and 5 µM midazolam for CYP3A4; set B, 50 µM bupropion for CYP2B6, 90 µM diclofenac for CYP2C9, and 90 µM chlorzoxazone for CYP2E1. Each CYP450 isoform-specific substrate cocktail set was cultured in a 24-well culture plate with a final volume of 0.6 mℓ per well. 80 µℓ of the medium was collected at 2, 4, 6, and 24 hours, respectively, and the reaction was quenched by adding 80 µℓ of ice-cold acetonitrile (ACN) containing 100 nM carbamazepine (CBZ) and 300 nM 4-methylumbelliferone (4-MUF). The samples were centrifuged at 16,000 g for 10 minutes at 4° C. and the supernatant was applied to liquid chromatography-tandem mass spectrometry (LC-MS/MS). Data were normalized to protein concentration.

As a result, as shown in FIG. 28, except for the CYP1A2 gene, the four CYP450 genes of D(-)-HO and S(-)-HO showed higher expression levels than D(+)-HO and S(+)-HO. Furthermore, as shown in FIG. 29, the activities of the major CYP450s were found to differ in metabolite production in response to R Spondin-1 and EGF addition only in droplet-type culture, but not in suspension culture. The activities of CYP2C9 and CYP2C19 in D(-)-HO and S(-)-HO were similar to those in primary human hepatocytes (PHH). The liver organoids showed higher levels of the CYP450 expression and activity than HepG2 and 2D HLC, whereas the metabolite production mediated by CYP1A2, CYP2D6 and CYP3A4 was lower compared to PHH.

The above results indicate that the expression and activity of drug metabolism enzymes, CYP450, increases when liver organoids are differentiated in a medium that does not contain R-Spondin 1 and EGF at the expansion stage.

EXPERIMENTAL EXAMPLE 7: CONFIRMATION OF EFFECT ON CYP450 ACTIVITY WHEN DIFFERENTIATING LIVER ORGANOIDS IN MEDIUM SUPPLEMENTED WITH FERRIC CITRATE (FC)

Figure 30:
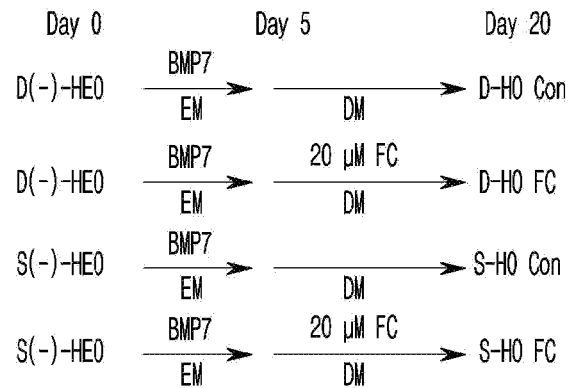
FIG. 30 is a schematic diagram showing the process of differentiating hepatic endoderm organoids into liver organoids using a liver organoid differentiation medium containing 20 µM ferric citrate (FC).

Heme (iron(III) protoporphyrin-IX) is an important cofactor for oxygen activation when bound to CYP450. Ferric citrate (FC) increases hepatic iron accumulation in macrophages and hepatocytes (Chang et al., 2018; Lim et al., 2019). Therefore, the present inventors examined whether iron(III) supplementation during the differentiation stage of liver organoids could enhance CYP450 activity (FIG. 30).

Specifically, hepatic endoderm organoids were differentiated into liver organoids using a liver organoid differentiation medium containing 20 or 50 µM ferric citrate (FC) for 15 days by the same methods and conditions as in Example 2. For live and dead cell analysis, the liver organoids treated with or without FC were stained with a live/dead viability/cytotoxicity kit (Thermo). Images were observed using an Olympus FV3000 confocal microscope. The viability of liver organoids was measured using CCK-8 (Dojindo) assay. The values were normalized to those obtained from CellTiter-Glo® 3D cell viability assay (Promega). The survival rate (%) of the control liver organoids was normalized to 100%.

Samples were analyzed using a Prominence UFLC system with a parallel LC-20ADXR pump, autosampler, and column oven (Shimadzu) for detection and quantification of metabolites of CYP450. The sample injection amount was 10 µℓ, and the separation was performed on an Atlantis dC18 column (2.1 mm×50 mm id, 3 µm, Waters, Milford, MA) with a SecurityGuard C18 guard column (2.0 mm×4.0 mm id; Phenomenex, Torrence, CA) maintained at 30° C.. The flow rate of HPLC was set to 0.4 mℓ/min. The HPLC mobile phase consisted of A [deionized water containing 0.1% (v/v) formic acid] and B [acetonitrile containing 0.1% (v/v) formic acid]. LC-MS/MS data were collected using an Applied Biosystems SCIEX 3200 QTRAP hybrid triple quadrupole-linear ion trap mass spectrometer equipped with a TurboIonSpray interface operating in positive or negative (for CYP2E1) ESI mode. In addition, 4-hydroxy diclofenac was set to m/z 312→230 in positive mode. Data collection and analysis were performed with Analyst™ software (ver. 1.6.2; Applied Biosystems, Foster city, CA).

Figure 31:
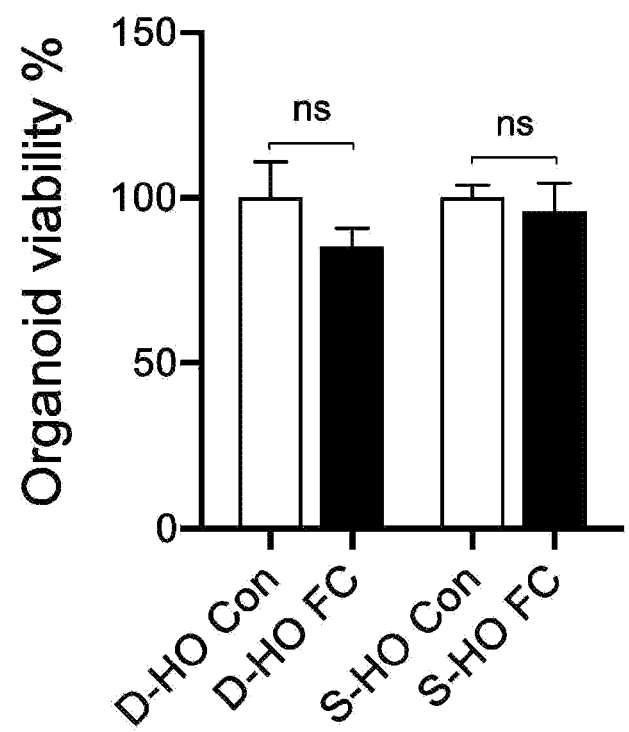
FIG. 31 is a graph showing that there is no cytotoxicity when differentiated into liver organoids using a liver organoid differentiation medium containing 20 µM ferric citrate (FC).
Figure 32:
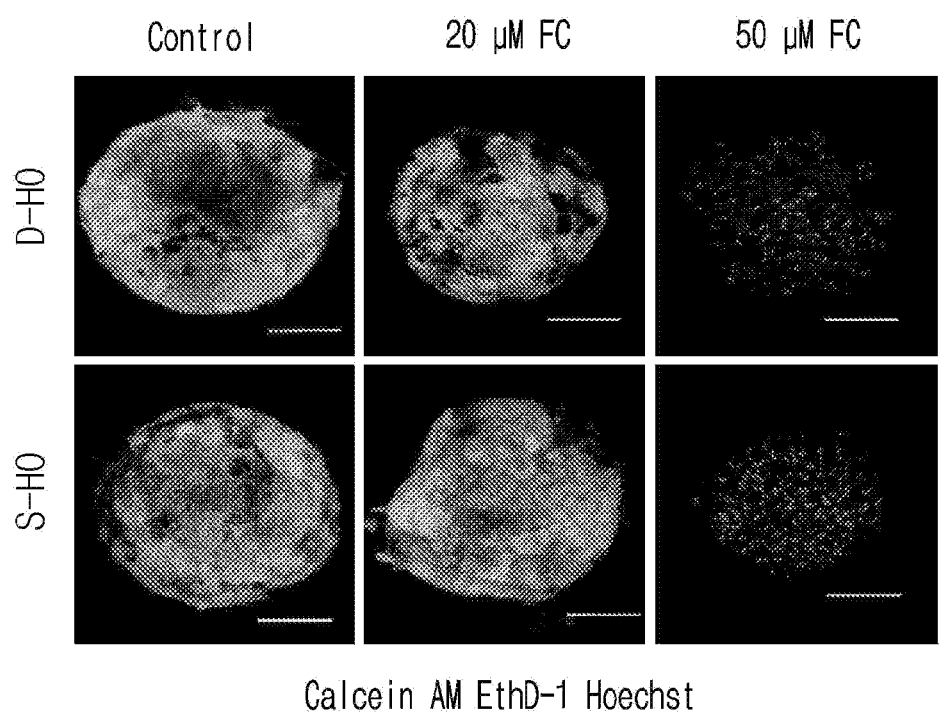
FIG. 32 is a set of photographs showing that cells are viable when differentiated into liver organoids using a liver organoid differentiation medium containing 20 µM ferric citrate (FC).

As a result, as shown in FIG. 31, ferric citrate (FC) did not exhibit cytotoxicity when treated at a dose of 20 µM in the medium composition of Tables 8 and 9. In addition, as shown in FIG. 32, when 50 µM of ferric citrate was included in the medium, only red fluorescence of EthD-1 from dead cells appeared, but when 20 pM of ferric citrate was included in the medium, green fluorescence of Calcein AM from live cells appeared, so the treatment dose of ferric citrate was determined to be 20 µM.

In addition, as shown in FIG. 33, the CYP450 activity was greatly increased by ferric citrate treatment except for CYP1A2 in the liver organoids (S-HO FC) cultured in suspension. To observe the maintenance of CYP450 enzyme activity over a longer period of time, the activities of CYP1A2, CYP2C9, CYP2C19, CYP2D6, and CYP3A4 of D-HO and S-HO FC were measured for 7-days. As a result, as shown in FIG. 34, the activities of CYP1A2, CYP2C9, and CYP2D6 were maintained for 7 days, whereas the activities of CYP2C19 and CYP3A4 tended to decrease from day 4.

These results suggest that iron is required to increase CYP450 activity in liver organoids.

EXPERIMENTAL EXAMPLE 8: DRUG TOXICITY TEST OF LIVER ORGANOIDS

<8-1> Evaluation of Drug Toxicity in Liver Organoids

To confirm the utility of liver organoids as a cell model for drug toxicity evaluation, drug toxicity evaluation was performed in liver organoids, liver cancer cell line (HepG2), and 2D hPSC-derived hepatocyte-like cells (2D HLC).

Specifically, D-HO, S-HO, HepG2, and 2D HLC prepared by culturing in a culture medium containing iron citrate were cultured in a 96-well plate. Compounds (ticlopidine and flutamide) at 1-, 5-, 10-, 20-, and 40-fold Cmax concentrations were prepared in each base medium, and the final DMSO concentration was 0.1%. The liver organoids or cells were treated with the compounds for 24 hours, and the viability was measured using CellTiter-Glo® 3D Cell Viability Assay (Promega). The values obtained were normalized to the control group. The normalized values were used to visualize the dose-response relationship as a non-linear regression curve and to calculate $IC_{50}$ values (GraphPad Prism, GraphPad Software, San Diego, CA). In addition, the sensitivity of different cell types to each compound tested was shown as a heatmap of $IC_{50}$ values (GraphPad Prism).

Figure 35:
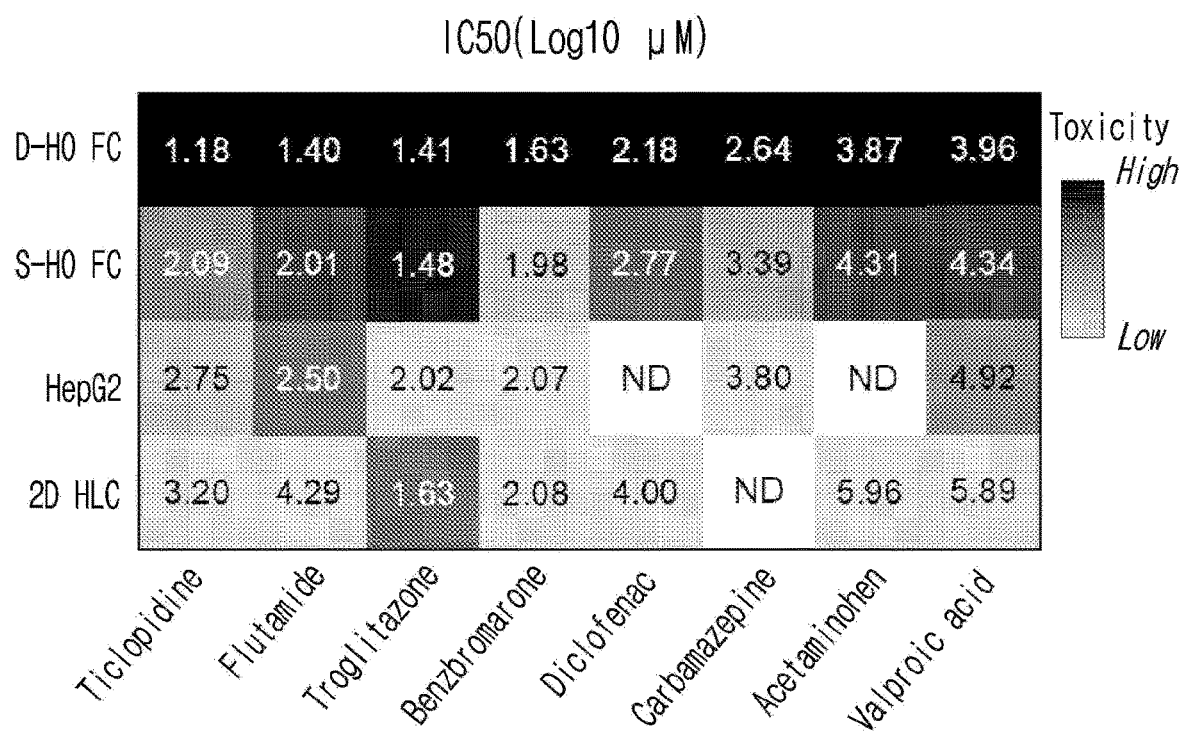
FIG. 35 is a diagram showing that D-HO FC has cytotoxicity for most drugs at lower concentrations than other cell models.

As a result, as shown in FIG. 35, it has been observed that most drugs show cytotoxicity in D-HO FC at lower concentrations than in other cell models.

<8-2> Evaluation of CYP450-Mediated Drug Metabolic Capability of Liver Organoids To confirm the utility of liver organoid as a cell model for drug metabolic capability evaluation, CYP450-mediated drug metabolic capability was compared in liver organoids (D-HO FC and S-HO FC) and primary human hepatocytes (PHH).

Specifically, compounds including amitriptyline for CYP2D6 and CYP2C19, chlorpromazine for CYP2D6, and diclofenac for CYP2C9 and UGT2B7 were used to measure the amount of prodrugs in the media of liver organoids and PHH. The compounds were treated at a concentration of 1 µM for 24 hours at 37° C. in 5% $CO_2$. They were cultured in each 24-well culture plate to a final volume of 0.7 mℓ per well. 60 µℓ of medium was collected at 1.5, 3, 6, 12, and 24 hours, respectively, and the reaction was quenched by adding 60 µℓ of ice-cold ACN containing 100 nM CBZ and 300 nM 4-MUF. The samples were centrifuged at 16,000 g for 10 minutes at 4° C. and the supernatant was applied to liquid chromatography-tandem mass spectrometry (LC-MS/MS). The values of compound only (organic or cell free) were used as a control. Data were normalized to protein concentration.

Figure 36:
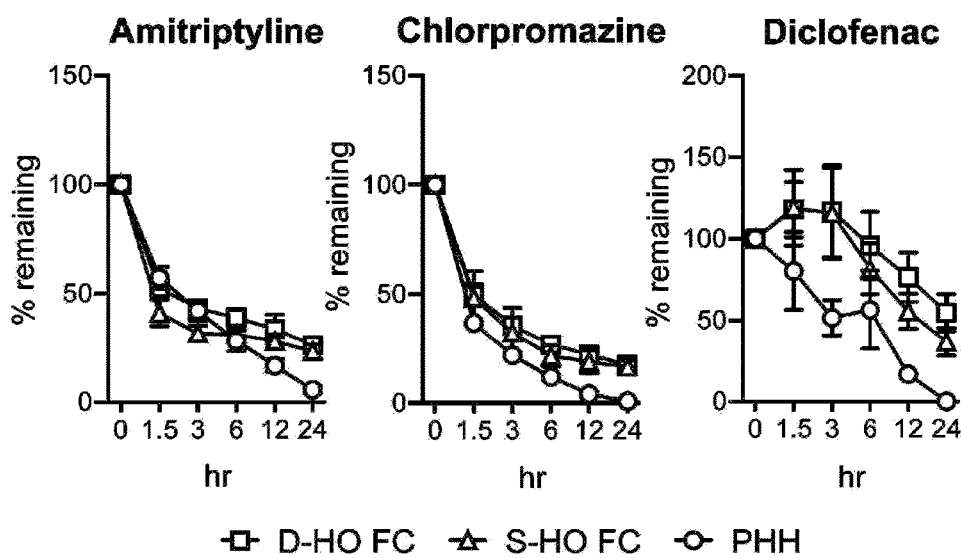
FIG. 36 is a set of graphs showing that the liver organoids differentiated using a liver organoid differentiation medium containing ferric citrate have the ability to metabolize drugs including amitriptyline (CYP2D6 and CYP2C19), chlorpromazine (CYP2D6), and diclofenac (CYP2C9 and UGT2B7).

As a result, as shown in FIG. 36, the CYP450-mediated drug metabolic capability was determined using the disappearance of drugs including amitriptyline (CYP2D6 and CYP2C19), chlorpromazine (CYP2D6), and diclofenac (CYP2C9 and UGT2B7) in D-HO FC and S-HO FC, and showed the drug metabolic capability in the liver organoids similar to PHH.

<8-3> Evaluation of Ability of Liver Organoids to Metabolize Acetaminophen

Figure 37:
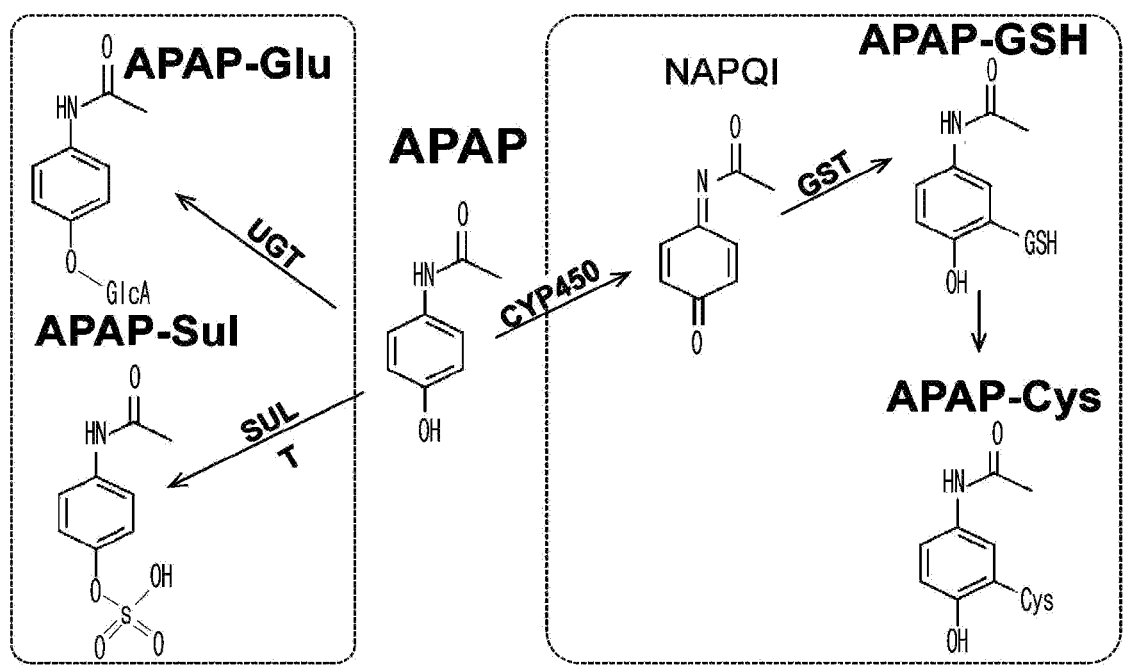
FIG. 37 is a diagram showing the metabolic pathway of acetaminophen in the liver.

Acetaminophen (APAP), a safe and effective analgesic and antipyretic, is known to undergo extensive hepatic metabolism through two pathways: detoxification (conjugation such as glucuronidation and sulfation) and bioactivation (CYP450-mediated oxidation) (Hodgman and Garrard, 2012). Acetaminophen metabolism was tested under non-cytotoxic concentrations in D-HO, S-HO, PHH, HepG2 and 2D HLC. Conjugate reactions by UGT (UDP-glucuronosyl transferase) and SULT (sulfotransferase) are the major metabolic pathways for APAP metabolism (FIG. 37).

Specifically, to measure the metabolites of APAP, reactions were performed in PHH, D-HO, S-HO, HepG2, and 2D HLC treated with 10 mM APAP for 24 hours at 37° C. in 5% $CO_2$. APAP was treated to a final volume of 0.7 mℓ per well in each 24-well culture plate. 70 µℓ of medium was collected at 3, 6, 12 and 24 hours, respectively, and the reaction was quenched by adding 70 µℓ of ice-cold ACN containing 100 nM BR-A-563 as an internal standard. The samples were centrifuged at 16,000 g for 10 minutes at 4° C. and the supernatant was applied to liquid chromatography-tandem mass spectrometry (LC-MS/MS). Data were normalized to protein concentration.

Figure 38:
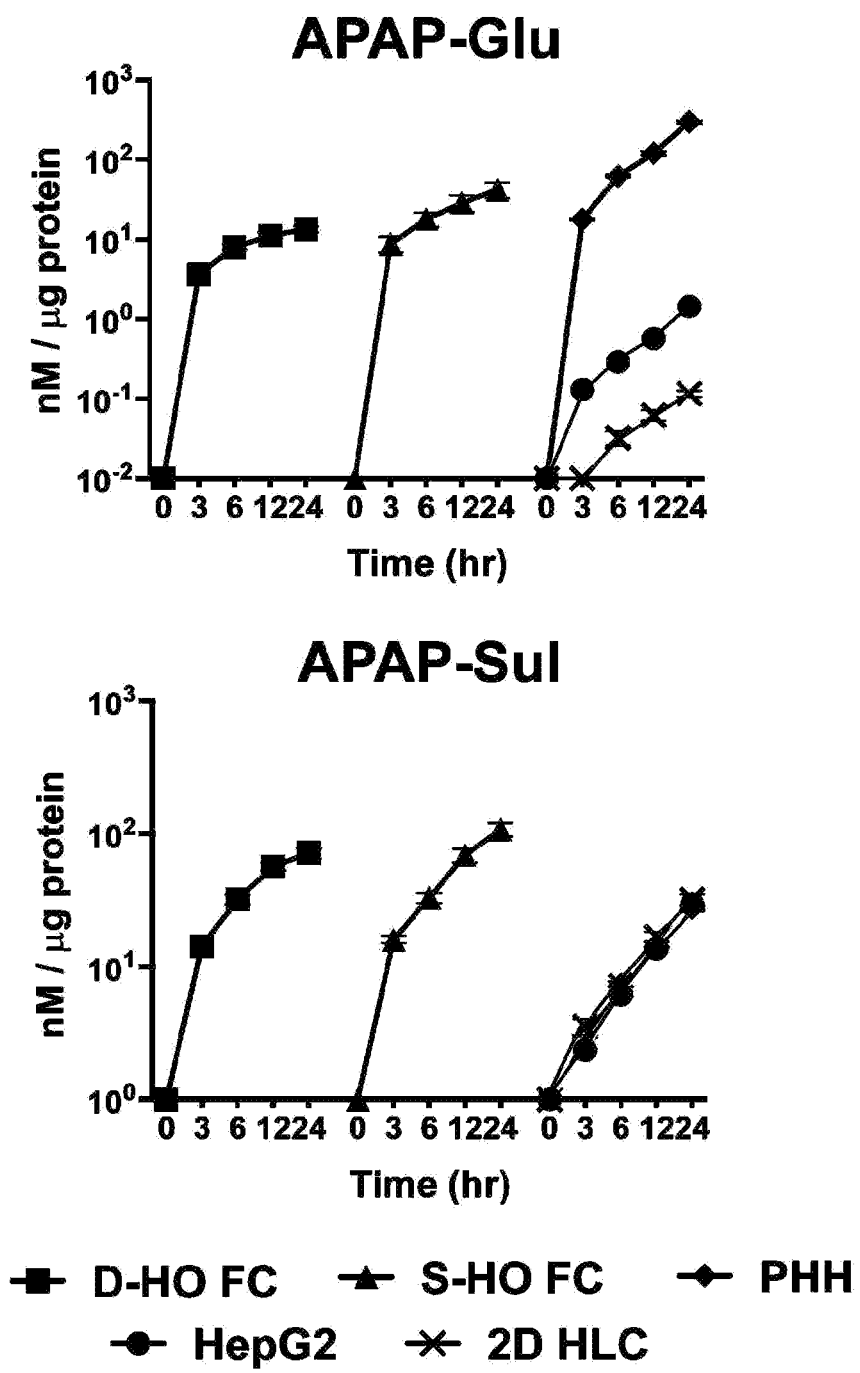
FIG. 38 is a set of graphs showing the concentrations of APAP-glucuronide (APAP-Glu) and APAP-sulfate (APAP-Sul), the non-CYP450 mediated metabolites of acetaminophen in the liver in liver organoids, primary human hepatocytes (PHH), liver cancer cell line (HepG2), and 2D hPSC-derived hepatocyte-like cells.
Figure 39:
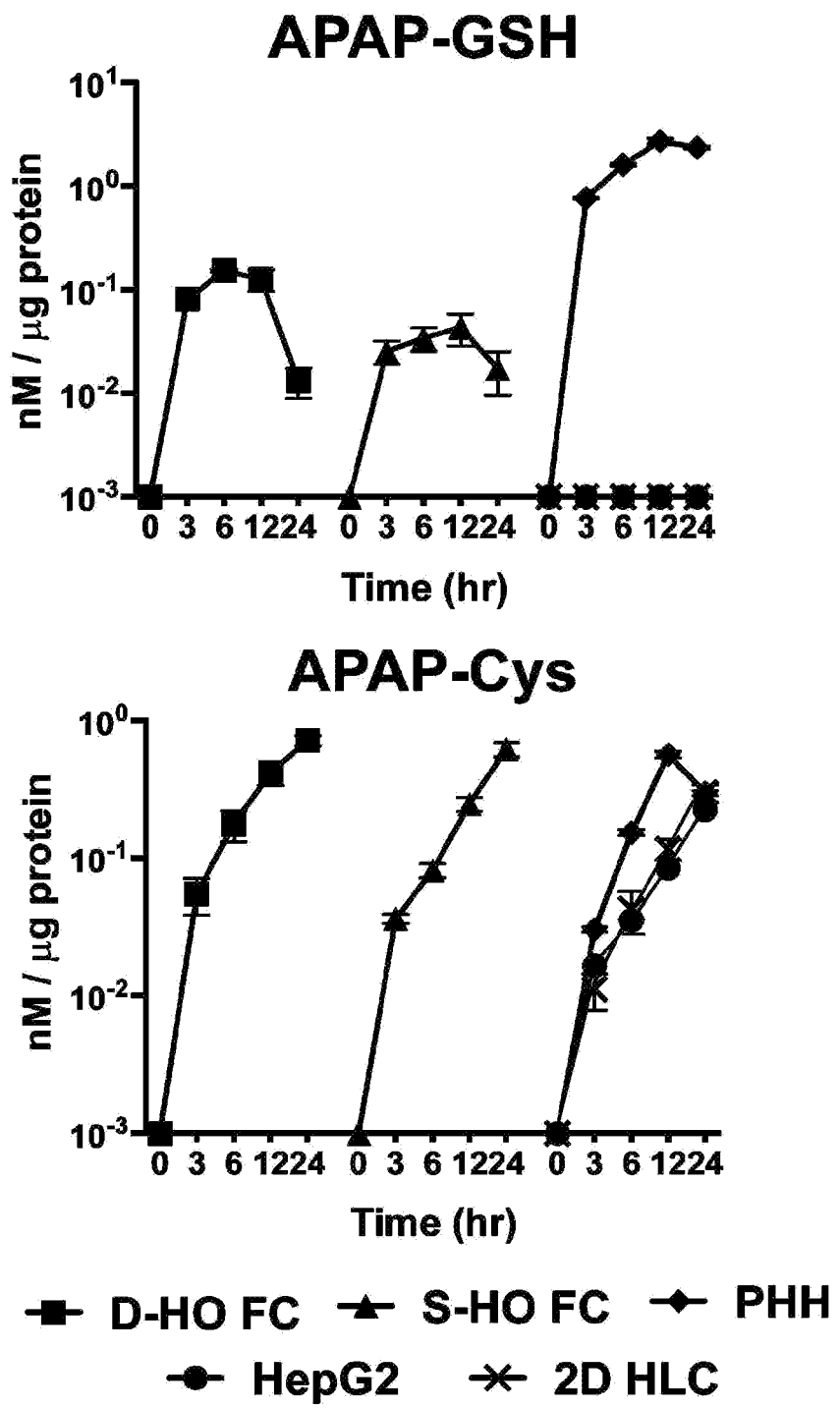
FIG. 39 is a set of graphs showing the concentrations of APAP-glutathione (APAP-GSH) and APAP-cysteine (APAP-Cys), the CYP450-mediated metabolites of acetaminophen in the liver in liver organoids, primary human hepatocytes (PHH), liver cancer cell line (HepG2), and 2D hPSC-derived hepatocyte-like cells.

As a result, as shown in FIG. 38, APAP-glucuronide (APAP-Glu) was produced in higher amounts in D-HO, S-HO and PHH than in HepG2 and 2D HLC. In addition, as shown in FIG. 39, for APAP-GSH, the amount of metabolites tended to decrease after 12 hours in D-HO, S-HO and PHH, while no metabolites were detected in HepG2 and 2D HLC. These results suggest that the liver organoid has the ability to metabolize acetaminophen.

<8-4> Evaluation of Ability of Liver Organoids to Metabolize Fimasartan

Figure 40:
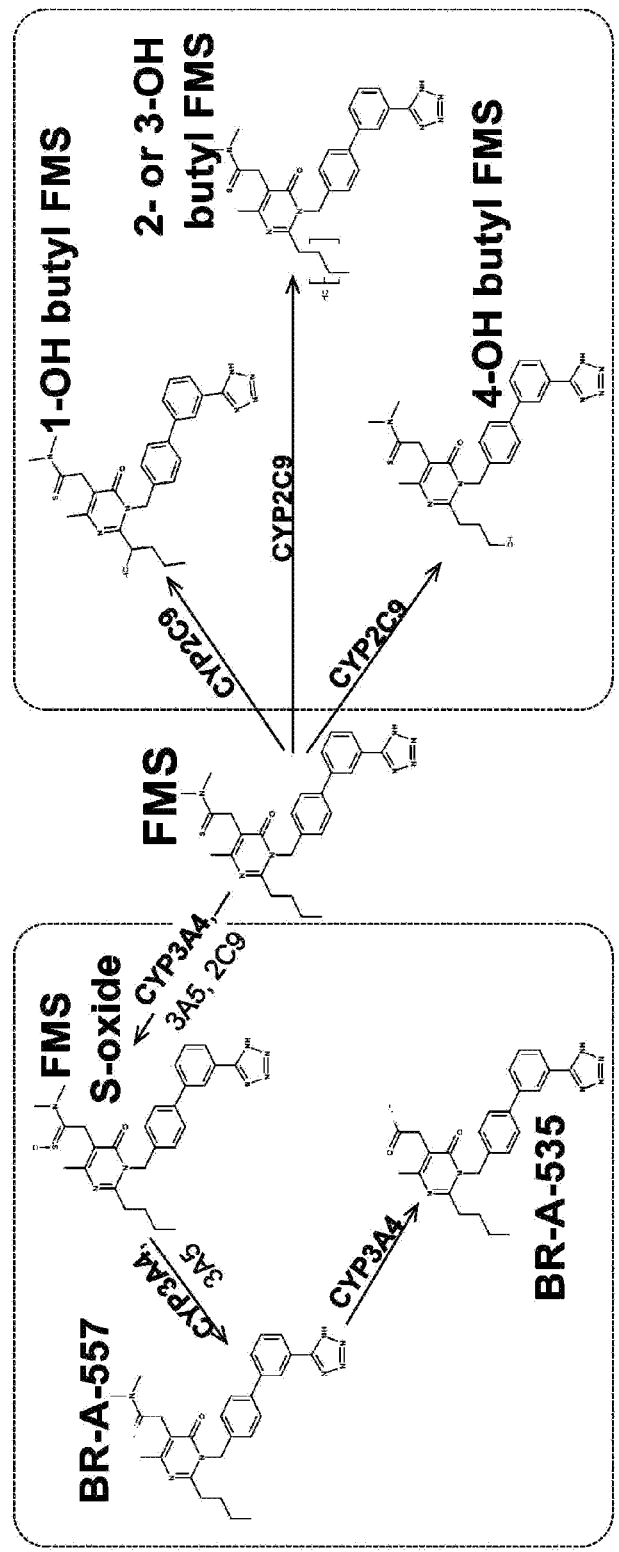
FIG. 40 is a diagram showing the metabolic pathway of fimasartan in the liver.

Fimasartan (FMS), an angiotensin II receptor blocker, is used to treat hypertension and is known to be metabolized by CYP2C9, CYP3A4, and CYP3A5. FMS metabolism was tested using D-HO, S-HO, PHH, HepG2, and 2D HLC at the concentrations that did not show cytotoxicity. FMS is further metabolized to BR-A-557 by CYP3A4/5 and to BR-A-535 by CYP3A4, and CYP2C9, CYP3A4, and CYP3A5 are involved in the formation of FMS S-oxide (FIG. 40).

Specifically, to measure the metabolites of fimasartan (FMS), reactions were performed in PHH, D-HO, S-HO, HepG2, and 2D HLC treated with 50 µM FMS for 24 hours at 37° C. in 5% $CO_2$. FMS was processed to a final volume of 0.7 mℓ per well in each 24 well culture plate. 70 µℓ of medium was collected at 3, 6, 12 and 24 hours, respectively, and the reaction was quenched by adding 70 µℓ of ice-cold ACN containing 100 nM BR-A-563 as an internal standard. The samples were centrifuged at 16,000 g for 10 minutes at 4° C. and the supernatant was applied to liquid chromatography-tandem mass spectrometry (LC-MS/MS). Data were normalized to protein concentration.

Figure 41:
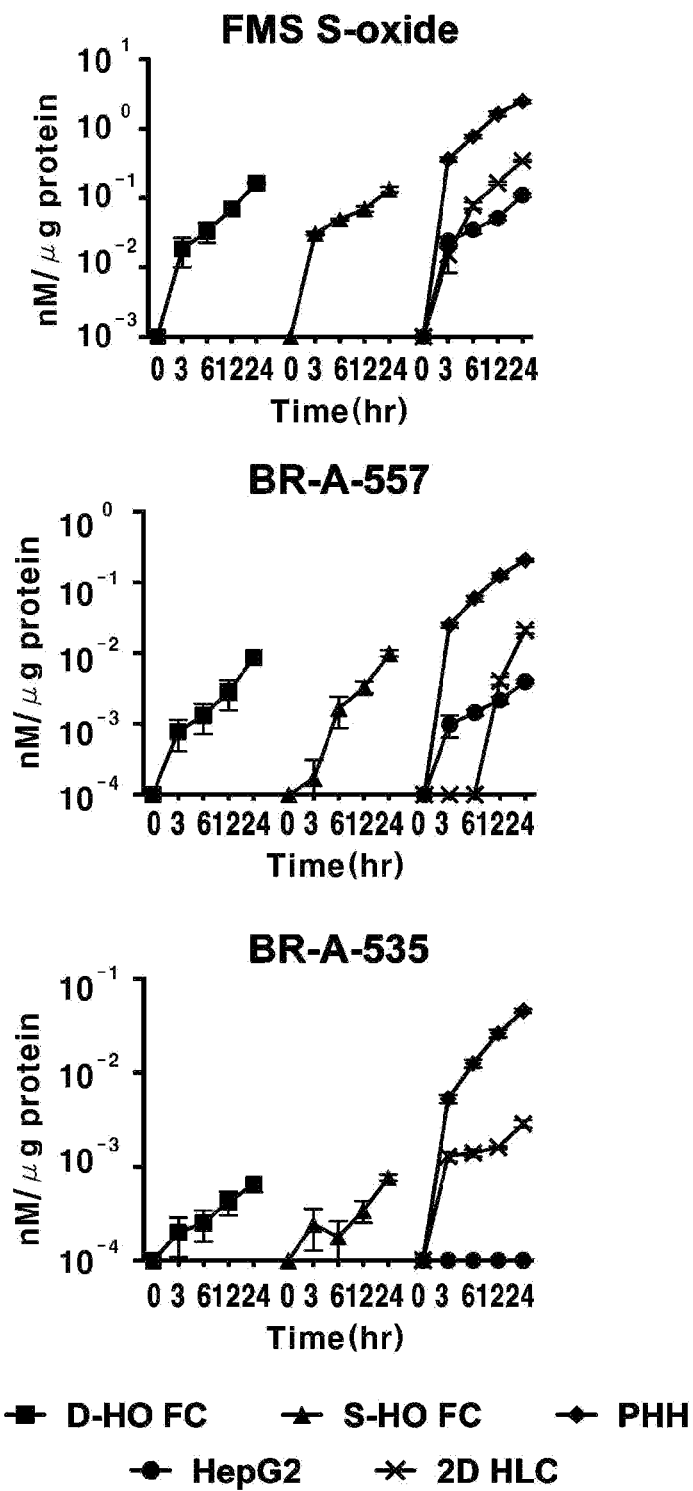
FIG. 41 is a set of graphs showing the concentrations of FMS S-oxide, BR-A-557, and BR-A-535, the CYP3A4-mediated metabolites of fimasartan in the liver in liver organoids, primary human hepatocytes (PHH), liver cancer cell line (HepG2), and 2D hPSC-derived hepatocyte-like cells.
Figure 42:
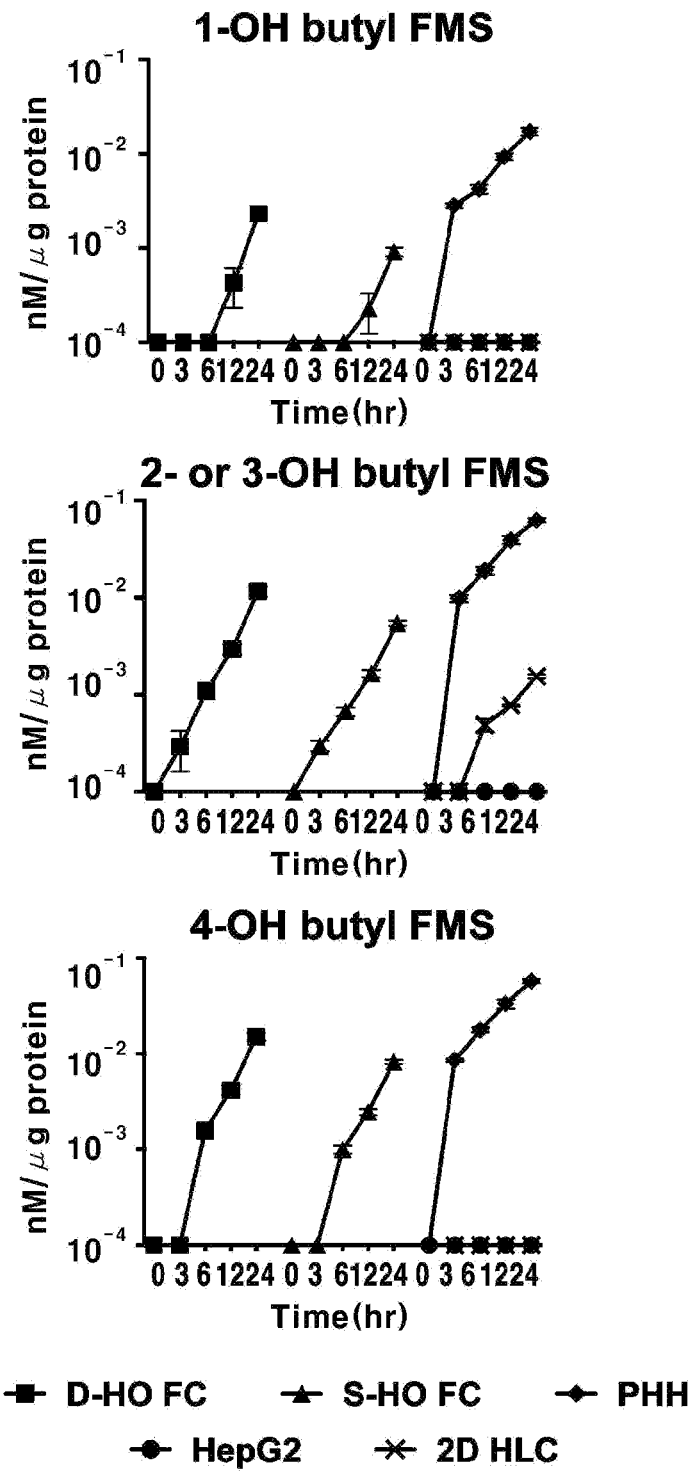
FIG. 42 is a set of graphs showing the concentrations of 1-OH butyl FMS, 2- or 3-OH butyl FMS, and 4-OH butyl FMS, the CYP2C9-mediated metabolites of fimasartan in the liver in liver organoids, primary human hepatocytes (PHH), liver cancer cell line (HepG2), and 2D hPSC-derived hepatocyte-like cells.

As a result, as shown in FIG. 41, the production of sequential metabolites of FMS was shown in PHH, hHO and 2D HLC, but the production of BR-A-535, a 3-step metabolite of FMS by CYP3A4, was not observed in HepG2. In addition, as shown in FIG. 42, CYP2C9 played an exclusive role in n-butyl hydroxylation of FMS. It was also confirmed that D-HO and S-HO produced more metabolites including 1-OH, 2- or 3-OH and 4-OH butyl FMS than HepG2 and 2D HLC.

These results suggest that liver organoids can serve as an in vitro model to study and test CYP450-mediated drug metabolism.

EXPERIMENTAL EXAMPLE 9: EVALUATION OF CARDIOTOXICITY OF LIVER ORGANOIDS

Whether liver organoids can be used to evaluate cardiotoxicity induced by drug metabolites was confirmed by treating liver organoids with cyclophosphamide and terfenadine.

<9-1> Evaluation of Cardiotoxicity of Cyclophosphamide (CP)

Figure 43:
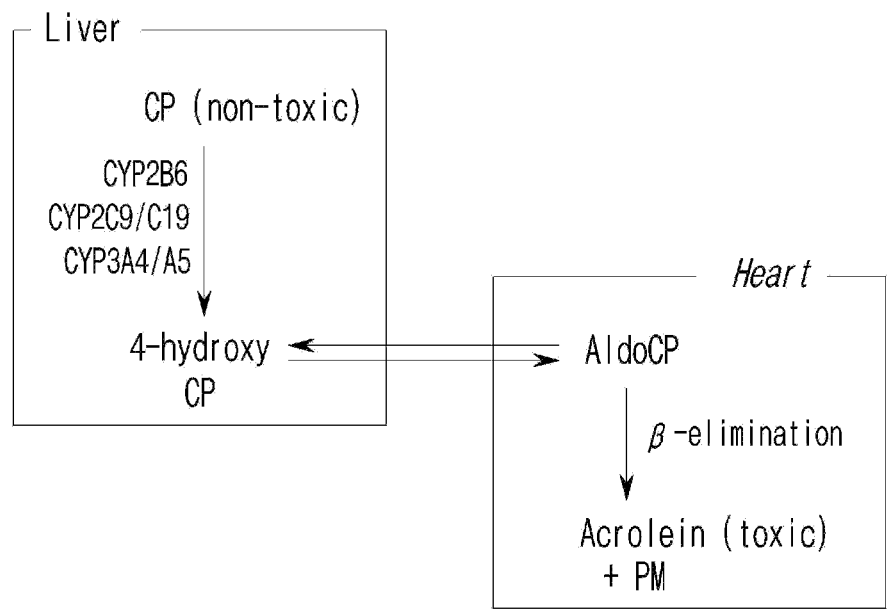
FIG. 43 is a diagram showing the metabolic pathway in which cyclophosphamide (CP) is metabolized in the liver and causes cardiotoxicity.

Cyclophosphamide (CP) is an alkylating agent used as an anticancer chemotherapy drug and is known to cause cardiotoxicity. CP is activated by hepatic CYP450, a group of drug metabolism enzymes including CYP2B6, CYP2C9/C19, and CYP3A4/A5, to form 4-hydroxy-CP and coexist with AldoCP, a tautomer. In the heart, AldoCP is broken down into acrolein and phosphoramide mustard (PM) (FIG. 43). Acrolein is a toxic metabolite that causes toxicity to the myocardium, cardiomyocytes and endothelial cells. Accordingly, the electrophysiological effects of CP on hiPSC-derived cardiomyocytes (hiPSC-CMs) co-cultured with or without FC-treated S(−)-HO were tested.

Specifically, the electrical activity of Cardiosight®-S (NEXEL Co., South Korea), the hiPSC-CM, was measured using an MEA system (Axion BioSystems, Maestro, US) at 37° C. and perfused with 5% $CO_2$, 20% $O_2$, and 75% $N_2$. The hiPSC-CMs were first seeded in a 12-well MEA plate at the density of $4\times10^4$ cells per well and maintained for 7 days in a cardiomyocyte culture medium provided by NEXEL Co. to stabilize with half-mid changes performed every 2 days. One week later, the culture medium was replaced with a liver organoid differentiation medium (DM). Transwell inserts (Corning) were then placed in each well, and FC-treated S(−)-HO was seeded in the inserts, followed by culture for 3 days. On the day of compound application, the culture medium was completely removed from the wells and inserts and fresh medium was added to ensure the correct volume per well (2 mℓ/well total). Cells were allowed to equilibrate for 4 hours, and online parameters were monitored to ensure a stable baseline for at least 40 minutes. The cells were exposed to cyclophosphamide at a single dose per well. After application of the drug or control (0.1% DMSO), field potentials were measured every 5 minutes for 30 seconds for 72 hours. The field potential signals were recorded and analyzed using Axion BioSystems' integrated studio (AxIS) software to measure the beating frequency and field potential duration. Fredericia's velocity correction algorithm (FPDcF) is commonly used to correct for velocity-dependent effects. Herein, FPDcF=FPD/Beat Period 0.33. Data were normalized to pretreated control values.

Figure 44:
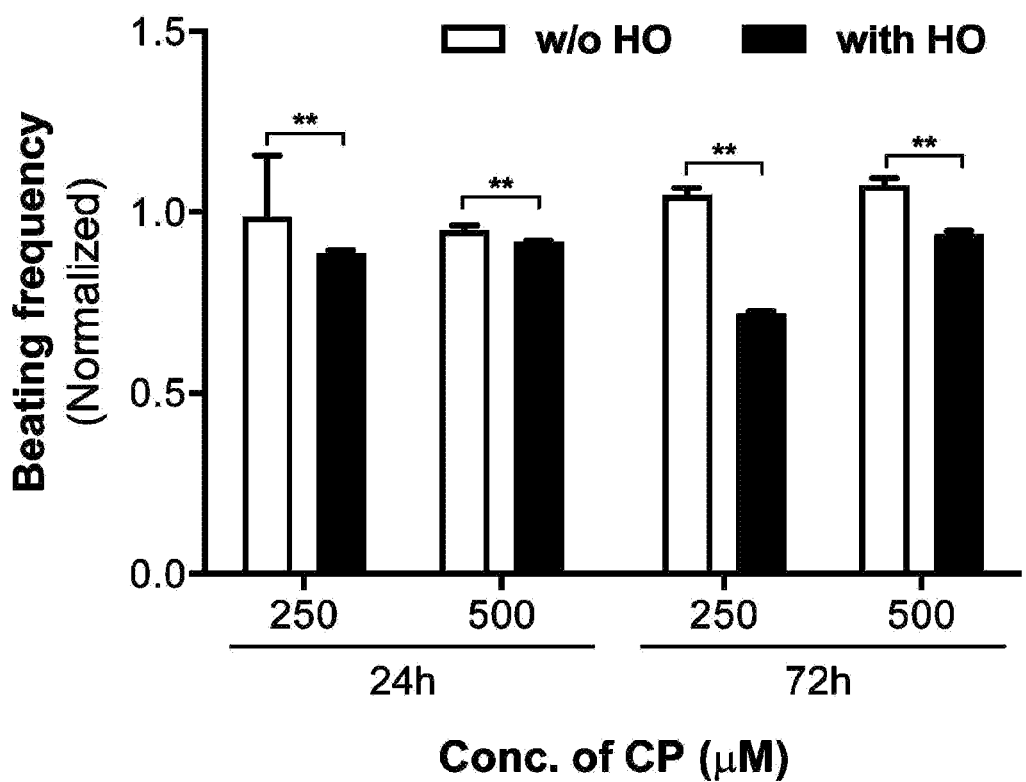
FIG. 44 is a graph showing the beating frequency of human induced pluripotent stem cell-derived cardiomyocytes (hiPCS-CMs) with or without liver organoids after treatment with cyclophosphamide at concentrations of 250 and 500 µM for 24 and 72 hours.

As a result, as shown in FIG. 44, after CP treatment at concentrations of 250 and 500 μM for 24 and 72 hours, the beating rate of hiPCS-CM with liver organoids was significantly reduced compared to hiPSC-CM alone, indicating the cardiotoxicity of CP.

Figure 45:
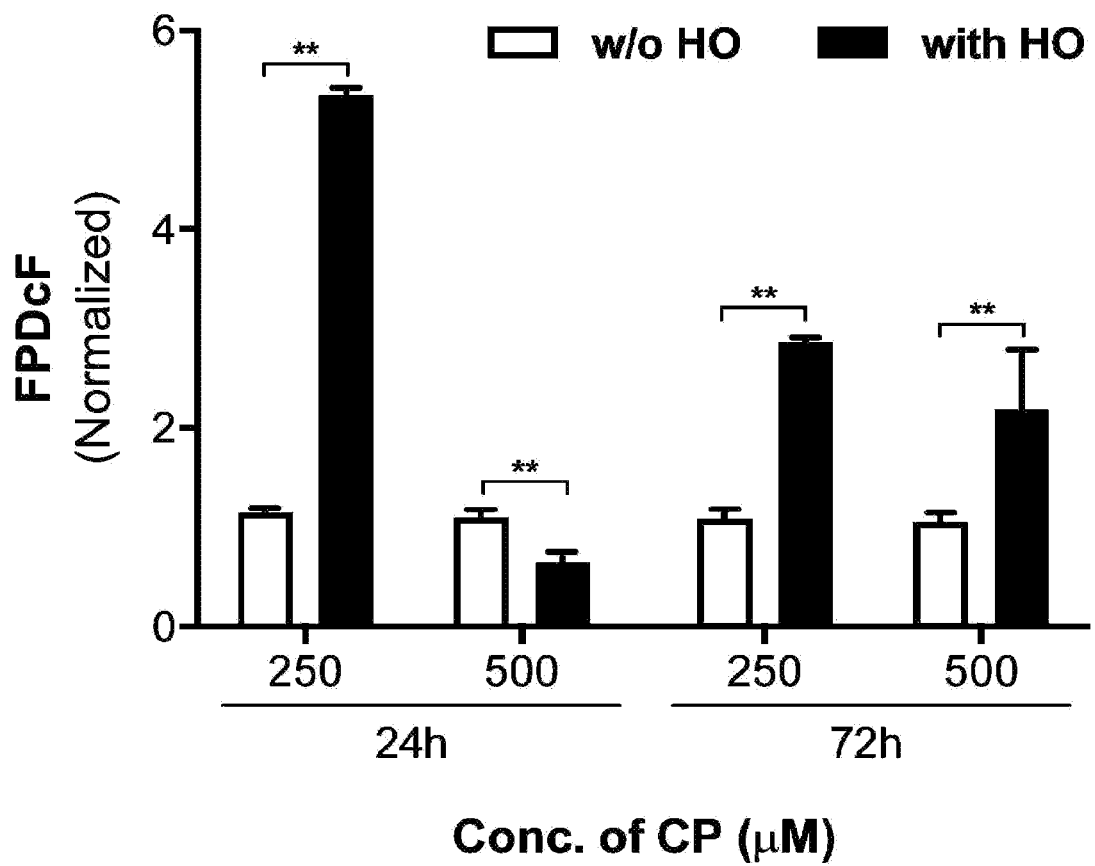
FIG. 45 is a graph showing the normalized field potential duration of hiPCS-CMs with or without liver organoids after treatment with cyclophosphamide at concentrations of 250 and 500 µM for 24 and 72 hours.

In addition, as shown in FIG. 45, the field potential duration corrected by beating frequency using Fridericia's formula (FPDcF) was increased after 24 and 72 hours when hiPSC-CM with liver organoids were treated with 250 μM CP, indicating cardiotoxicity.

<9-2> Evaluation of Cardiotoxicity of Terfenadine

Figure 46:
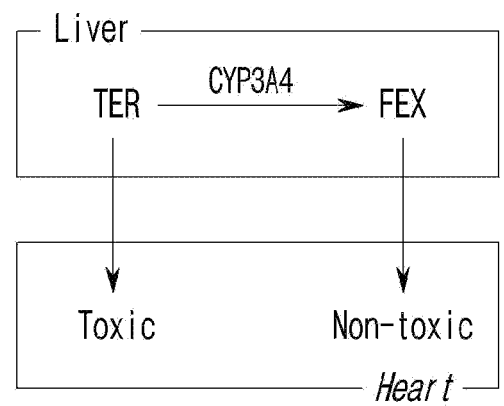
FIG. 46 is a diagram showing the metabolic pathway of terfenadine (TER) causing cardiotoxicity.

Terfenadine (TER) can cause life-threatening ventricular arrhythmias. Terfenadine is metabolized by CYP3A4 in the liver, and the main active metabolite is fexofenadine (FEX), which is known to have less toxic effects than terfenadine (FIG. 46).

The cardiotoxicity of terfenadine was measured in liver organoids by the same methods and conditions as in Experimental Example <9-1>, except that terfenadine was treated instead of cyclophosphomide.

Figure 47:
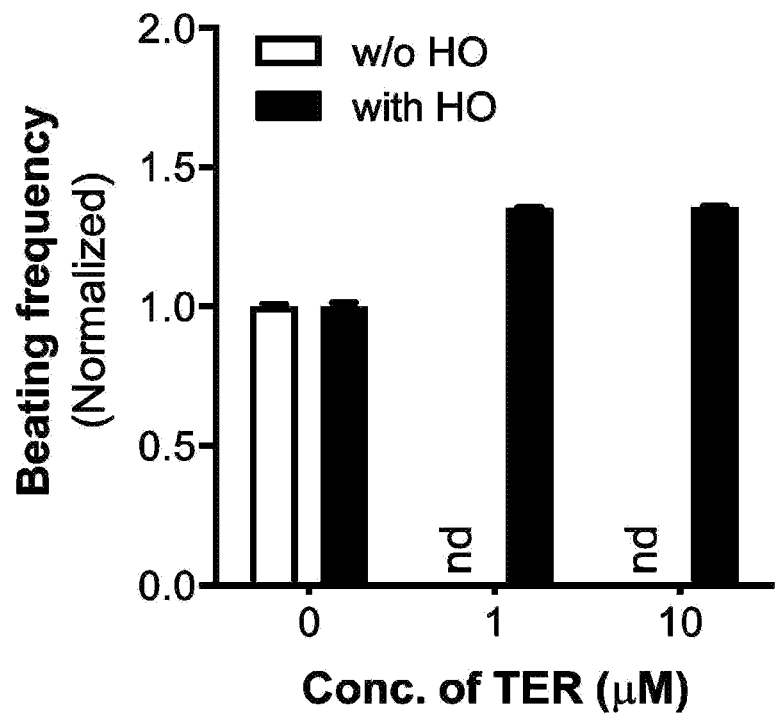
FIG. 47 is a graph showing the beating frequency of hiPCS-CMs with or without liver organoids after treatment with terfenadine at concentrations of 1 and 10 µM for 24 and 72 hours.
Figure 48:
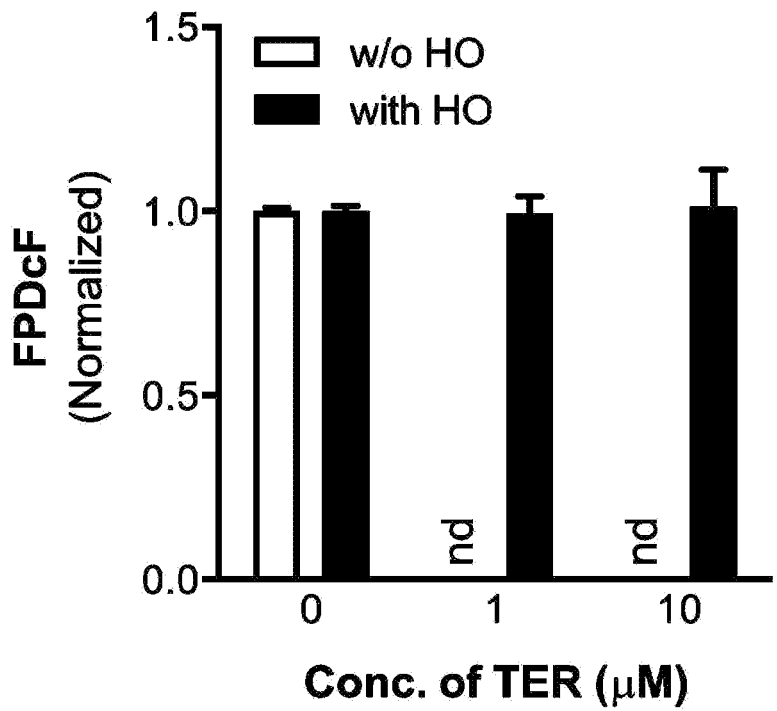
FIG. 48 is a graph showing the normalized field potential duration of hiPCS-CMs with or without liver organoids after treatment with terfenadine at concentrations of 1 and 10 µM for 24 and 72 hours.

As a result, as shown in FIG. 47, it was confirmed that the hiPSC-CM not cultured with liver organoids induced spontaneous beating cessation within 30 minutes of terfenadine addition. In addition, as shown in FIG. 48, it was confirmed that the hiPSC-CM cultured with liver organoids induced an increase in beating frequency by treatment with 1 and 10 μM TER, and FPDcF was not changed. These results indicate that the cardiotoxicity of terfenadine related to beat rate and field potential in hiPSC-CM was mitigated by metabolism through the liver organoids (fexofenadine without toxicity).

In conclusion, the above results suggest that the liver organoids of the present invention can serve as an in vitro model for studying and testing the target organ toxicity induced by hepatic CYP450-mediated drug metabolism.

What is claimed is:

1. A method of constructing a differentiated liver organoid, the method comprising:
    differentiating human pluripotent stem cells into definitive endoderm cells;
    differentiating the definitive endoderm cells into hepatic endoderm cells in a first medium comprising BMP4 and SB431542;
    differentiating the hepatic endoderm cells into a hepatic endoderm organoid in a second medium comprising:
        30 to 70 ng/ml of FGF10;
        5 to 45 ng/ml of HGF;
        1 to 20 mM of nicotinamide;
        1 to 20 nM of [Leu$^{15}$]-Gastrin I human;
        0.25 to 2.25 nM of N-acetyl-L-cysteine;
        1 to 9 μM of A83-01;
        5 to 15 μM of Forskolin; and
        1 to 5 μM of CHIR99021;
        wherein the second medium does not include R-spondin 1 and EGF; and
    differentiating the hepatic endoderm organoid into a differentiated liver organoid in a third medium comprising iron ions, wherein the third medium does not include EGF, and wherein the differentiated liver organoid comprises biliary-like cells, gallbladder-like cells and hepatocyte-like cells.

2. The method of claim 1, wherein the human pluripotent stem cells are human embryonic stem cells or human induced pluripotent stem cells.

3. The method of claim 1, wherein the step of differentiating the definitive endoderm cells into the hepatic endoderm cells is conducted until a ratio of the hepatic endoderm cells to total cells reaches 95% or more.

4. The method of claim 1, wherein the hepatic organoid is cultured in a droplet or a suspension.

5. The method of claim 1, further comprising cryopreserving and subsequently thawing the hepatic endoderm organoid.

6. The method of claim 1, wherein the step of differentiating the hepatic endoderm cells into the hepatic endoderm organoid takes place for a time period of from 13 days to 25 days, wherein the step of differentiating includes first generating the hepatic endoderm organoids for a time period of from 10 days to 18 days and then expanding the hepatic endoderm organoids for a time period of from 3 days to 7 days.

7. The method of claim 1, wherein the second medium does not include Noggin.

8. The method of claim 1, wherein the third medium comprises iron ions selected from the group consisting of ferric citrate, iron chloride, iron sulfate, ferric sulfate, iron nitrate, and pentacarbonyl iron.

9. The method of claim 8, wherein the third medium comprises the ferric citrate at a concentration of from 10 to 30 μM.

10. The method of claim 1, wherein the differentiated liver organoid is cultured in a droplet or a suspension.

11. The method of claim 1, wherein the step of differentiating the hepatic endoderm organoid into the differentiated liver organoid comprises subculturing the hepatic endoderm organoid.

12. The method of claim 11, wherein the step of subculturing the hepatic endoderm organoid takes place in the third medium, wherein the third medium does not include R spondin-1.

13. The method of claim 11, wherein the step of subculturing the hepatic endoderm organoid takes place for a time period of from 3 days to 7 days.

14. The method of claim 1, wherein the step of differentiating the hepatic endoderm organoid into the differentiated liver organoid takes place for a time period of from 10 days to 20 days.

* * * * *